US008207315B2

(12) United States Patent
Wang et al.

(10) Patent No.: US 8,207,315 B2
(45) Date of Patent: Jun. 26, 2012

(54) GENE AND PROTEIN ASSOCIATED WITH ANGIOGENESIS AND ENDOTHELIAL CELL-SPECIFIC APOPTOSIS

(75) Inventors: Qing K. Wang, Shaker Heights, OH (US); Xiao-Li Tian, Beijing (CN); Rajkumar Kadaba, Ottawa (CA)

(73) Assignee: The Cleveland Clinic Foundation, Cleveland, OH (US)

( * ) Notice: Subject to any disclaimer, the term of this patent is extended or adjusted under 35 U.S.C. 154(b) by 579 days.

(21) Appl. No.: 10/569,744

(22) PCT Filed: Aug. 20, 2004

(86) PCT No.: PCT/US2004/027324
§ 371 (c)(1),
(2), (4) Date: Jun. 15, 2007

(87) PCT Pub. No.: WO2005/019432
PCT Pub. Date: Mar. 3, 2005

(65) Prior Publication Data
US 2008/0199473 A1    Aug. 21, 2008

Related U.S. Application Data

(60) Provisional application No. 60/496,879, filed on Aug. 20, 2003.

(51) Int. Cl.
*C07H 21/02* (2006.01)
(52) U.S. Cl. .................................................. 536/23.1
(58) Field of Classification Search ........................ None
See application file for complete search history.

(56) References Cited

FOREIGN PATENT DOCUMENTS

WO    WO 03/038130 A2    5/2003
WO    WO 03/038130 A3    5/2003

OTHER PUBLICATIONS

Reymond et al (PNAS, Oct. 1985, 82(20): 7005-9).*
Burgess et al. (J. Cell Biol. 111:2129-2138, 1990).*
Lazar et al. ( Mol. Cell Biol. 8:1247-1252, 1998).*
Strausberg et al (PNAS, 2002, 99(26): 16899-16903).*
Lodmell et al (Vaccine, 2000, 18:1059-1066).*
Holmen et al (In Vitro Cell Dev. Biol., 1995, 347-351).*
Tian et al.; "Identification of an angiogenic factor that when mutated causes susceptibility to Klippel—Trenaunay syndrome"; Nature, Feb. 12, 2004, vol. 427, pp. 640-645.
Mulitple Authors, "Mus musculus cDNA clone MGC:63399 IMAGE:571644, complete cds," EMBL Database Accession No. BC052410 [retrieved on-line May 3, 2008] (May 21, 2003).
Strausberg, R., "Homo sapiens, hypothetical protein FLJ10283, clone MGC: 32577 IMAGE: 4252711, mRNA, complete cds," EMBL Database Accession No. BC029382 [retrieved on-line May 3, 2008] (May 25, 2002).
Multiple Authors, "Mus musculus adult male tongue cDNA, Riken full-length enriched library, clone:2310029P06 product:hypothetical D111/G-patch doma in/Forkhead-associated (FHA) domain containing protein, full insert sequence," EMBL Database Accession No. AK009533 [retrieved on-line May 3, 2008] (Feb. 8, 2001).
Ota, T., et al., "Primer for synthesizing full-length cDNA and use thereof," JPOP Database Accession No. BD567396 [retrieved on-line Apr. 3, 2008] (Jan. 17, 2003).
Ota, T., et al., "Human protein sequence SEQ ID No. 10997," GSP Database Accession No. AAB92654 [retrieved on-line Apr. 3, 2008] (Jun. 26, 2001).
Ota, T., et al., "Human cDNA sequence SEQ ID No. 10996," GSN Database Accession No. AAH13953 [retrieved on-line May 3, 2008] (Jun. 26, 2001).
Birse, C.E., "Human polypeptide SEQ ID No. 1431," GSP Database Accession No. ABB89055 [retrieved on-line Apr. 3, 2008] (May 24, 2002).
Multiple Authors, "Homo sapiens fetal unknown mRNA, complete cds," EMBL Database Accession No. U84971 [retrieved on-line May 3, 2008] (Jun. 26, 1997).
Whelan, A.J., et al., "Klippel-Trenaunay-Weber syndrome associated with a 5:11 balanced translocation," US National Library of Medicine (NLM), Bethesda, MD, Medline Database Accession No. NLM8585570 [retrieved on-line May 3, 2008] (Dec. 4, 1995).
Donohue, P.J., et al., "TWEAK is an Endothelial Cell Growth and Chemotactic Factor That Also Potentiates FGF-2 and VEGF-A Mitogenic Activity," *Arterioscler Thromb Vasc Biol.*, 23:594-600.
Farina, A., et al., "Evidence of Genetic Underexpression in Chorionic Villi Samples of Euploid Fetuses with Increased Nuchal Translucency at 10-11 Weeks' Gestation," *Prenot Diagn.*, 26:128-133 (2006).
Timur, A.A., et al,, "Biomedicine and Diseases: The Klippel-Trenaunay Syndrome, Vascular Anomalies and Vascular Morphogenesis," *CMLS Cell. Mol. Life Sci.*, 62(13):1434-1447 (2005).
Mar. 28, 2005, Notification of Transmittal of the International Search Report and the Written Opinion of the International Searching Authority, PCT/US04/27324.
Mar. 2, 2006, Notification Concerning Transmittal of International Preliminary Report on Patentability, PCT/US04/27324.
Oct. 12, 2007, Voluntary Amendment and Sequence Listing, 2,535,976.
Mar. 28, 2006, Communication Pursuant to Rules 109 and 110 EPC, 04786556.3.
Mar. 18, 2008, Supplementary European Search Report, 04786556.3.
Nov. 21, 2008, Communication pursuant to Article 94(3) EPC—Office Action, 04786556.3.

(Continued)

*Primary Examiner* — Sean Aeder
(74) *Attorney, Agent, or Firm* — Hamilton, Brook, Smith & Reynolds, P.C.

(57) ABSTRACT

This invention provides isolated nucleic acid and amino acid sequences encoding VG5Q, a novel angiogenic growth factor protein with pro-angiogenic activity, a forkhead-associated domain, a G-patch domain; characteristic subcellular localization in an in vitro Matrigel model of angiogenesis: towards the cell periphery in early stages of tubulogenesis, between cells in newly formed endothelial tubes, and no nuclear staining after 24 hours; is expressed in endothelial cells; is secreted during angiogenesis; and interacts with TWEAK. The invention also provides for expression vectors containing nucleic acid sequences encoding VG5Q protein, and host cells containing one or more expression vectors for the recombinant expression of VG5Q. The invention also provides for methods of using VG5Q for the diagnosis and treatment of angiogenesis-mediated diseases or disorders.

20 Claims, 12 Drawing Sheets

OTHER PUBLICATIONS

Chicheportiche, Y., et al., "TWEAK, a New Secreted Ligand in the Tumor Necrosis Factor Family That Weakly Induces Apoptosis," *The Journal of Biological Chemistry*, 272(51): 32401-32410 (1997).

Filleur, S., et al., "SiRNA-mediated inhibition of Vascular Endothelial Growth Factor Severely Limits Tumor Resistance to Antiangiogenic Thrombospondin-1 and Slows Tumor Vascularization and Growth," *Cancer Research*, 63:3919-3922 (2003).

GenBank Accession No. AA311507, Adams, M.D., et al.,"EST182252 Jurkat T-cells V Homo sapiens cDNA 5-end, mRNA sequence."

GenBank Accession No. AI037948, NCI-CGAP, "ox53b11.x1 Soares_total_fetus_Nb2HF8_9w Homo sapiens cDNA clone."

GenBank Accession No. AI925946, NCI-CGAP, "whl2f04.x1 NCI_CGAP_Kid11 Homo sapiens cDNA clone."

GenBank Accession No. AI939311, NCI/NINDS-CGAP, "qa15d09.x5 NCI_CGAP_Brn23 Homo sapiens cDNA clone."

Lipscomb, E., et al., "Use of RNA Interference to Inhibit Integrin (α6β4)-mediated Invasion and Migration of Breast Carcinoma Cells," *Clinical & Experimental Metastasis*, 20:569-576 (2003).

Lynch, C., et al., "TWEAK Induces Angiogenesis and Proliferation of Endothelial Cells," *The Journal of Biological Chemistry*, 274(13): 8455-8459 (1999).

Martinez, L., et al., "Synthetic Small Inhibiting RNAs: Efficient Tools to Inactivate Oncogenic Mutations and Restore p53 Pathways,"*PNAS*, 99(23): 14849-14854 (2002).

Mignatti, P., et al., "Basic Fibroblast Growth Factor, a Protein Devoid of Secretory Signal Sequence, Is Released by cells Via a Pathway Independent of the Endoplasmic Reticulum-Golgi Complex," *Journal of Cellular Physiology*, 151:81-93 (1992).

Nakayama, M., et al., "Fibroblast Growth Factor-Inducible 14 Mediated Multiple Pathways of TWEAK-Induced Cell Death," *The Journal of Immunology*, 170: 341-348 (2003).

Nakayama, M., et al., "Multiple Pathways of TWEAK-Induced Cell Death," *The Journal of Immunology*, 168: 734-743 (2002).

O'Reilly, M. S., "Targeting Multiple Biological Pathways as A Strategy to Improve the Treatment of Cancer," Clinical Cancer Research, 8:3309-3310 (2002).

Pfeffer, S., "Membrane Domains in the Secretory and Endocytic Pathways," *Cell*, 112:507-517 (2003).

Risau, W., "Mechanisms of Angiogenesis," *Nature*, 386:671-674 (1997).

Saitoh, T., et al,, "TWEAK Induces NF-κB2 p100 Processing and Long Lasting NF-κb Activation," *The Journal of Biological Chemistry*, 278(38): 36005-36012 (2003).

Wang, H., et al., "Subcellular Localization of Pentachlorophenol 4-monoxygenase in Sphingobium Chlorophenolicum ATCC 39723," *Biochemical and Biophysical Research Communications*, 299: 703-709 (2002).

Wiley, S., et al., "A Novel TNF Receptor Family Member Binds TWEAK and Is Implicated in Angiogenesis," *Immunity*, 15: 837-846 (2001).

Wiley, S., et al,, "TWEAK, A Member of the TNF Superfamily, is a Multifunctional Cytokine That Binds the TweakR/Fn14 Receptor," *Cytokine Growth Factor Reviews*, 14: 241-249 (2003).

Yancopoulos, G., et al., "Vascular-Specific Growth Factors and Blood Vessel Formation," *Nature*, 407: 242-248 (2000).

\* cited by examiner

FIGURE 2

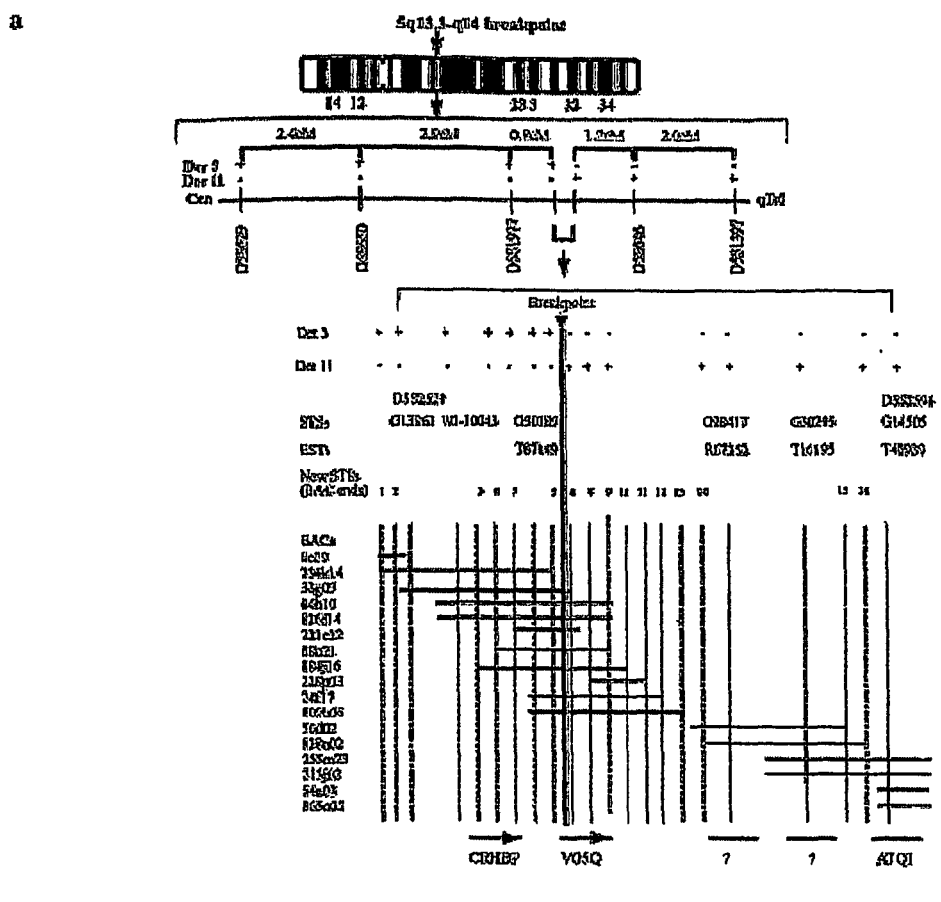

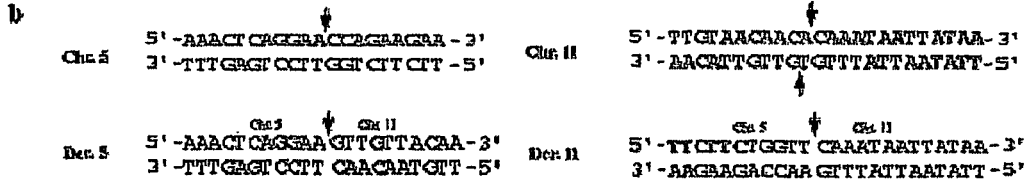

MASEAPSPPRSPPPPTSPEPELAQLRRKVEKLERELRSCKRQVREIEKLLHHTERLYQNAESMNQEL 67
RTQVEELSKILQRGRNEDNKKSDVEVQTENHAPWSISDYFYQTYYMDVSLPNKVTELSDQQDQAIET 134
SILNSKDHLQVENDAYPGTDRTENVKYRQVDHFASWSQEPASALATEDTSLEGSSLAESLRAAAEAA 201
VSQTGFSYDENTGLYFDHSTGFYYDSENQLYYDPSTGIYYYCDVESGRYQFHSRVDLQPYPTSSTKQ 268
SKDKKLKKKRKDPDSSATNEERDLNSEDQKAFSVEHTSCNEEENFANMKKKAKIGIHHKNSPPKVTV 335
PTSGNTIESPLHENISWSTSFKDEKIMETDSEPEEGEITDSQTEDSYDEAITSEGNVTAEDSEDEDE 402
DKIWPPCIRVTVIRSPVLQIGSLFIITAVNPATIGREKDMEHTLRIPEVGVSKFHAEIYFDHDLQSY 469
VLVDQGSQWGTIVNGKQILQPKTKCDPYVLEHGDEVKIGETVLSFHIHPGSDTCDGCEPGQVRAHLR 536
LDKKDESFVGPTLSKEEKELERRKELKKTRVKYGLQNTEYEDEKTLKNPKYKDRAGKRREQVGSEGT 603
FQRDDAPASVHSEITDSNKGRKDLEKNGWKKGEGLGKDGGMKTPIQLQLRRTHAGLGTGKPSSFED 670
VHLLQNKNKHWDKARERFTENFPETKPQKDDPGTMPWVKGTLE 714

Figure 3

```
1    GCTTATCCGACGCTCCTCCCTCTGTCTCTGTAGCTGGAGAAGGTAGTTTCCAGGAAAGTT
61   TTCCGGTTTGCAGGCCGCGCACATCGGGCAGGGGCCATCCTCGGTCCCCTTGCTCGTTGC
121  TCGCAGCCCCGTTCGGCTACAAGTGAGTTTCAGGGCGTCATGGCCAGGGGCCACCGCGGC
181  CAGCCGGGTGTGAGGCTGCCTTTCGCTGCCCGCGCGCTCCAGTGGTCTCTGGGTCCGCCG
241  GCGTCCGTTTCGGCCTGAACGCAGCCCCTCCGCGGCGACGAGCAGTCTCGCGCCGGAGCT
301  CATGGCCTCGGAGGCGCCGTCCCCGCCGCGGTCGCCGCCGCCGCCCACCTCCCCCGAGCC
```

1      M  A  S  E  A  P  S  P  P  R  S  P  P  P  P  T  S  P  E  P

361    TGAGCTGGCCCAGCTAAGGCGGAAGGTGGAGAAGTTGGAACGTGAACTGCGGAGCTGCAA

21     E  L  A  Q  L  R  R  K  V  E  K  L  E  R  E  L  R  S  C  K

431    GCGGCAGGTGCGGGAGATCGAGAAGCTGCTGCATCACACAGAACGGCTGTACCAGAACGC

41     R  Q  V  R  E  I  E  K  L  L  H  H  T  E  R  L  Y  Q  N  A

481    AGAAAGCAACAACCAGGAGCTCCGCACGCAGGTGGAAGAACTCAGTAAAATACTCCAACG

61     E  S  N  N  Q  E  L  R  T  Q  V  E  E  L  S  K  I  L  Q  R

541    TGGGAGAAATGAAGATAATAAAAAGTCTGATGTAGAAGTACAAACAGAGAACCATGCTCC

81     G  R  N  E  D  N  K  K  S  D  V  E  V  Q  T  E  N  H  A  P

601    TTGGTCAATCTCAGATTATTTTTATCAGACGTACTACAATGACGTTAGTCTTCCAAATAA

101    W  S  I  S  D  Y  F  Y  Q  T  Y  Y  N  D  V  S  L  P  N  K

661    AGTGACTGAACTGTCAGATCAACAAGATCAAGCTATCGAAACTTCTATTTTGAATTCTAA

121    V  T  E  L  S  D  Q  Q  D  Q  A  I  K  T  S  I  L  N  S  K

721    AGACCATTTACAAGTAGAAAATGATGCTTACCCTGGTACCGATAGAACAGAAAATGTTAA

141    D  H  L  Q  V  E  N  D  A  Y  P  G  T  D  R  T  E  N  V  K

781    ATATAGACAAGTGGACCATTTTGCCTCAAATTCACAGGAGCCAGCATCTGCATTAGCAAC

161    Y  R  Q  V  D  H  F  A  S  N  S  Q  E  P  A  S  A  L  A  T

841    AGAAGATACCTCCTTAGAAGGCTCATCATTAGCTGAAAGTTTGAGAGCTGCAGCAGAAGC

181    E  D  T  S  L  E  G  S  S  L  A  E  S  L  R  A  A  A  E  A

901    GGCTGTATCACAGACTGGATTTAGTTATGATGAAAATACTGGACTGTATTTTGACCACAG

201    A  V  S  Q  T  G  F  S  Y  D  E  N  T  G  L  Y  F  D  H  S

961    CACTGGTTTCTATTATGATTCTGAAAATCAACTCTATTATGATCCTTCCACTGGAATTTA

221    T  G  F  Y  Y  D  S  E  N  Q  L  Y  Y  D  P  S  T  G  I  Y

1021   TTACTATTGTGATGTGGAAAGTGGTCGTTATCAGTTTCATTCTCGAGTAGATTTGCAACC

241    Y  Y  C  D  V  E  S  G  R  Y  Q  F  H  S  R  V  D  L  Q  P

1081   TTATCCGACTTCTAGCACAAAACAAAGTAAAGATAAAAAATTGAAGAAGAAAAGAAAAGA

261    Y  P  T  S  S  T  K  Q  S  K  D  K  K  L  K  K  K  R  K  D

1141   TCCAGATTCTTCTGCAACAAATGAGGAAAAGGATTTGAACTCAGAGGATCAAAAAGCCTT

281    P  D  S  S  A  T  N  E  E  K  D  L  N  S  E  D  Q  K  A  F

1201   CAGTGTTGAACATACAAGCTGCAATGAGGAAGAAAATTTCGCAAATATGAAAAAGAAGGC

301    S  V  E  H  T  S  C  N  E  E  E  N  F  A  N  M  K  K  K  A

1261   CAAAATAGGCATTCATCACAAAAATAGTCCCCCCAAAGTCACTGTTCCAACTAGTGGAAA

321    K  I  G  I  H  H  K  N  S  P  P  K  V  T  V  P  T  S  G  N

1321   TACTATAGAGTCTCCTCTTCATGAAAACATCTCTAATTCAACATCATTTAAAGATGAGAA

341    T  I  E  S  P  L  H  E  N  I  S  N  S  T  S  F  K  D  E  K

1381   AATCATGGAGACTGATAGTGAACCAGAGGAAGGTGAAATTACAGACTCTCAGACTGAGGA

361    I  M  E  T  D  S  E  P  E  E  G  E  I  T  D  S  Q  T  E  D

1441   TAGTTATGACGAAGCCATTACCAGTGAAGGCAATGTAACTGCAGAAGATAGTGAGGATGA

381    S  Y  D  E  A  I  T  S  E  G  N  V  T  A  E  D  S  E  D  E

1501   AGATGAAGACAAAATCTGGCCCCCCATGTATTAGAGTAATTGTCATTAGATCACCCGTGTT

401    D  E  D  K  I  W  P  P  C  I  R  V  I  V  I  R  S  P  V  L

1561   GCAGATAGGATCACTCTTTATCATTACTGCTGTAAACCCTGCTACAATTGGAAGAGAAAA

```
1621  GGATATGGAACATACTCTCCGAATCCCTGAAGTTGGTGTCAGTAAGTTTCATGCAGAAAT
 441    D   M   E   H   T   L   R   I   P   E   V   G   V   S   K   F   H   A   E   I
1681  TTATTTTGACCATGACTTACAAAGTTATGTCCTTGTGGATCAAGGCAGTCAAAATGGCAC
 461    Y   F   D   H   D   L   Q   S   Y   V   L   V   D   Q   G   S   Q   N   G   T
1741  AATTGTTAATGGAAAACAGATTCTTCAGCCGAAAACTAAATGTGACCCTTACGTACTTGA
 481    I   V   N   G   K   Q   I   L   Q   P   K   T   K   C   D   P   Y   V   L   E
1801  GCATGGAGATGAAGTCAAAATTGGAGAAACTGTCTTATCCTTTCACATTCATCCTGGCAG
 501    H   G   D   E   V   K   I   G   E   T   V   L   S   F   H   I   H   P   G   S
1861  TGATACCTGTGATGGCTGTGAACCAGGGCAGGTTAGAGCCCACCTTCGCCTTGATAAGAA
 521    D   T   C   D   G   C   E   P   G   Q   V   R   A   H   L   R   L   D   K   K
1921  AGATGAATCTTTTGTTGGTCCAACACTAAGTAAGGAGGAAAAAGAGTTGGAAAGAAGAAA
 541    D   E   S   F   V   G   P   T   L   S   K   E   E   K   E   L   E   R   R   K
1981  AGAATTAAAGAAAATACGAGTAAAATATGGTTTACAGAATACAGAATACGAAGATGAAAA
 561    E   L   K   K   I   R   V   K   Y   G   L   Q   N   T   E   Y   E   D   E   K
2041  GACATTGAAGAATCCAAAATATAAAGATAGAGCTGGAAAACGTAGGGAGCAGGTTGGAAG
 581    T   L   K   N   P   K   Y   K   D   R   A   G   K   R   E   E   Q   V   G   S
2101  TGAAGGAACTTTCCAAAGAGATGATGCTCCTGCATCTGTTCATTCTGAAATTACTGATAG
 601    E   G   T   F   Q   R   D   D   A   P   A   S   V   H   S   E   I   T   D   S
2161  CAACAAAGGTCGGAAGATGTTGGAGAAGATGGGTTGGAAGAAAGGAGAGGGCCTGGGGAA
 621    N   K   G   R   K   M   L   E   K   M   G   W   K   K   G   E   G   L   G   K
2221  GGATGGTGGAGGAATGAAAACGCCGATCCAGCTTCAGCTTCGGCGAACACATGCAGGCTT
 641    D   G   G   M   K   T   P   I   Q   L   Q   L   R   R   T   H   A   G   L
2281  GGGGACAGGCAAACCATCCTCATTTGAAGATGTTCACCTTCTCCAAAACAAGAACAAAAA
 661    G   T   G   K   P   S   S   F   E   D   V   H   L   L   Q   N   K   N   K
2341  AAACTGGGACAAAGCACGAGAGCGGTTTACTGAAAACTTCCCAGAAACTAAGCCTCAAAA
 681    N   W   D   K   A   R   E   R   F   T   E   N   F   P   E   T   K   P   Q   K
2401  AGATGACCCAGGGACCATGCCTTGGGTAAAAGGGACTTTAGAGTGAAGGCTAATCATAGA
 701    D   D   P   G   T   M   P   W   V   K   G   T   L   E *
2461  AAAAAAACCTCTAGTTTTTTTAAAAATAGAATTTGGAAACTTATTTTTTCTCCCCAAAAG
2521  AATCAGCAGCACAGGGGAACTATGTCACAGTTTACCTCTTCCTGATTCAGAAATGTGTAT
2581  GGTTTGCAGCTTTTAAAAACCATTTTTTTAAAACTAATAAATAGTGACTGAACCAATTTA
2641  TGCAGTAAATAGACTAAAGTTCACAGGGCACGGATGAGTTTATCAAACTTCGTTATTTTA
2701  TCTTCATTTACAACATCCATATAAGCAACTAGCCATATAAGCAAAATTCATAGAACTACT
2761  AATGACTTAAGTGTACATCTGTTCTTGTCTCCATATATTCATGTAAGATGCACAACAAAA
2821  GAAACATCAGAAGTTTATAAAAATAAATCTGACTATACGCATCCTCATTTATTCCCTTTA
2881  GAACCTAGGTAAAAAATGTTGCGAAAACATGGGTAGTGGCGCATACATTTTGTTATCCTT
2941  GAAATAGCCTAAGTAATGTTATTGAAGAACTAATGAACAGGTAACATATTGTAGAAAATT
3001  AGTCTTTCATTGTTTTCTTCTGTGAAGAATCTGTTGCTATGTACTGTATATTCAGCATTT
3061  ATATTTGGTTTGTTTCATAGCTAATGAGGTATTTAGATATGAACAACTGAATACATATTG
3121  AAATAGTGTGCTGGCTTTTGTAGTTTTGATAAAGACCATTGCAGGCAATGGAATTGTGCC
3181  AGAGAAATCTGATTTCTAGTACAAAAGGAATACTTAGCCAGGGCCTCAAGCTCAAGATAC
3241  TTATTGAAAACATCCTCAATTGCAATAAAAACATTATAACATGAAAAAGAGTGATTTTTT
3301  GAACCGGTGATTTAAATGTATTGATCTGCTTTGAATTTTCAAGCAGCCAGAATTTTCTAG
3361  TTTAAATTGGCAGAGTTATAACAAAGGAGAGCCTCAAATATTTAGACAATTGCAGTGCGGC
3421  TTTCTGGGCACAGGTGTCACTGCTCTGCCACCTATCACTATTCTTTTTCTGTTCAGTTTT
3481  TCTCTCAGGTGTTTGCTGGGGAAATTAACACTGGGAACTGACCCTTTTCTGGGCAGTGAA
3541  TGTAAGCTCTAGCTCCCCCATCTACTATAAAGAAATGTCTTTGAGATGTAGAAATAAGGA
3601  ATATTCTGAAAATAAAAATTATACAGTAGTAAAGATAATTCAGAAAGAAAAAGCTACCTG
3661  TTAGAATTTCCAGTCTAAATGGCACAGGGTAGTTACGGAGAAAAGGGGATGGAGAAGGAG
3721  AAACTATGACTAAAGATGAGAGGTATGAACGAGTTGTCAGGTTCCTATGGGCTTAAGCTA
3781  GGACAATCAGGCCCTAAACTCCAAATTTGGATAAAATATCTCTTTGCATTCTTCTTGGCC
3841  ACCTGCATAGTCTGACACATACGTATGTACAGTTAGACTTGCAGGCTGCAGGAGTGCCCT
3901  GCATTGTTTCTTTTAATTAGAAAATAAAAGTATTAGTCTAAATGTGGNTCTTGTGCTGGT
3961  GCCCTGTATATATGTAACAATATAGGACCCCCTCCAAATAGGTTTTGCTTCTGGTGAATC
4021  TTGGTCATTTGGTTAAGATATGACTGTCC
```

FIGURE 10
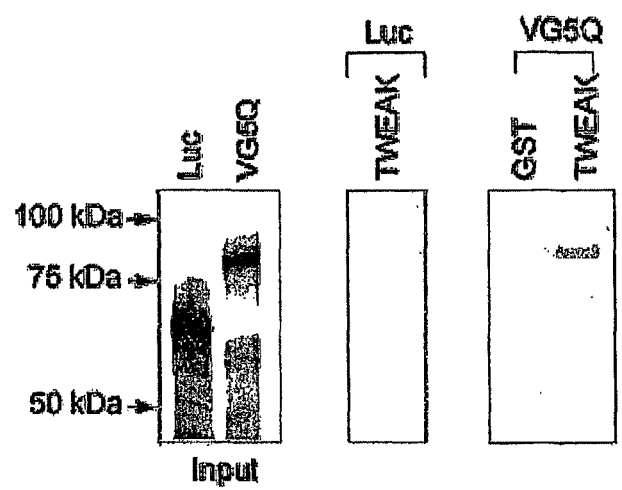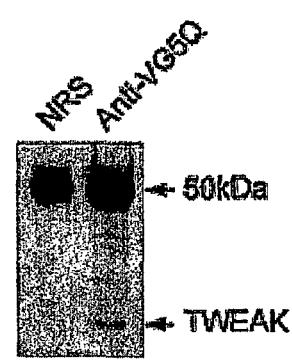

SEQUENCE LISTING

<160> NUMBER OF SEQ ID NOS: 51

<210> SEQ ID NO 1
<211> LENGTH: 4049
<212> TYPE: DNA
<213> ORGANISM: Homo sapiens
<220> FEATURE:
<221> NAME/KEY: misc_feature
<222> LOCATION: (3948)...(3948)
<223> OTHER INFORMATION: n is a, c, g, or t

<400> SEQUENCE: 1

```
gcttatccga cgctcctccc tctgtctctg tagctggaga aggtagtttc caggaaagtt      60
ttccggtttg caggccgcgc acatcgggca ggggccatcc tcggtcccct tgctcgttgc     120
tcgcagcccc gttcggctac aagtgagttt cagggcgtca tggccagggg ccaccgcggc     180
cagccgggtg tgaggctgcc tttcgctgcc cgcgcgctcc agtggtctct gggtccgccg     240
gcgtccgttt cggcctgaac gcagcccctc cgcggcgacg agcagtctcg cgccggagct     300
catggcctcg gaggcgccgt ccccgccgcg gtcgccgccg ccgcccacct ccccgagcc      360 tgagctggcc cagctaaggc ggaaggtgga gaagttggaa cgtgaactgc ggagctgcaa     420
gcggcaggtg cgggagatcg agaagctgct gcatcacaca gaacggctgt accagaacgc     480
agaaagcaac aaccaggagc tccgcacgca ggtggaagaa ctcagtaaaa tactccaacg     540
tgggagaaat gaagataata aaaagtctga tgtagaagta caaacagaga accatgctcc     600
ttggtcaatc tcagattatt tttatcagac gtactacaat gacgttagtc ttccaaataa     660
agtgactgaa ctgtcagatc aacaagatca agctatcgaa acttctattt tgaattctaa     720
agaccattta caagtagaaa atgatgctta ccctggtacc gatagaacag aaaatgttaa     780
atatagacaa gtggaccatt ttgcctcaaa ttcacaggag ccagcatctg cattagcaac     840
agaagatacc tccttagaag gctcatcatt agctgaaagt ttgagagctg cagcagaagc     900
ggctgtatca cagactggat ttagttatga tgaaaatact ggactgtatt ttgaccacag     960
cactggtttc tattatgatt ctgaaaatca actctattat gatccttcca ctggaatta    1020 ttactattgt gatgtggaaa gtggtcgtta tcagtttcat tctcgagtag atttgcaacc    1080
ttatccgact tctagcacaa aacaaagtaa agataaaaaa ttgaagaaga aagaaaaga    1140 tccagattct tctgcaacaa atgaggaaaa ggatttgaac tcagaggatc aaaaagcctt    1200
cagtgttgaa catacaagct gcaatgagga agaaaatttc gcaaatatga aaagaaggc    1260 caaaataggc attcatcaca aaaatagtcc ccccaaagtc actgttccaa ctagtggaaa    1320
tactatagag tctcctcttc atgaaaacat ctctaattca acatcattta aagatgagaa    1380
aatcatggag actgatagtg aaccagagga aggtgaaatt acagactctc agactgagga    1440
```

```
tagttatgac gaagccatta ccagtgaagg caatgtaact gcagaagata gtgaggatga   1500
agatgaagac aaaatctggc ccccatgtat tagagtaatt gtcattagat cacccgtgtt   1560
gcagatagga tcactctttta tcattactgc tgtaaaccct gctacaattg aagagaaaa    1620 ggatatggaa catactctcc gaatccctga agttggtgtc agtaagtttc atgcagaaat   1680
ttattttgac catgacttac aaagttatgt ccttgtggat caaggcagtc aaaatggcac   1740
aattgttaat ggaaaacaga ttcttcagcc gaaaactaaa tgtgacccct acgtacttga   1800
gcatggagat gaagtcaaaa ttggagaaac tgtcttatcc tttcacattc atcctggcag   1860
tgatacctgt gatggctgtg aaccagggca ggttagagcc caccttcgcc ttgataagaa   1920
agatgaatct tttgttggtc aacactaag taaggaggaa aaagagttgg aaagaagaaa    1980
agaattaaag aaaatacgag taaaatatgg tttacagaat acagaatacg aagatgaaaa   2040
gacattgaag aatccaaaat ataaagatag agctggaaaa cgtagggagc aggttggaag   2100
tgaaggaact ttccaaagag atgatgctcc tgcatctgtt cattctgaaa ttactgatag   2160
caacaaaggt cggaagatgt tggagaagat gggttggaag aaaggagagg gcctggggaa   2220
ggatggtgga ggaatgaaaa cgccgatcca gcttcagctt cggcgaacac atgcaggctt   2280
ggggacaggc aaaccatcct catttgaaga tgttcacctt ctccaaaaca gaacaaaaa    2340 aaactgggac aaagcacgag agcggtttac tgaaaacttc ccagaaacta gcctcaaaa    2400 agatgaccca gggaccatgc cttgggtaaa agggacttta gagtgaaggc taatcataga   2460
aaaaaaacct ctagtttttt taaaaataga atttggaaac ttattttttc tccccaaaag   2520
aatcagcagc acaggggaac tatgtcacag tttacctctt cctgattcag aaatgtgtat   2580
ggtttgcagc ttttaaaaac cattttttta aaactaataa atagtgactg aaccaattta   2640
tgcagtaaat agactaaagt tcacagggca cggatgagtt tatcaaactt cgttattta    2700 tcttcattta caacatccat ataagcaact agccatataa gcaaaattca tagaactact   2760
aatgacttaa gtgtacatct gttcttgtct ccatatattc atgtaagatg cacaacaaaa   2820
gaaacatcag aagtttataa aaataaatct gactatacgc atcctcattt attcccttta   2880
gaacctaggt aaaaaatgtt gcgaaaacat gggtagtggc gcatacattt tgttatcctt   2940
gaaatagcct aagtaatgtt attgaagaac taatgaacag gtaacatatt gtagaaaatt   3000
agtctttcat tgttttcttc tgtgaagaat ctgttgctat gtactgtata ttcagcattt   3060
atatttggtt tgtttcatag ctaatgaggt atttagatat gaacaactga atacatattg   3120
aaatagtgtg ctggcttttg tagttttgat aaagaccatt gcaggcaatg gaattgtgcc   3180
agagaaatct gatttctagt acaaaaggaa tacttagcca gggcctcaag ctcaagatac   3240
ttattgaaaa catcctcaat tgcaataaaa acattataac atgaaaaaga gtgatttttt   3300
gaaccggtga tttaaatgta ttgatctgct ttgaattttc aagcagccag aattttctag   3360
tttaaattgg cagagttata acaaaggaga gcctcaaata ttagacaatt gcagtgcggc   3420
tttctgggca caggtgtcac tgctctgcca cctatcacta ttcttttct gttcagtttt     3480 tctctcaggt gtttgctggg gaaattaaca ctgggaactg acccttttct gggcagtgaa   3540
tgtaagctct agctccccca tctactataa agaaatgtct ttgagatgta gaaataagga   3600
atattctgaa aataaaaatt atacagtagt aaagataatt cagaaagaaa aagctacctg   3660
ttagaatttc cagtctaaat ggcacagggt agttacggag aaaaggggat ggagaaggag   3720
aaactatgac taaagatgag aggtatgaac gagttgtcag gttcctatgg gcttaagcta   3780
ggacaatcag gccctaaact ccaaatttgg ataaaatatc tctttgcatt cttcttggcc   3840
```

```
acctgcatag tctgacacat acgtatgtac agttagactt gcaggctgca ggagtgccct   3900
gcattgtttc ttttaattag aaaataaaag tattagtcta aatgtggntc ttgtgctggt   3960
gccctgtata tatgtaacaa tataggaccc cctccaaata ggttttgctt ctggtgaatc   4020
ttggtcattt ggttaagata tgactgtcc                                    4049
```

<210> SEQ ID NO 2
<211> LENGTH: 714
<212> TYPE: PRT
<213> ORGANISM: Homo sapiens

<400> SEQUENCE: 2

```
Met Ala Ser Glu Ala Pro Ser Pro Pro Arg Ser Pro Pro Pro Pro Thr
 1               5                  10                  15

Ser Pro Glu Pro Glu Leu Ala Gln Leu Arg Arg Lys Val Glu Lys Leu
                20                  25                  30

Glu Arg Glu Leu Arg Ser Cys Lys Arg Gln Val Arg Glu Ile Glu Lys
            35                  40                  45

Leu Leu His His Thr Glu Arg Leu Tyr Gln Asn Ala Glu Ser Asn Asn
        50                  55                  60

Gln Glu Leu Arg Thr Gln Val Glu Leu Ser Lys Ile Leu Gln Arg
65                  70                  75                  80

Gly Arg Asn Glu Asp Asn Lys Lys Ser Asp Val Glu Val Gln Thr Glu
                85                  90                  95

Asn His Ala Pro Trp Ser Ile Ser Asp Tyr Phe Tyr Gln Thr Tyr Tyr
            100                 105                 110

Asn Asp Val Ser Leu Pro Asn Lys Val Thr Glu Leu Ser Asp Gln Gln
        115                 120                 125

Asp Gln Ala Ile Glu Thr Ser Ile Leu Asn Ser Lys Asp His Leu Gln
    130                 135                 140

Val Glu Asn Asp Ala Tyr Pro Gly Thr Asp Arg Thr Glu Asn Val Lys
145                 150                 155                 160

Tyr Arg Gln Val Asp His Phe Ala Ser Asn Ser Gln Glu Pro Ala Ser
                165                 170                 175

Ala Leu Ala Thr Glu Asp Thr Ser Leu Glu Gly Ser Ser Leu Ala Glu
            180                 185                 190

Ser Leu Arg Ala Ala Glu Ala Ala Val Ser Gln Thr Gly Phe Ser
        195                 200                 205

Tyr Asp Glu Asn Thr Gly Leu Tyr Phe Asp His Ser Thr Gly Phe Tyr
    210                 215                 220

Tyr Asp Ser Glu Asn Gln Leu Tyr Tyr Asp Pro Ser Thr Gly Ile Tyr
225                 230                 235                 240

Tyr Tyr Cys Asp Val Glu Ser Gly Arg Tyr Gln Phe His Ser Arg Val
                245                 250                 255

Asp Leu Gln Pro Tyr Pro Thr Ser Ser Thr Lys Gln Ser Lys Asp Lys
            260                 265                 270

Lys Leu Lys Lys Lys Arg Lys Asp Pro Asp Ser Ser Ala Thr Asn Glu
        275                 280                 285

Glu Lys Asp Leu Asn Ser Glu Asp Gln Lys Ala Phe Ser Val Glu His
    290                 295                 300

Thr Ser Cys Asn Glu Glu Asn Phe Ala Asn Met Lys Lys Lys Ala
305                 310                 315                 320

Lys Ile Gly Ile His His Lys Asn Ser Pro Pro Lys Val Thr Val Pro
                325                 330                 335
```

```
Thr Ser Gly Asn Thr Ile Glu Ser Pro Leu His Glu Asn Ile Ser Asn
            340                 345                 350

Ser Thr Ser Phe Lys Asp Glu Lys Ile Met Glu Thr Asp Ser Glu Pro
        355                 360                 365

Glu Glu Gly Glu Ile Thr Asp Ser Gln Thr Glu Asp Ser Tyr Asp Glu
    370                 375                 380

Ala Ile Thr Ser Glu Gly Asn Val Thr Ala Glu Asp Ser Glu Asp Glu
385                 390                 395                 400

Asp Glu Asp Lys Ile Trp Pro Pro Cys Ile Arg Val Ile Val Ile Arg
                405                 410                 415

Ser Pro Val Leu Gln Ile Gly Ser Leu Phe Ile Ile Thr Ala Val Asn
            420                 425                 430

Pro Ala Thr Ile Gly Arg Glu Lys Asp Met Glu His Thr Leu Arg Ile
        435                 440                 445

Pro Glu Val Gly Val Ser Lys Phe His Ala Glu Ile Tyr Phe Asp His
    450                 455                 460

Asp Leu Gln Ser Tyr Val Leu Asp Gln Gly Ser Gln Asn Gly Thr
465                 470                 475                 480

Ile Val Asn Gly Lys Gln Ile Leu Gln Pro Lys Thr Lys Cys Asp Pro
                485                 490                 495

Tyr Val Leu Glu His Gly Asp Glu Val Lys Ile Gly Glu Thr Val Leu
            500                 505                 510

Ser Phe His Ile His Pro Gly Ser Asp Thr Cys Asp Gly Cys Glu Pro
        515                 520                 525

Gly Gln Val Arg Ala His Leu Arg Leu Asp Lys Asp Glu Ser Phe
    530                 535                 540

Val Gly Pro Thr Leu Ser Lys Glu Glu Lys Glu Leu Glu Arg Arg Lys
545                 550                 555                 560

Glu Leu Lys Lys Ile Arg Val Lys Tyr Gly Leu Gln Asn Thr Glu Tyr
                565                 570                 575

Glu Asp Glu Lys Thr Leu Lys Asn Pro Lys Tyr Lys Asp Arg Ala Gly
            580                 585                 590

Lys Arg Arg Glu Gln Val Gly Ser Glu Gly Thr Phe Gln Arg Asp Asp
        595                 600                 605

Ala Pro Ala Ser Val His Ser Glu Ile Thr Asp Ser Asn Lys Gly Arg
    610                 615                 620

Lys Met Leu Glu Lys Met Gly Trp Lys Lys Gly Glu Gly Leu Gly Lys
625                 630                 635                 640

Asp Gly Gly Gly Met Lys Thr Pro Ile Gln Leu Gln Leu Arg Arg Thr
                645                 650                 655

His Ala Gly Leu Gly Thr Gly Lys Pro Ser Ser Phe Glu Asp Val His
            660                 665                 670

Leu Leu Gln Asn Lys Asn Lys Lys Asn Trp Asp Lys Ala Arg Glu Arg
        675                 680                 685

Phe Thr Glu Asn Phe Pro Glu Thr Lys Pro Gln Lys Asp Asp Pro Gly
    690                 695                 700

Thr Met Pro Trp Val Lys Gly Thr Leu Glu
705                 710

<210> SEQ ID NO 3
<211> LENGTH: 3191
<212> TYPE: DNA
<213> ORGANISM: Mus musculus

<400> SEQUENCE: 3
```

-continued

```
ggctgggttc gctttagttc tcccgtccgc tggcttcccg gagactgtca ccgggcgggt    60
gtccgcgcgg cccgggtaga gtcggcttcg tccccaagct cgcagtcccg ccgccgtcct   120
tcggggggcga catggccggg gcccgctgcg gtcgtccgag cgtgaggccg ccctcgcag   180
cccgcgcgct ccagtggccc ctgggccagt gggcccggt gtcgtcctaa gcagccggt    240
ccgcgccccg cgggctcggc gctcacggcc gcatggcctc cgaggcgccc tcgccgcctt   300
cgccttctcc gccgccgccc gcctctccgg agccggagct ggcgcagctc aggcggaagg   360
tggagaagtt ggagcgcgag ctgcggagct gccggaggca ggtgcgggag gtggagaagc   420
tgctgcagca cacggagcga ctctaccgca acgccgagag cgacaaccag gagctccgca   480
cgcaggtaga agaacttagt aaaatactcc attgtgggaa aaatgaagat aatccgaagt   540
ctgatgtaga agtacagaca gagagccaag ctccttgggc gatttcagat tattactatc   600
agacatgtta taatgacgac agtcttccca gtaaagagac ggagctgtgt gtacagcaga   660
gtcagtgtgc tcaggcttcc gctcttgatc ctcaggacga gtcacacata gacagcggga   720
gttatgctgg tgctgatgcc acagaaggtg ttagccatag acaggaggac gccgtcacct   780
ctgactcaca ggagagtgtg tccgcgctag cagaaggccc agcactcgaa gggtcctcgc   840
ttgctgagag cttgagagct gcagcggagg ctgctgtgtc gcagaccggc ttcacctacg   900
acgagagcac gggcttatat tttgaccaca gcactggttt ctattatgat tctgaaaacc   960
agctgtatta tgacccttcc acggggattt attactactg cgatgtggag agtggtcggt  1020
accagtttca ctctcgcgta gacctgcagc cttaccagac ctctagcaca aaaccaaaca  1080
gagaaagaag actgaagaag agaagaaagg agccaggttt ttatacagca aatgaagaaa  1140
aggatttgag ctcagaagat cagaaagtct gcagtgtaga atatataaac tgcagtgagg  1200
atgaacattc tggaaatgtg aaaaagaagg ccagaacaga cacttctcac aaaagcagtc  1260
ccttacagct cacggtggca gttagtggag acactgtgga gtctcctgga gatgataact  1320
cagcgtcatc taaggatgag agaatcggag agagtgagag cgagccggaa gaaggtgaga  1380
tcacagactc tcagagtgag aagagctatg atggagacag tagcagtggg gacagggaga  1440
cctcagaaga atccgacgat gaagatgagg aaagaatttg gccgccctgt attcgcgtga  1500
ttgtcattag gtctccagtg ttgcagatgg gctcgctgtt catcatcacc gctgtgagcc  1560
cagccaccat tgggagagag aaggacatgg agcatactgt gagaatccct gaagtcgctg  1620
ttagtaagtt ccacgcagaa gtttacttcg accatgactt gcaaagctac gttcttgtgg  1680
atcagggcag ccagaatggt accattgtca acgggaaaca gattcttcag ccaaaaacta  1740
aatgtgatcc ttacgtcctc gaacacggcg acgaagtgaa aattggggag actgtgctgt  1800
cttttcacat tcaccctggc agtgagacgt gcgatggctg tgagccgggg caggtcagag  1860
ctcacctccg cctcgataga aaggacgagc tctggtcgg tccagcacta agtaaggagg  1920
aaaaagagtt ggaaagaaga aaagcactca agaaaatacg agtaaagtat ggcttgcaga  1980
atacagatta tgaagctgaa aaagcgttga agaatcctaa gtataaagac agagctggaa  2040
aacgcaggga gcaggtggga agcgaaggga cttccaaaag agatgacgcc cctgcgtctg  2100
ttcactctga aattacagat agcaacaaag gccgaaagat gttggagaag atgggtgga  2160
aacggggaga aggcctggga aaggacgtg gagggatgaa aacgccgatc cagcttcagc  2220
ttcgacggac acatgctggc ttggggacag ggaagctgtc ctcgattgat gacgttcacc  2280
tcatccagaa taagagcaaa aaacactggg acaaagcccg ggagcggttt gcggaaactt  2340
tcacagaaaa caaacctcgg aaagagaccc caggggcagt gccgtgggtg acagggactg  2400
```

```
cagagtaaag gcctgtctgt cacacgggaa cttggagctt caaaagagaa agagtttgaa    2460
aacttcagtg tagaagctgt gttcctagaa agtcagtcac tggaggaact cttaagatgg    2520
ctacctgatc gacacatgtg tggggacatg tggtttgtag cttgtagaaa gcagttctta    2580
agtgggctca aggtgacagg cacaggagag ctgccagacc tttgttgttg tggcctgtca    2640
ctcaccctgt ggagagcagc tgaccatgtg agcagcgcac ataaccacta atgacttcag    2700
cgcgcgtgtc ctgtctctgt catcattacc atgacacaca gatatcagac atttataaaa    2760
caattctatg tgtatacttg tttacacctt ttagagctta ggttttttt ttaaaaagtc     2820 gagaaaccat gggtagtgga gcctaatttt actatccttg aaataactgc agtaataata    2880
gtgaagaatt gatgacaggt gacagattgt aggaaattag tctcacacta ttttcttctg    2940
tgaagaatgt tgtttgtact acagagtcag ctttgccttt ggtttgtcct agctgatgga    3000
gtatttcata tagacgactg agtgcagtgc tggcatattc agtatgctag cattttagt     3060 tttgataaat accattgcag gcaatgggac tgtgctcgag aaatctgatg actagggcag    3120
atgggttact aggccaaggc ttcaaacatt tactggaaat gtcttcaaat gcaataaaaa    3180
aaaacatttt t                                                         3191

<210> SEQ ID NO 4
<211> LENGTH: 711
<212> TYPE: PRT
<213> ORGANISM: Mus musculus

<400> SEQUENCE: 4

Met Ala Ser Glu Ala Pro Ser Pro Pro Ser Pro Ser Pro Pro Pro Pro
1               5                   10                  15

Ala Ser Pro Glu Pro Glu Leu Ala Gln Leu Arg Arg Lys Val Glu Lys
                20                  25                  30

Leu Glu Arg Glu Leu Arg Ser Cys Arg Arg Gln Val Arg Glu Val Glu
            35                  40                  45

Lys Leu Leu Gln His Thr Glu Arg Leu Tyr Arg Asn Ala Glu Ser Asp
        50                  55                  60

Asn Gln Glu Leu Arg Thr Gln Val Glu Glu Leu Ser Lys Ile Leu His
65                  70                  75                  80

Cys Gly Lys Asn Glu Asp Asn Pro Lys Ser Asp Val Glu Val Gln Thr
                85                  90                  95

Glu Ser Gln Ala Pro Trp Ala Ile Ser Asp Tyr Tyr Gln Thr Cys
                100                 105                 110

Tyr Asn Asp Asp Ser Leu Pro Ser Lys Glu Thr Glu Leu Cys Val Gln
            115                 120                 125

Gln Ser Gln Cys Ala Gln Ala Ser Ala Leu Asp Pro Gln Asp Glu Ser
        130                 135                 140

His Ile Asp Ser Gly Ser Tyr Ala Gly Ala Asp Ala Thr Glu Gly Val
145                 150                 155                 160

Ser His Arg Gln Glu Asp Ala Val Thr Ser Asp Ser Gln Glu Ser Val
                165                 170                 175

Ser Ala Leu Ala Glu Gly Pro Ala Leu Glu Gly Ser Ser Leu Ala Glu
            180                 185                 190

Ser Leu Arg Ala Ala Ala Glu Ala Ala Val Ser Gln Thr Gly Phe Thr
        195                 200                 205

Tyr Asp Glu Ser Thr Gly Leu Tyr Phe Asp His Ser Thr Gly Phe Tyr
    210                 215                 220

Tyr Asp Ser Glu Asn Gln Leu Tyr Tyr Asp Pro Ser Thr Gly Ile Tyr
225                 230                 235                 240
```

-continued

```
Tyr Tyr Cys Asp Val Glu Ser Gly Arg Tyr Gln Phe His Ser Arg Val
            245                 250                 255

Asp Leu Gln Pro Tyr Gln Thr Ser Ser Thr Lys Pro Asn Arg Glu Arg
            260                 265                 270

Arg Leu Lys Lys Arg Arg Lys Glu Pro Gly Phe Tyr Thr Ala Asn Glu
            275                 280                 285

Glu Lys Asp Leu Ser Ser Glu Asp Gln Lys Val Cys Ser Val Glu Tyr
            290                 295                 300

Ile Asn Cys Ser Glu Asp Glu His Ser Gly Asn Val Lys Lys Ala
305                 310                 315                 320

Arg Thr Asp Thr Ser His Lys Ser Ser Pro Leu Gln Leu Thr Val Ala
                    325                 330                 335

Val Ser Gly Asp Thr Val Glu Ser Pro Gly Asp Asn Ser Ala Ser
                    340                 345                 350

Ser Lys Asp Glu Arg Ile Gly Glu Ser Glu Ser Glu Pro Glu Glu Gly
                    355                 360                 365

Glu Ile Thr Asp Ser Gln Ser Glu Lys Ser Tyr Asp Gly Asp Ser Ser
            370                 375                 380

Ser Gly Asp Arg Glu Thr Ser Glu Glu Ser Asp Glu Asp Glu Glu
385                 390                 395                 400

Arg Ile Trp Pro Pro Cys Ile Arg Val Ile Val Ile Arg Ser Pro Val
                    405                 410                 415

Leu Gln Met Gly Ser Leu Phe Ile Ile Thr Ala Val Ser Pro Ala Thr
                    420                 425                 430

Ile Gly Arg Glu Lys Asp Met Glu His Thr Val Arg Ile Pro Glu Val
                    435                 440                 445

Ala Val Ser Lys Phe His Ala Glu Val Tyr Phe Asp His Asp Leu Gln
            450                 455                 460

Ser Tyr Val Leu Val Asp Gln Gly Ser Gln Asn Gly Thr Ile Val Asn
465                 470                 475                 480

Gly Lys Gln Ile Leu Gln Pro Lys Thr Lys Cys Asp Pro Tyr Val Leu
                    485                 490                 495

Glu His Gly Asp Glu Val Lys Ile Gly Glu Thr Val Leu Ser Phe His
                    500                 505                 510

Ile His Pro Gly Ser Glu Thr Cys Asp Gly Cys Glu Pro Gly Gln Val
            515                 520                 525

Arg Ala His Leu Arg Leu Asp Arg Lys Asp Glu Pro Leu Val Gly Pro
            530                 535                 540

Ala Leu Ser Lys Glu Glu Lys Glu Leu Glu Arg Arg Lys Ala Leu Lys
545                 550                 555                 560

Lys Ile Arg Val Lys Tyr Gly Leu Gln Asn Thr Asp Tyr Glu Ala Glu
                    565                 570                 575

Lys Ala Leu Lys Asn Pro Lys Tyr Lys Asp Arg Ala Gly Lys Arg Arg
            580                 585                 590

Glu Gln Val Gly Ser Glu Gly Thr Phe Gln Asp Asp Ala Pro Ala
            595                 600                 605

Ser Val His Ser Glu Ile Thr Asp Ser Asn Lys Gly Arg Lys Met Leu
610                 615                 620

Glu Lys Met Gly Trp Lys Arg Gly Glu Gly Leu Gly Lys Asp Gly Gly
625                 630                 635                 640

Gly Met Lys Thr Pro Ile Gln Leu Gln Leu Arg Arg Thr His Ala Gly
                    645                 650                 655

Leu Gly Thr Gly Lys Leu Ser Ser Ile Asp Asp Val His Leu Ile Gln
```

```
                  660                 665                 670
Asn Lys Ser Lys Lys His Trp Asp Lys Ala Arg Glu Arg Phe Ala Glu
            675                 680                 685

Thr Phe Thr Glu Asn Lys Pro Arg Lys Glu Thr Pro Gly Ala Val Pro
        690                 695                 700

Trp Val Thr Gly Thr Ala Glu
705                 710

<210> SEQ ID NO 5
<211> LENGTH: 21
<212> TYPE: RNA
<213> ORGANISM: Artificial Sequence
<220> FEATURE:
<223> OTHER INFORMATION: siRNA1

<400> SEQUENCE: 5
aauugucauu agaucacccg u                                              21

<210> SEQ ID NO 6
<211> LENGTH: 21
<212> TYPE: RNA
<213> ORGANISM: Artificial Sequence
<220> FEATURE:
<223> OTHER INFORMATION: siRNA2

<400> SEQUENCE: 6
aagaacaaaa aaaacuggga c                                              21

<210> SEQ ID NO 7
<211> LENGTH: 18
<212> TYPE: PRT
<213> ORGANISM: Artificial Sequence
<220> FEATURE:
<223> OTHER INFORMATION: synthetic peptide

<400> SEQUENCE: 7

Leu Ala Gln Leu Arg Arg Lys Val Glu Lys Leu Glu Arg Glu Leu Arg
  1               5                  10                  15

Ser Cys

<210> SEQ ID NO 8
<211> LENGTH: 8400
<212> TYPE: DNA
<213> ORGANISM: Homo sapiens

<400> SEQUENCE: 8
ggatcctccc atccttctgg tttgctttct ttagggtgtg gtgttcatct cacagtcagg      60
aagtggcttc tccaccttga gcataatgtc catctttcag gtaggagaaa gaagaagaaa     120
gagaagggca aaaacaaaag actgaatcta tcttttttaa acaggtgata cggtttggct     180
ctgtgtcccc acccaaatct tatcttgtag ttcccataat tcccacgtgt tgtgggaggg     240
acctggtggg agattattga atctgatcgt tttaaaaatg ggagttttcc tgcacggttt     300
ctctcttttg cctgctgacc tcatgtaagt atgtgacttg ctcctccttg cctcctccca     360
tgattgtgag gctttcccag ccacgtggaa ctgtaagtcc aattaaacct ctttctattg     420
taaattgccc agtctctgct atgtctttat cagcagtgag aaaacggact aatacaacag     480
gaaactacag cttttccaga aaccttgcct gtagtctact acttatacct cattggccaa     540
aactttgaca tatggtcacc tagctgcaaa caagagtgag aaatgtagac tttagctagg     600
tgtattgcta cccaaaacga aattcaggtt ctcttgtcag aaagaggaaa atatggctgt     660
```

```
tgggttgaca actagcagtg cctaccacaa aaacactttt taaaattgca gccagaaagg    720
gcttaactcc caggaacctt ggagactgtg agaaaatgaa ataatttaat attttgaaca    780
taattattta cagccccagg ctcatgttca ggttcaggct gagggcaaag atatgacctt    840
tgctcccacc agcaggcaat tagacatagg tgagcaaggg ctagcttgag tgattttttaa    900 agaactaggc aggcaccttc ctgcttatgc tgtaggatac ctgaaaggca ccagcaagca    960
acgaacaacc tcagaagaat ttaacaatga ttgctgattt ttgtatttgg tatccagttt   1020
taacactaaa aaattcctgt tggaatgggc cagttgcatt caaaaaagca cagttcaaat   1080
agccaaaaaa acttttttaaa ataaaaaatc caaactgact tggcatttct tgagaactat   1140
taaaagggca tcatttcgca ctgcccagta acccttctta catcccttat tctctcctct   1200
cccattcact cacgcatttt gttgtatctt acaaaaatat taatccataa tgaactagaa   1260 ttttttaaaaa catcctcacc acaaagagtt taagtactgc tctagtatga accattgatt   1320
ttgccttcta aagacctaga attggtccag tgggacagac tgtcctttga gagttcgaat   1380
tcttattatt aagggagagt agaagggagg aggacttggg aagattcgta acacagcaat   1440
gttttaactc attataccat cataaaagga aggtacaaaa tgtaagaatt ttagctgggg   1500
gtggagaata gtgtcttact tagcttcctc gggcttcctt taccatcact ccagtgtttt   1560
aatgttatat ccccccattt ttttcttggg cctccagggg aggaaacggg taatggtcaa   1620
ttgaccaaaa gtaacatggg gcaataaatc agaactattg aaatgctatg gttcccccag   1680
atattctcct gtggcatcaa aaagttgaat caggtaagga aaagttggct acccaccata   1740
tccaatataa attatgacag gtggatatta attaaatata aattgatgac actctaaaag   1800
aaattggaca taaatcagct tttattgaat tgacaatatt cttctgttgt ggaatattat   1860
aatatctcag gcatttgaac tccagcctga ttcaattcat aggctcctgg aatggctcta   1920
gatcagattg agtatcaatt agctattgct gcatactaaa caccccaaac ctcagtggct   1980
ttaaacaacc atccttcatt atttctcaca agcctagggg tgatgtgtgg gctggctgat   2040
caccaccacc aggcttgcta atgtgtctga gggtttcctg aagtctctgc tctagcctgg   2100
acttagctgg agcatctaag ctaggagagg tctgctccct gtattattca tctttctcct   2160
gagaccagca cacatgcctg ggtatgttct tcttgtggca atggcaggaa atccagaggg   2220
caagcagaat cactaaggcc ttgggactta ggcttagatg tgtcactctt ctggcacatc   2280
acatcattct gctgaccaaa gcaaatcaca tggccaaacc agctcaaagg tgaaggggag   2340
attcttccct tttagtgagg aaaaccacaa aatcacatgt caaaggatga ggaagaagac   2400
cgataaagaa ctggggccat tcatgcaatt tccaaagtgt gatggttaat tttatgtgtc   2460
agcttgattg ggccacaaga tgctcattta tctccttcaa tattatttct ggtgtgtgtg   2520
tgaggttgtt ccagaagac atttgaattg ccaaactagg taaagcagat ggccctcccc   2580
aatgtggatg ggaattctcc aacccactga cggcctgaat agaagaaaaa gacagagtag   2640
agttgaattc ttgctctgcc tgactgcttg agctggaaca ttgatcttct cctgcccttg   2700
gcactcctgg ttctcagacc ttcagactcg gattggaatc tataccattg gctccctggc   2760
tctcatgcct tcaaatgaca ccacgggctt tcctaggtat ccagcttgca gacaacagat   2820
tgtgggactt ctcagcctct ataatcactg agccaattcc ttatgataaa tcatatgaca   2880
gccaggcacg gtggctcaca cctacaatct cagcactttg ggaggccgag gcaggtggat   2940
tacctgaggt caggagtttg agaccagcct gaccaacatg gtgaaaccgt gtctctacta   3000
aaaatacaaa attaattggg tgtggtgaca ggtgcctgta atcccagcta ctcgggaggc   3060
```

-continued

```
tgaggtggga gaattatttg aacccgggag gccgaggttg cagtgagccg agatcacacc   3120
actgcattcc agcctgggag acagagcgag actccatctc aaaaaacaaa acaaaacaaa   3180
ataaatcata tgacactgaa gttacagaaa tcacttttct aatttgaatc atttttttaa   3240
aacagagaga tttcacataa aaatcctgat tgattttttt ttttcgaaaa atcagaagct   3300
ttgcaacaca gggtccacat tcccatatgt ctccacagtt cgcaggagct gagtagcagc   3360
tgccctgtcc attcatttgc tttatctccc tagcccttgg agccatttga gtttgcttta   3420
cacagtagta gttctacagc cagatctgtt tctcaagctt cagataggct tctgcagtgc   3480
tcactattta ctgaacacct caaattcaat ataattaaca atatcgaaac taaagcatcc   3540
cttcctcctc atgcaacata ctcttctcca atagtcccta tcttcctcat ccaagctaga   3600
aacctattca tcactttgac ttttctttcc ctctctaata tactacagta tacaattta   3660 ttcacaataa aactacggtg tgtctaggaa ataacctaag aaagaatacc caagaccttt   3720
cccgaaacaa gtgttaaaat tgtactaaag tccaagaaaa atattaagca aaaatgtatg   3780
tgaattgact atctaaataa agtttatgt taattcccct aaataaatct atacattcaa   3840
tgtaatctta ataaaaatcc cattggattg tttgaggaac tcaacgaact cattctaaaa   3900
tttatatgga aaaatagagg tttatgaata agctgatttt gaaaagaaaa aacaaaatag   3960
ggccttgccc taccagttaa ggcatactaa agaacctaag tgataaaaac agagtggctc   4020
tggcatggga gcagactaat agacaagtgg aaaagaatgg cgagctcaga actaggccat   4080
atataaagat gggaactgat ggaagatgat ggtggtacta caaagcaatg caaaggggat   4140
ggtcttgaga aaactaggtc atgtctgaat accccagct ggaatagaga acaaatgtga   4200
aagttcaaat tataagatca atagaagaaa atatgacttg gggtaaggaa agtcttcatg   4260
aaaccctaca ctgtaaagcc aaataaaatt ttaaaaagta aaataaaata aagactgatt   4320
tcatgacata caaattaaga actcctggct aacaaagaac actggacaaa gctaacaaat   4380
atatgacaaa ctgggagaag atatctgtaa tatctaaaac tgataaagaa ggaataccttt   4440 gtttatagaa taaagaactg caaaataaca agaaagaaat gggcaaaaag atatggatag   4500
gcaattcaca gaaaggaaag gacatatagc catttcaaca tatatacatt tcaacaaatg   4560
tatgagattc tctagtaatc agaggagtat caattaaaac agcaaggaaa tagctcatta   4620
tattcataat ggcaaaaagt acaaaaaatg gttcatatca tttattggag aggatgtggg   4680
aaaaaaacat tacaaaacaa aatcaaatcg tgaagggtgt caagtagaat gcttttttag   4740
ggcagcgcct ctgcccacta tgctaagtac ctcttagatc tgaaaactag gtgtggcaaa   4800
gactgctatt tacatactca acatgaattt tgcccttctt ccttacttgt agaacccta   4860 tattattagg agaataatgc gtctagctta gaaaaacaca catatacaca taattcccag   4920
ccccacttgc agcaagggt ggctattgat aggtagacag gaaccattga gtgggctt   4980 gggaaagtcc tttcatccct tgccattttg caccatggat cgacctggag gctctggaaa   5040
catgctccga gaatatgcag agcagaaaga cataccgagc ctgggtccct gaagaactgt   5100
ggagtcactg gccatggact gcccctctct aggcttctgt aatgtaacag gataacaccc   5160
taatttgttt aataagccac tatagaccac ctctgatact agcaccttaa tgcaattcct   5220
gatattcaag gcttttttcta aaaaaatgtc attctttttct aatggtcaga ggtaggatac   5280
agactggtac tacaaggtaa agataactta gccttgaaca gattaagaca aataagagga   5340
gcactgcttc aagtagcagt caataagctt atttattttt tctccagtta attactaaaa   5400
actgaaatat catcttaaag ataccttca aatggtattt atggaatttc ttatccccta   5460
```

```
aagaaaatag gtggagaaag tagaaaatag catcttttta aaaggacttc aatatgttca   5520
ttaatggagt cataatgcat caagggaagt cagaaatttt ttgcaataca tcttttttt    5580 tgcatcacgg gacataccat gtcttctcac taaacttcct ttgatggctt aaggttactc   5640
ttgacatgac aataaggtag aatctctatg tttccagata cagtgccttg tgaagaactc   5700
ttcaggccta aggaggaatg tgtacaggcc ctagagaggg caggtctctg ctggaaagct   5760
cactgtttat gaataatcta gtgggcagtg cacaagacaa aaatacatac agagccatat   5820
tttaaatttt agattttatt attatttatg tatggtgagg ccaacagatc aggagatggt   5880
ctgctatcaa aaagacagtt tattattcac ccagcccaag aggaggatgc acaccaagcc   5940
acacaaggca atgtggagaa gcaccaaggt ccaaggagg cagaaggagt gggaggaaac    6000
atggcaaaaa acattatgtg attttttgcag gaaggaatgg acaaatcagg ataagcaggt  6060
ttagtttgca taatttcagt gggatctgag atgtaggagt tgttcctagt tgtctggtac   6120
tttgccctgg agtgattagg gcaggggaat attggcatgg agtgtaacag cctgataaag   6180
aaggtagatg atcagtgtgt ggcatgctgg gtgagttgtt tgctatgtct aggaattagc   6240
taacccttgg aggggttatc tccctggtca gggagacccc agatgccaga gcatcaagaa   6300
tacaaaaaat aagaaaatat agttaatgga agtggccact gatctaagac accaaacagg   6360
attctcttgt tcagctgtgt tcagcattta cggatactgc tctgcgacag gcactgtgct   6420
gggccctgag agaggagcat ctgcatgaca cagctgctga cctccacaaa tctcaggccc   6480
aggactctga gctcatgatc taattctaaa tgactttggc aaaggaagga agtgtgttcc   6540
aaagaaggcc acatcagttt aaatactggc aaaccaatgc cagggtcatg cagacaaaag   6600
accaaataaa tgcaccaaac cagagcattt ttctccccctt ttccacagaa tattgtctct   6660
ctcttatttt cccaccaggg atgctccttt tgcgactca gacctaatgt acttgctcta    6720
ttttcccggg gggtctaaac tcaggaacca gaagaatgac taaatgagaa ataaagtaa    6780 aattctgagc ccctgaactg actgaataga cccattgttc actacataga aagccagtca   6840
ttgagacaag gagtattgcc agggaagaag gttctatttg ggtgctgcag ccaaggagaa   6900
taggaaatca gtctcaaatc catctcctca accaactaaa attagaggtt tatatggcaa   6960
gggagaaatg tgactacatg tgagaaaaca ggaattagtg agcggtaagg atgaggactt   7020
gttcaacagg cagcaggtgg ctggttaggc aatcatgatg ggtgagggt atggtgcctc    7080 attgtccaga tgcagtgatc tggtaagttt caattccttg atactatctg ggaggcctca   7140
tggttggttt cccaagaaag gaactcagat aagaaagatg taactttctg aagttttaag   7200
actgggaggg taaatttcca ggtttattca aaagaaacca taaacatcag ttctatagga   7260
cagttgggct gatttcacac caaccagcat tccttcctga taagagacca ccaaccacag   7320
agaagttctg gccaatctac cagggactca cagcgagggt tttcatgtcc tctgctttgc   7380
catttgacat cagagggctg aaaacttcac actgggatca tgctaacacc accattttt   7440 gaatatgggt cccatagaga ggcaggaagc ttaattgtgc atgtgcatat ttctcctttc   7500
ataaatattc atgaatcctc ctacagctca ttgaatatat ttggccaccc tgctcagcat   7560
aaatttctgt tccctttgtc cttccttcca agtgtctgtt ctcagcttct gaccagaggc   7620
tatgcttcca agcctgtcag aaaggccacc ctgcaggctg taacccttca tgagaaataa   7680 agccctttc taaatttatt aacctcctca ttcttcagtt gacataagta gagcatcata   7740
gtccccacaa atcatttctg ggatactctg ttccttatttg taaaacaagg agataggaaa  7800
tgcatgctat actaaaagtt tgttcaaaga acatccgcac gtgcaaatgt ctgagaccag   7860
```

| | | | | |
|---|---|---|---|---|
| aggctgcaag | cctccctgtc | gctcttaggg | cttcggtagc | cacattgcca | cagctctcca | 7920 |
| cgccctcagg | taacgcccct | ccgcaggccg | agacgtcggc | acgtacactg | tcaggtcttc | 7980 |
| ccgctttccg | tcgcttcctg | ttccgtcttg | gtcccgcctg | ccgctggcgc | cgttgtttcc | 8040 |
| ggctcaactg | gggagctgct | ggagctcttc | tggcctctgg | ttttccgact | gcttatccga | 8100 |
| cgctcctccc | tctgtctctg | tagctggaga | aggtagtttc | caggaaagtt | ttccggtttg | 8160 |
| caggccgcgc | acatcgggca | ggggccatcc | tcggtcccct | tgctcgttgc | tcgcagcccc | 8220 |
| gttcggctac | aagtgagttt | cagggcgtca | tggccagggg | ccaccgcggc | cagccgggtg | 8280 |
| tgaggctgcc | tttcgctgcc | cgcgcgctcc | agtggtctct | gggtccgccg | gcgtccgttt | 8340 |
| cggcctgaac | gcagcccctc | cgcggcgacg | agcagtctcg | cgccggagct | catggcctcg | 8400 |

```
<210> SEQ ID NO 9
<211> LENGTH: 21
<212> TYPE: DNA
<213> ORGANISM: Homo sapiens

<400> SEQUENCE: 9
aaactcagga agttgttaca a                                              21

<210> SEQ ID NO 10
<211> LENGTH: 24
<212> TYPE: DNA
<213> ORGANISM: Homo sapiens

<400> SEQUENCE: 10
ttcttctggt tcaaataatt ataa                                           24

<210> SEQ ID NO 11
<211> LENGTH: 4049
<212> TYPE: DNA
<213> ORGANISM: Homo sapiens
<220> FEATURE:
<221> NAME/KEY: misc_feature
<222> LOCATION: (3948)...(3948)
<223> OTHER INFORMATION: n is a, c, g, or t

<400> SEQUENCE: 11
```

| | | | | |
|---|---|---|---|---|
| gcttatccga | cgctcctccc | tctgtctctg | tagctggaga | aggtagtttc | caggaaagtt | 60 |
| ttccggtttg | caggccgcgc | acatcgggca | ggggccatcc | tcggtcccct | tgctcgttgc | 120 |
| tcgcagcccc | gttcggctac | aagtgagttt | cagggcgtca | tggccagggg | ccaccgcggc | 180 |
| cagccgggtg | tgaggctgcc | tttcgctgcc | cgcgcgctcc | agtggtctct | gggtccgccg | 240 |
| gcgtccgttt | cggcctgaac | gcagcccctc | cgcggcgacg | agcagtctcg | cgccggagct | 300 |
| catggcctcg | gaggcgccgt | ccccgccgcg | gtcgccgccg | ccgcccacct | ccccgagcc | 360 |
| tgagctggcc | cagctaaggc | ggaaggtgga | gaagttggaa | cgtgaactgc | ggagctgcaa | 420 |
| gcggcaggtg | cgggagatcg | agaagctgct | gcatcacaca | gaacggctgt | accagaacgc | 480 |
| agaaagcaac | aaccaggagc | tccgcacgca | ggtggaagaa | ctcagtaaaa | tactccaacg | 540 |
| tgggagaaat | gaagataata | aaaagtctga | tgtagaagta | caaacagaga | accatgctcc | 600 |
| ttggtcaatc | tcagattatt | tttatcagac | gtactacaat | gacgttagtc | ttccaaataa | 660 |
| agtgactgaa | ctgtcagatc | aacaagatca | agctatcgaa | acttctattt | tgaattctaa | 720 |
| agaccatttta | caagtagaaa | atgatgctta | ccctggtacc | gatagaacag | aaaatgttaa | 780 |
| atatagacaa | gtggaccatt | ttgcctcaaa | ttcacaggag | ccagcatctg | cattagcaac | 840 |
| agaagatacc | tccttagaag | gctcatcatt | agctgaaagt | ttgagagctg | cagcagaagc | 900 |

```
ggctgtatca cagactggat ttagttatga tgaaaatact ggactgtatt ttgaccacag    960
cactggtttc tattatgatt ctgaaaatca actctattat gatccttcca ctggaattta   1020
ttactattgt gatgtggaaa gtggtcgtta tcagtttcat tctcgagtag atttgcaacc   1080
ttatccgact tctagcacaa aacaaagtaa agataaaaaa ttgaagaaga aaagaaaaga   1140
tccagattct tctgcaacaa atgaggaaaa ggatttgaac tcagaggatc aaaaagcctt   1200
cagtgttgaa catacaagct gcaatgagga agaaaatttc gcaaatatga aaagaaggc    1260
caaaataggc attcatcaca aaaatagtcc ccccaaagtc actgttccaa ctagtggaaa   1320
tactatagag tctcctcttc atgaaaacat ctctaattca acatcattta agatgagaa    1380
aatcatggag actgatagtg aaccagagga aggtgaaatt acagactctc agactgagga   1440
tagttatgac gaagccatta ccagtgaagg caatgtaact gcagaagata gtgaggatga   1500
agatgaagac aaaatctggc ccccatgtat tagagtaatt gtcattagat cacccgtgtt   1560
gcagatagga tcactcttta tcattactgc tgtaaaccct gctacaattg gaagagaaaa   1620
ggatatggaa catactctcc gaatccctga agttggtgtc agtaagtttc atgcagaaat   1680
ttattttgac catgacttac aaagttatgt ccttgtggat caaggcagtc aaaatggcac   1740
aattgttaat ggaaaacaga ttcttcagcc gaaaactaaa tgtgaccctt acgtacttga   1800
gcatggagat gaagtcaaaa ttggagaaac tgtcttatcc tttcacattc atcctggcag   1860
tgatacctgt gatggctgtg aaccagggca ggttagagcc caccttcgcc ttgataagaa   1920
agatgaatct tttgttggtc caacactaag taaggaggaa aaagagttgg aaagaagaaa   1980
agaattaaag aaaatacgag taaaatatgg tttacagaat acagaatacg aagatgaaaa   2040
gacattgaag aatccaaaat ataaagatag agctggaaaa cgtagggagc aggttggaag   2100
tgaaggaact ttccaaagag atgatgctcc tgcatctgtt cattctgaaa ttactgatag   2160
caacaaaggt cggaagatgt tggagaagat gggttggaag aaaggagagg gcctggggaa   2220
ggatggtgga ggaatgaaaa cgccgatcca gcttcagctt cggcgaacac atgcaggctt   2280
ggggacaggc aaaccatcct catttgaaga tgttcacctt ctccaaaaca gaacaaaaa    2340
aaactgggac aaagcacgag agcggttac tgaaaacttc ccagaaacta gcctcaaaa     2400
agatgaccca gggaccatgc cttgggtaaa agggacttta gagtgaaggc taatcataga   2460
aaaaaaacct ctagttttt taaaaataga atttggaaac ttatttttc tccccaaaag     2520
aatcagcagc acaggggaac tatgtcacag tttacctctt cctgattcag aaatgtgtat   2580
ggtttgcagc ttttaaaaac catttttta aaactaataa atagtgactg aaccaattta    2640
tgcagtaaat agactaaagt tcacagggca cggatgagtt tatcaaactt cgttattta    2700
tcttcattta caacatccat ataagcaact agccatataa gcaaaattca tagaactact   2760
aatgacttaa gtgtacatct gttcttgtct ccatatattc atgtaagatg cacaacaaaa   2820
gaaacatcag aagtttataa aaataaatct gactatacgc atcctcattt attcccttta   2880
gaacctaggt aaaaaatgtt gcgaaaacat gggtagtggc gcatacatt tgttatcctt    2940
gaaatagcct aagtaatgtt attgaagaac taatgaacag gtaacatatt gtagaaaatt   3000
agtctttcat tgttttcttc tgtgaagaat ctgttgctat gtactgtata ttcagcattt   3060
atatttggtt tgtttcatag ctaatgaggt atttagatat gaacaactga atacatattg   3120
aaatagtgtg ctggcttttg tagttttgat aaagaccatt gcaggcaatg gaattgtgcc   3180
agagaaatct gatttctagt acaaaaggaa tacttagcca gggcctcaag ctcaagatac   3240
ttattgaaaa catcctcaat tgcaataaaa acattataac atgaaaaga gtgatttttt   3300
```

```
gaaccggtga tttaaatgta ttgatctgct ttgaattttc aagcagccag aattttctag    3360
tttaaattgg cagagttata acaaaggaga gcctcaaata ttagacaatt gcagtgcggc    3420
tttctgggca caggtgtcac tgctctgcca cctatcacta ttctttttct gttcagtttt    3480
tctctcaggt gtttgctggg gaaattaaca ctgggaactg acccttttct gggcagtgaa    3540
tgtaagctct agctccccca tctactataa agaaatgtct ttgagatgta gaaataagga    3600
atattctgaa aataaaaatt atacagtagt aaagataatt cagaaagaaa aagctacctg    3660
ttagaatttc cagtctaaat ggcacagggt agttacggag aaaaggggat ggagaaggag    3720
aaactatgac taaagatgag aggtatgaac gagttgtcag gttcctatgg gcttaagcta    3780
ggacaatcag gccctaaact ccaaatttgg ataaaatatc tctttgcatt cttcttggcc    3840
acctgcatag tctgacacat acgtatgtac agttagactt gcaggctgca ggagtgccct    3900
gcattgtttc ttttaattag aaaataaaag tattagtcta aatgtggntc ttgtgctggt    3960
gccctgtata tatgtaacaa tataggaccc cctccaaata ggttttgctt ctggtgaatc    4020
ttggtcattt ggttaagata tgactgtcc                                     4049
```

```
<210> SEQ ID NO 12
<211> LENGTH: 714
<212> TYPE: PRT
<213> ORGANISM: Homo sapiens

<400> SEQUENCE: 12
```

Met Ala Ser Glu Ala Pro Ser Pro Pro Arg Ser Pro Pro Pro Pro Thr
1               5                   10                  15

Ser Pro Glu Pro Glu Leu Ala Gln Leu Arg Arg Lys Val Glu Lys Leu
            20                  25                  30

Glu Arg Glu Leu Arg Ser Cys Lys Arg Gln Val Arg Glu Ile Glu Lys
        35                  40                  45

Leu Leu His His Thr Glu Arg Leu Tyr Gln Asn Ala Glu Ser Asn Asn
    50                  55                  60

Gln Glu Leu Arg Thr Gln Val Glu Glu Leu Ser Lys Ile Leu Gln Arg
65                  70                  75                  80

Gly Arg Asn Glu Asp Asn Lys Lys Ser Asp Val Glu Val Gln Thr Glu
                85                  90                  95

Asn His Ala Pro Trp Ser Ile Ser Asp Tyr Phe Tyr Gln Thr Tyr Tyr
            100                 105                 110

Asn Asp Val Ser Leu Pro Asn Lys Val Thr Glu Leu Ser Asp Gln Gln
        115                 120                 125

Asp Gln Ala Ile Lys Thr Ser Ile Leu Asn Ser Lys Asp His Leu Gln
    130                 135                 140

Val Glu Asn Asp Ala Tyr Pro Gly Thr Asp Arg Thr Glu Asn Val Lys
145                 150                 155                 160

Tyr Arg Gln Val Asp His Phe Ala Ser Asn Ser Gln Glu Pro Ala Ser
                165                 170                 175

Ala Leu Ala Thr Glu Asp Thr Ser Leu Glu Gly Ser Ser Leu Ala Glu
            180                 185                 190

Ser Leu Arg Ala Ala Ala Glu Ala Val Ser Gln Thr Gly Phe Ser
        195                 200                 205

Tyr Asp Glu Asn Thr Gly Leu Tyr Phe Asp His Ser Thr Gly Phe Tyr
    210                 215                 220

Tyr Asp Ser Glu Asn Gln Leu Tyr Tyr Asp Pro Ser Thr Gly Ile Tyr
225                 230                 235                 240

Tyr Tyr Cys Asp Val Glu Ser Gly Arg Tyr Gln Phe His Ser Arg Val

```
                      245                 250                 255
Asp Leu Gln Pro Tyr Pro Thr Ser Ser Thr Lys Gln Ser Lys Asp Lys
                260                 265                 270

Lys Leu Lys Lys Lys Arg Lys Asp Pro Asp Ser Ser Ala Thr Asn Glu
            275                 280                 285

Glu Lys Asp Leu Asn Ser Glu Asp Gln Lys Ala Phe Ser Val Glu His
        290                 295                 300

Thr Ser Cys Asn Glu Glu Asn Phe Ala Asn Met Lys Lys Lys Ala
305                 310                 315                 320

Lys Ile Gly Ile His His Lys Asn Ser Pro Pro Lys Val Thr Val Pro
                325                 330                 335

Thr Ser Gly Asn Thr Ile Glu Ser Pro Leu His Glu Asn Ile Ser Asn
            340                 345                 350

Ser Thr Ser Phe Lys Asp Glu Lys Ile Met Glu Thr Asp Ser Glu Pro
        355                 360                 365

Glu Glu Gly Glu Ile Thr Asp Ser Gln Thr Glu Asp Ser Tyr Asp Glu
    370                 375                 380

Ala Ile Thr Ser Glu Gly Asn Val Thr Ala Glu Asp Ser Glu Asp Glu
385                 390                 395                 400

Asp Glu Asp Lys Ile Trp Pro Pro Cys Ile Arg Val Ile Val Ile Arg
                405                 410                 415

Ser Pro Val Leu Gln Ile Gly Ser Leu Phe Ile Ile Thr Ala Val Asn
            420                 425                 430

Pro Ala Thr Ile Gly Arg Glu Lys Asp Met Glu His Thr Leu Arg Ile
        435                 440                 445

Pro Glu Val Gly Val Ser Lys Phe His Ala Glu Ile Tyr Phe Asp His
    450                 455                 460

Asp Leu Gln Ser Tyr Val Leu Val Asp Gln Gly Ser Gln Asn Gly Thr
465                 470                 475                 480

Ile Val Asn Gly Lys Gln Ile Leu Gln Pro Lys Thr Lys Cys Asp Pro
                485                 490                 495

Tyr Val Leu Glu His Gly Asp Glu Val Lys Ile Gly Glu Thr Val Leu
            500                 505                 510

Ser Phe His Ile His Pro Gly Ser Asp Thr Cys Asp Gly Cys Glu Pro
        515                 520                 525

Gly Gln Val Arg Ala His Leu Arg Leu Asp Lys Lys Asp Glu Ser Phe
    530                 535                 540

Val Gly Pro Thr Leu Ser Lys Glu Glu Lys Glu Leu Glu Arg Arg Lys
545                 550                 555                 560

Glu Leu Lys Lys Ile Arg Val Lys Tyr Gly Leu Gln Asn Thr Glu Tyr
                565                 570                 575

Glu Asp Glu Lys Thr Leu Lys Asn Pro Lys Tyr Lys Asp Arg Ala Gly
            580                 585                 590

Lys Arg Arg Glu Gln Val Gly Ser Glu Gly Thr Phe Gln Arg Asp Asp
        595                 600                 605

Ala Pro Ala Ser Val His Ser Glu Ile Thr Asp Ser Asn Lys Gly Arg
    610                 615                 620

Lys Met Leu Glu Lys Met Gly Trp Lys Lys Gly Glu Gly Leu Gly Lys
625                 630                 635                 640

Asp Gly Gly Gly Met Lys Thr Pro Ile Gln Leu Gln Leu Arg Arg Thr
                645                 650                 655

His Ala Gly Leu Gly Thr Gly Lys Pro Ser Ser Phe Glu Asp Val His
            660                 665                 670
```

```
Leu Leu Gln Asn Lys Asn Lys Lys Asn Trp Asp Lys Ala Arg Glu Arg
        675                 680                 685

Phe Thr Glu Asn Phe Pro Glu Thr Lys Pro Gln Lys Asp Asp Pro Gly
    690                 695                 700

Thr Met Pro Trp Val Lys Gly Thr Leu Glu
705                 710
```

```
<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
gaacgcagcc cctccgcggc gacga                                    25

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
ctggatgggg cgcggggctg aggag                                    25

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
gatttctttt tcctaaagcc ttgttt                                   26

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
gtgttagcat atcctcacta taagc                                    25

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
cacttcattt ttttgctaca gattat                                   26

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
cattttatta cctgtgaatt tgaggc                                   26
```

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gcttttgtct tatttggcat ga                                          22

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
tgacagaggg agactgtctc aa                                          22

<210> SEQ ID NO 21
<211> LENGTH: 27
<212> TYPE: DNA
<213> ORGANISM: Artificial Sequence
<220> FEATURE:
<223> OTHER INFORMATION: primer

<400> SEQUENCE: 21
tttatttttt tcttgacttt caaagga                                     27

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
ttgtaaagac attacctttt cc                                          22

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
ttaccagact gggctattta ctt                                         23

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
taagagtatt ctcccctgtt ccct                                        24

<210> SEQ ID NO 25
<211> LENGTH: 23
<212> TYPE: DNA
<213> ORGANISM: Artificial Sequence
<220> FEATURE:
<223> OTHER INFORMATION: primer

```
<400> SEQUENCE: 25
aagcctttct gaaataactg aaa                                              23

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
cctcctagtt atccctatga agttc                                            25

<210> SEQ ID NO 27
<211> LENGTH: 26
<212> TYPE: DNA
<213> ORGANISM: Artificial Sequence
<220> FEATURE:
<223> OTHER INFORMATION: primer

<400> SEQUENCE: 27
aatataaaaa attacatcta ggggac                                           26

<210> SEQ ID NO 28
<211> LENGTH: 26
<212> TYPE: DNA
<213> ORGANISM: Artificial Sequence
<220> FEATURE:
<223> OTHER INFORMATION: primer

<400> SEQUENCE: 28
ttaaagacac tttacttaac tctgca                                           26

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
aacacatata cactcacctg aagaa                                            25

<210> SEQ ID NO 30
<211> LENGTH: 27
<212> TYPE: DNA
<213> ORGANISM: Artificial Sequence
<220> FEATURE:
<223> OTHER INFORMATION: primer

<400> SEQUENCE: 30
gcttgatttc actttctaag tttcatg                                          27

<210> SEQ ID NO 31
<211> LENGTH: 23
<212> TYPE: DNA
<213> ORGANISM: Artificial Sequence
<220> FEATURE:
<223> OTHER INFORMATION: primer

<400> SEQUENCE: 31
tgtaaaatgt ttcccctcta gcc                                              23

<210> SEQ ID NO 32
<211> LENGTH: 25
```

```
<212> TYPE: DNA
<213> ORGANISM: Artificial Sequence
<220> FEATURE:
<223> OTHER INFORMATION: primer

<400> SEQUENCE: 32
ccacatttaa tctgtttcac atacc                                              25

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
atacagctta acaaatgaaa caata                                              25

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
gaaaggacat catcacaacc caata                                              25

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
aaggatgttt cgagccactg ta                                                 22

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
gtttatagag gccacattga atcat                                              25

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37
cacggtaaat gtctgctcta ggaataa                                            27

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
gttaggtaat gccaagcggt tttct                                              25
```

<210> SEQ ID NO 39
<211> LENGTH: 26
<212> TYPE: DNA
<213> ORGANISM: Artificial Sequence
<220> FEATURE:
<223> OTHER INFORMATION: primer

<400> SEQUENCE: 39
atagttcccc tgtgctgctg attctt        26

<210> SEQ ID NO 40
<211> LENGTH: 25
<212> TYPE: DNA
<213> ORGANISM: Artificial Sequence
<220> FEATURE:
<223> OTHER INFORMATION: primer

<400> SEQUENCE: 40
ctctaaaata agtcctctgc tcaac         25

<210> SEQ ID NO 41
<211> LENGTH: 24
<212> TYPE: DNA
<213> ORGANISM: Artificial Sequence
<220> FEATURE:
<223> OTHER INFORMATION: primer

<400> SEQUENCE: 41
tgtttaaatg ccagtgtttt gtag          24

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
gacaggttct tgggcatcaa c             21

<210> SEQ ID NO 43
<211> LENGTH: 34
<212> TYPE: DNA
<213> ORGANISM: Artificial Sequence
<220> FEATURE:
<223> OTHER INFORMATION: primer

<400> SEQUENCE: 43
gggtaccgaa ttcgtcccca agcctgcatg tgtt        34

<210> SEQ ID NO 44
<211> LENGTH: 36
<212> TYPE: DNA
<213> ORGANISM: Artificial Sequence
<220> FEATURE:
<223> OTHER INFORMATION: primer

<400> SEQUENCE: 44
cgggatcccg tctagacgta cttgagcatg gagatg      36

<210> SEQ ID NO 45
<211> LENGTH: 20
<212> TYPE: DNA
<213> ORGANISM: Artificial Sequence
<220> FEATURE:
<223> OTHER INFORMATION: primer

```
<400> SEQUENCE: 45
cgtgcacatg agctggctac                                                    20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gccagatctt gatgcccaac                                                    20

<210> SEQ ID NO 47
<211> LENGTH: 19
<212> TYPE: RNA
<213> ORGANISM: Artificial Sequence
<220> FEATURE:
<223> OTHER INFORMATION: siRNA scramble duplex

<400> SEQUENCE: 47
gcgcgcuuug uaggauucg                                                     19

<210> SEQ ID NO 48
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 48
atcacaaaaa tagtcccc                                                      18

<210> SEQ ID NO 49
<211> LENGTH: 21
<212> TYPE: PRT
<213> ORGANISM: Homo sapiens

<400> SEQUENCE: 49

Cys Glu Tyr Glu Asp Glu Lys Thr Leu Lys Asn Pro Lys Tyr Lys Asp
 1               5                  10                  15

Arg Ala Gly Lys Arg
            20

<210> SEQ ID NO 50
<211> LENGTH: 18
<212> TYPE: PRT
<213> ORGANISM: Mus musculus

<400> SEQUENCE: 50

Cys His Ser Gly Asn Val Lys Lys Ala Arg Thr Asp Thr Ser His
 1               5                  10                  15

Lys Ser

<210> SEQ ID NO 51
<211> LENGTH: 16
<212> TYPE: PRT
<213> ORGANISM: Mus musculus

<400> SEQUENCE: 51

Cys Leu Ile Gln Asn Lys Ser Lys Lys His Trp Asp Lys Ala Arg Glu
 1               5                  10                  15
```

GENE AND PROTEIN ASSOCIATED WITH ANGIOGENESIS AND ENDOTHELIAL CELL-SPECIFIC APOPTOSIS

This application is the U.S. National Stage of International Application No. PCT/US2004/027324, filed Aug. 20, 2004, published in English, which claims priority under 35 U.S.C. §119(e) to U.S. Provisional Application Ser. No. 60/496,879 filed Aug. 20, 2003 which is incorporated by reference herein its entirety.

REFERENCE TO GOVERNMENT SUPPORT

This invention was made with government support under grant R01 HL65630 awarded by the National Institutes of Health. The U.S. government may have certain rights in this invention.

FIELD OF THE INVENTION

The present invention generally relates to angiogenic growth factors and endothelial cell apoptotic factors and to methods of using such factors or their inhibitors in the diagnosis and treatment of angiogenesis-mediated diseases or disorders

BACKGROUND OF THE INVENTION

Various publications or patents are referred to throughout this application to describe the state of the art to which the present invention pertains. Each of these publications or patents is incorporated by reference herein.

Angiogenesis, simply defined as the growth of new blood vessels, is an important natural process occurring in the body, both in health and in disease. Angiogenesis is controlled through a series of "on" and "off" switches. The main "on" switches are known as angiogenesis-stimulating growth factors and the main "off" switches are known as angiogenesis inhibitors. When angiogenic growth factors are produced in excess of angiogenesis inhibitors, the balance is tipped in favor of blood vessel growth. When inhibitors are present in excess of stimulators, angiogenesis is stopped. The normal healthy body maintains a balance of angiogenesis modulators (Risau, W., Nature 1997, 386: 671-74) The process of angiogenesis follows an orderly sequence of events. Diseased or injured tissues produce and release angiogenic growth factors, which are proteins or polypeptides that participate in the process of new blood vessel formation. The angiogenic growth factors bind to specific receptors located on the endothelial cells nearby preexisting blood vessels. Once growth factors bind to their receptors, the endothelial cells become activated. Signals are sent from the cell's surface to the nucleus. The endothelial cell's machinery begins to produce new molecules and enzymes. The enzymes dissolve tiny holes in the sheath-like covering (basement membrane) surrounding all existing blood vessels and the endothelial cells begin to proliferate, as they migrate out through the dissolved holes of the existing vessel towards the diseased tissue. Specialized molecules, called adhesion molecules or integrins serve as grappling hooks to help pull the sprouting new blood vessel forward. Matrix metalloproteinases are produced to dissolve the tissue in front of the sprouting vessel tip in order to accommodate it. As the vessel extends, the tissue is remolded around the vessel. Sprouting endothelial cells roll up to form blood vessel tube and individual blood vessel tubes connect to form blood vessel loops that can circulate blood. Finally, newly formed blood vessel tubes are stabilized by pericytes, specialized smooth muscle cells that provide structural support. Blood flow then begins.

In the healthy body, angiogenesis may occur to heal wounds or to restore blood flow to tissues after injury or insult. In females, angiogenesis occurs during the monthly reproductive cycle, to rebuild the uterus lining or to mature the egg during ovulation, and during pregnancy, to build the placenta, the circulation between mother and fetus. In many serious disease states, however, the body loses control over angiogenesis. Angiogenesis-dependent diseases result when new blood vessels either grow excessively or insufficiently. Excessive angiogenesis occurs in diseases such as cancer, diabetic blindness, age-related macular degeneration, rheumatoid arthritis, and psoriasis, and more than 70 other conditions. In these conditions, new blood vessels feed diseased tissue, destroy normal tissues, and in the case of cancer, the new vessels nourish tumor cells with oxygen and nutrients and allow tumor cells to escape into the circulation and lodge in other organs. Angiogenesis contributes to both the invasiveness of tumor cells and to their ability to metastasize to distant sites, the two major causes of the lethality of cancer, which kills over half a million patients each year in the United States.

On the other hand, insufficient angiogenesis occurs in diseases such as coronary artery disease, stroke, and delayed wound healing. In these conditions, inadequate blood vessels grow and circulation is not properly restored, leading to the risk of tissue death. Promotion of angiogenesis in wound healing would aid in the healing of broken bones, burns, diabetic ulcers, or traumatic or surgical wounds, and organ transplantation. Pro-angiogenic drugs may also be used to treat peripheral vascular disease, cerebral vascular disease, hypoxic tissue damage, or coronary vascular disease as well as to treat patients who have or have had transient ischemic attacks, vascular graft surgery, balloon angioplasty, frostbite, gangrene, or poor circulation.

Because dysregulated angiogenesis is the root cause of the pathophysiology of a significant number of diseases, identifying the factors responsible for the up- or downregulation of angiogenesis and designing strategies to modulate their activity has become an urgent clinical priority. As such, the identification of a novel potent angiogenic stimulator and the ability to modulate its activity thus represent a major advance in the art of pro-angiogenic therapeutics. Likewise, the identification of a novel potent angiogenic regulator capable of specifically inducing endothelial cell apoptosis and the ability to modulate its activity thus represent a major advance in the art of anti-angiogenic therapeutics.

SUMMARY OF THE INVENTION

The present invention provides a novel potent angiogenic factor, VG5Q, which plays a critical role in vascular morphogenesis and angiogenesis. VG5Q protein is expressed in endothelial cells and localized in and around the nucleus. During the formation of endothelial tubes VG5Q undergoes dramatic redistribution by moving to the cell surface and bridging extracellularly to neighboring endothelial cells. The present invention demonstrates that suppression of endothelial VG5Q expression inhibits endothelial tube formation (angiogenesis), thus making VG5Q a prime target for anti-angiogenic approaches. Furthermore, the present invention shows that suppression of VG5Q leads to selective apoptosis of endothelial cells.

Accordingly, the present invention provides isolated nucleic acid and amino acid sequences encoding a novel angiogenic growth factor protein VG5Q, which protein has pro-angiogenic activity, a forkhead-associated domain, a G-patch domain, characteristic subcellular localization in an in vitro Matrigel model of angiogenesis: towards the cell periphery in early stages of tubulogenesis, between cells in newly formed endothelial tubes, and no nuclear staining after 24 hours, expressed in endothelial cells, secretion during angiogenesis, and interaction with TWEAK. The invention also includes expression vectors containing nucleic acid sequences encoding VG5Q, host cells containing one or more expression vectors for the recombinant expression of VG5Q, therapeutic compositions and methods for the diagnosis and/or treatment of angiogenesis-mediated diseases.

The isolated nucleic acid sequences encoding VG5Q include, but are not limited to, the cDNA sequences identified in SEQ ID NO:1 (Genbank AY500994, human full length VG5Q cDNA) and SEQ ID NO:3 (Genbank AAY500995, mouse full length VG5Q cDNA), the t(5;11)(q13.3;p15.1) translocation sequences in SEQ ID NO: 9, (Derivative chromosome 5 in KTS, sequence flanking breakpoint), and SEQ ID NO: 10 (Derivative chromosome 11 in KTS, sequence flanking breakpoint), the E133K mutant DNA sequence in SEQ ID NO: 11, nucleic acid sequences that code for the VG5Q protein amino acid sequences in SEQ ID NO:2 (Genbank AAR97615.1, human VG5Q protein sequence), SEQ ID NO:4 (Genbank AAR97616.1, mouse VG5Q protein sequence), and SEQ ID NO: 12 (VG5Q E133K mutant protein sequence), as well as nucleic acids with 95% identity to these sequences, or that hybridize under high stringency, and any subsequences or fragments thereof. A nucleic acid molecule of the present invention can include only a portion of the nucleic acid sequences of SEQ ID NO:1, SEQ ID NO:3, SEQ ID NO: 8 (human VG5Q promoter region), or SEQ ID NO: 11. For example, such a nucleic acid molecule can be a single stranded oligonucleotide which can be used as a probe or primer, an antisense or RNAi agent, or which encodes a fragment of an amino acid sequence provided by the present invention. Nucleic acid fragments should not to be construed as encompassing those fragments that may have been disclosed prior to the invention. The present invention specifically provides probes and primers for all exons of VG5Q, such as those disclosed in SEQ ID NOs 13-46. These primers are highly useful for the diagnosis of known mutations in VG5Q, such as the E133K missense mutation that leads to KTS, as well as for the detection of other mutations.

The present invention also provides amino acid sequences for the VG5Q protein, as identified in SEQ ID NO:2 and SEQ ID NO:4, and includes proteins with a 90% amino acid sequence identity to SEQ ID NO:2 and SEQ ID NO:4, and peptide fragments thereof. The VG5Q protein and its peptide fragments and analogs thereof, are useful as immunogens for producing anti-VG5Q antibodies, or in therapeutic composition containing such proteins and/or anti-VG5Q antibodies. Anti-VG5Q antibodies provided by the present invention include those which bind to VG5Q and disrupt its function in endothelial tube formation and stability. Exemplary immunogenic VG5Q protein sequences are identified in SEQ ID NO:7, SEQ ID NO:49, SEQ ID NO:50, and SEQ ID NO:51.

The invention also includes peptide fragments and analogs of VG5Q protein sequence. "Peptide fragment" refers to a fragment of a VG5Q protein having sufficient length to be angiogenic and/or immunogenic, such as the functional and structural domains set forth above (pro-angiogenic activity, a forkhead-associated domain, a G-patch domain, characteristic subcellular localization in an in vitro Matrigel model of angiogenesis: towards the cell periphery in early stages of tubulogenesis, between cells in newly formed endothelial tubes, and no nuclear staining after 24 hours, expressed in endothelial cells, secretion during angiogenesis, and interaction with TWEAK), and peptide analogs include those variants of VG5Q protein or peptide fragments of VG5Q having substitutions, insertions, or deletions of one or more amino acid residues or having modifications on the side groups of amino acid residues and which maintain the function of the complete VG5Q protein.

The invention also provides various therapeutic compositions comprising an effective amount of VG5Q protein and a pharmaceutically acceptable carrier, as well as methods for treating diseases or disorders characterized by insufficient or excessive angiogenesis in a subject by administering the composition to the subject.

The present invention also provides methods for determining VG5Q binding partners and includes the isolation of the VG5Q cell-surface receptor. The VG5Q proteins of the present invention may be labeled with other molecules or proteins for use in the detection and visualization of VG5Q binding partners with techniques that are well known in the art, including, but not limited to, two-hybrid screens, expression cloning, phage display, coprecipitation, proteomics approaches, flow cytometry, radioreceptor binding assays, and immunohistochemistry. The VG5Q binding partner TWEAK has been identified.

The present invention also provides anti-VG5Q antibodies, which comprise antibodies specific for VG5Q proteins and portions thereof, and antibodies that inhibit the binding of antibodies specific for VG5Q. These antibodies may be polyclonal or monoclonal and may be used therapeutically (as VG5Q inhibitors) or in diagnostic kits to detect the presence and/or quantity of VG5Q which is diagnostic or prognostic for the occurrence of diseases mediated by angiogenesis.

Accordingly, the present invention includes diagnostic methods and kits for the detection and measurement of VG5Q in biological fluids and tissue and for the localization of VG5Q in tissues and cells. The diagnostic methods and kits may be used in any configuration well known to those of ordinary skill in the art.

The invention further provides therapeutic compositions comprising an effective amount of anti-VG5Q antibody and a pharmaceutically acceptable carrier, as well as methods for treating diseases or disorders characterized by excessive angiogenesis in a subject by administering the composition to the subject.

The invention also provides for anti-sense nucleic acid sequences and RNAi sequences (siRNA and hRNA), such as the exemplary sequences provided in SEQ ID NO:5 (siRNA1) and SEQ ID NO:6 (siRNA2), which inhibit the production of VG5Q protein by interfering with the stability of VG5Q mRNA and/or translation of mRNA into the VG5Q protein. These RNAi nucleic acids can be designed to be specific to human VG5Q protein, mouse VG5Q protein, or can be designed to work in both species. SEQ ID NO: 5 and SEQ ID NO: 6 are specific for the human VG5Q sequence.

Accordingly, the invention provides for additional therapeutic compositions comprising an effective amount of siRNA, hRNA, or anti-sense nucleic acid sequences and a pharmaceutically acceptable carrier, as well as methods for treating diseases or disorders characterized by excessive angiogenesis in a subject by administering the composition to the subject.

The present invention further encompasses gene therapy methods whereby nucleic acid sequences are introduced into a subject to modulate in vivo VG5Q levels. The nucleic acid sequence may comprise the sequence for VG5Q to enhance cellular expression of the VG5Q. The nucleic acid sequence may also comprise anti-sense, siRNA sequences, or hRNA sequences or DNA sequences encoding siRNA or hRNA sequences to suppress and/or inhibit the cellular expression of VG5Q. The gene therapy methods of the present invention may be performed through techniques well-known to one of ordinary skill in the art. The nucleic acid delivery vehicles comprise a nucleic acid sequence coding for VG5Q in a nucleic acid carrier. The nucleic acid carrier may be a vector, a lipid, a gene gun, or any suitable carrier known in the art.

In a further aspect, the invention encompasses methods of promoting or blocking VG5Q mediated angiogenesis in combination with other therapies to treat disease. Non-limiting examples of promoting angiogenesis in combination with other angiogenic growth factors include administration of VG5Q in combination with TWEAK, VEGF, Angiopoietins, PDGF, and FGF. Conversely, targeting multiple biological pathways as a strategy to improve cancer treatment may be advantageous as most advanced malignant tumors produce multiple growth factors. Thus, by targeting biological agents with, for example, angiogenic growth factor inhibitors, in combination therapy with conventional treatments such as chemotherapy or radiation it may be possible to reduce the dose and frequency of administration of both types of therapy (O'Reilly M S, Clinical Cancer Research 2002, 8: 3309-10). Some non-limiting examples for blocking angiogenesis include the use of siRNA against VG5Q with another antiangiogenic agent to produce synergistic effects to significantly minimize tumor resistance and tumor growth rate (Filleur S, et al., Cancer Research 2003, 63: 3919-3922), with si RNA to suppress expression of oncogenic mutations that arise in cancers (Martinez L A, et al., PNAS 2002, 99:14849-54) or with siRNA against $alpha_6$ $beta_4$ integrin to inhibit integrin mediated invasion and migration of breast carcinoma (Lipscomb E A, et al., Clin Exp Metastasis. 2003, 20(6):569-76).

In a further aspect, the invention provides novel promoters, ordinarily associated with the gene encoding VG5Q, including a wil-type (regulated) promoter, and a mutant (dysregulated) form of the promoter.

BRIEF DESCRIPTION OF THE DRAWINGS

FIG. 2 depicts the positional cloning of VG5Q. FIG. 2(a) shows the fine localization of the 5q13.3 breakpoint within the physical map consisting of bacterial artificial chromosomes (BACs). The (+) and (−) symbols indicate results of sequenced tagged sites (STS) amplification from the somatic cell hybrids der 5 (containing the derivative chromosome 5) or der 11 (containing the derivative chromosome 11). The thick vertical line indicates the 5q translocation breakpoint. A novel gene, VG5Q, was identified by gene/EST database searches with DNA sequences derived from BAC 18o21. The 11p15/1 breakpoint was initially localized into a region flanked by markers D11S915 and D11S4665 (on single YAC 814g10 or 773d6), and later defined between a small 1 kb region (data not shown). FIG. 2(b) depicts the definition of chromosome breakpoints involved in translocation t(5;11) (q13.3;q15.1). Sequence comparison between the normal chromosomes 5 (Chr. 5) and 11 (Chr. 11) and that derived from the derivative chromosomes 5 (der 5) and 11 (der 11) revealed the precise breakpoints involved in translocation t(5;11). FIG. 2 (c) shows the amino acid sequences of human VG5Q. The forkhead associated FHA domain (amino acids 435-508) and G-patch domain (amino acids 619-663) are indicated.

FIG. 3 depicts the cDNA and amino acid sequences of human VG5Q. The coding region is from nucleotide 302 to 2443, and the translated amino acid sequence is shown under the cDNA sequence. The deduced polyadenylation signals are underlined. The nuclear localization signal (amino acids 271-278), a forkhead associated (FHA) domain (amino acids 435-508) and a G-patch domain (amino acids 619-663) are indicated with boxes.

FIG. 4 shows that VG5Q mutations cause KTS. FIG. 4 (c)-(e) shows the statistically significant association between VG5Q mutation E133K identified in five independent patients with KTS but not in 200 controls.

FIG. 5 depicts the distinct expression of VG5Q in the vascular system and dynamic redistribution and secretion of VG5Q protein during angiogenesis. FIG. 5 (d) shows the expression of VG5Q in different cell lines determined by RT-PCR. Tubulin is the internal control. FIG. 5 (e) depicts the results of a competitive ELISA analysis to show that VG5Q is secreted during angiogenesis. Control buffer—PBS, blank media— media without cells, no angiogenesis—media from cells cultured on plastic dishes; angiogenesis—media from cells plated on matrigel for 4 hours. Relative HRP activity—absorbance reading of the wells subtracted with background reading.

FIG. 7(a) RT-PCR and Western blot analysis for VG5Q expression under normal and inhibiting conditions. Endothelial cells (EC) and fibroblast cells (FC) were transfected with VG5Q-specific (+siRNA) or without (−siRNA) siRNA. RNA was isolated and used for RT-PCR analysis using standard procedures. The PCR primers for VG5Q are P9: 5'-GGG TAC CGA ATT CGT CCC CAA GCC TGC ATG TGT T-3' (SEQ ID NO: 43) and P6: 5'-CGG GAT CCC GTC TAG ACG TAC TTG AGC ATG GAG ATG-3' (SEQ ID NO: 44). The PCR primers for ribosomal protein are 5'-CGT GCA CAT GAG CTG GCT AC-3' (SEQ ID NO: 45) and GCC AGA TCT TGA TGC CCA AC-3' (SEQ ID NO: 46). For Western blot analysis, cell extract was fractionated through 7.5% SDS-PAGE, transferred to nitrocellulose membrane, and probed with the anti-VG5Q antibody or the anti-tubulin antibody. The expression level VG5Q was calibrated by the corresponding tubulin value from the corresponding lane, as shown in the graphs. Note that there are two protein bands recognized the anti-VG5Q antibody in fibroblast cells, and the lower band is identical to the VG5Q band in EC. The nature of the upper protein band is unknown. FIG. 7(b) shows that suppression of VG5Q expression triggers endothelial cell apoptosis. Apoptotic cells were detected using a flow cytometry method that detects DNA breaks labeled by fluorescein anti-BrdU antibody. An increased number of apoptotic cells was observed following 48 hours of transfection with siRNA in endothelial cells (EC) but not in vascular smooth muscle (VSMC), human embryonic kidney (HEK) and fibroblast cells (FC). Transfection of endothelial cells with scramble duplex did not increase apoptotic cells. Exposure of endothelial cells to an anti-sense oligonucleotide against VG5Q (+ anti-sense) for 48 hours induced apoptosis, but not the sense oligonucleotide (+ sense).

FIGS. 8a-c depict endothelial cells (EC) transfected with siRNA against VG5Q (b,c), and scramble duplex (a) on plastic Petri dishes. The adherent cells were covered from the plates at 48 hours of transfection and plated on matrigel-coated plates. Note the abnormal tube formation by endothelial cells exposed to siRNA (b, c) as compared to cells exposed to the negative control scramble duplex (a). Endothelial tube formation was not affected when cells were exposed to scramble duplex (a). FIG. 8d is a graph showing VG5Q RNA expression in endothelial cells treated with siRNA1. FIG. 8e is a graph showing VG5Q protein expression in endothelial cells treated with siRNA1.

FIG. 10 (a) depicts the results of Pull-down assays using GST-TWEAK. Input, $^{35}$S-labelled luciferase (Luc, about 61 kDa) and VG5Q (about 84 kDa). Right panel shows binding of VG5Q with GST-TWEAK, but not with GST alone; middle panel, no interaction between GST-TWEAK with luciferase. FIG. 10 (b) depicts the co-immunoprecipitation of TWEAK with VG5Q from HVSMC protein extract by a rabbit anti-VG5Q antibody. Bound materials were analysed by western blot using a goat anti-TWEAK antibody. NRS, normal rabbit serum as a negative control. The 50-kDa band results from IgG cross-reaction.

DETAILED DESCRIPTION

Figure 1:
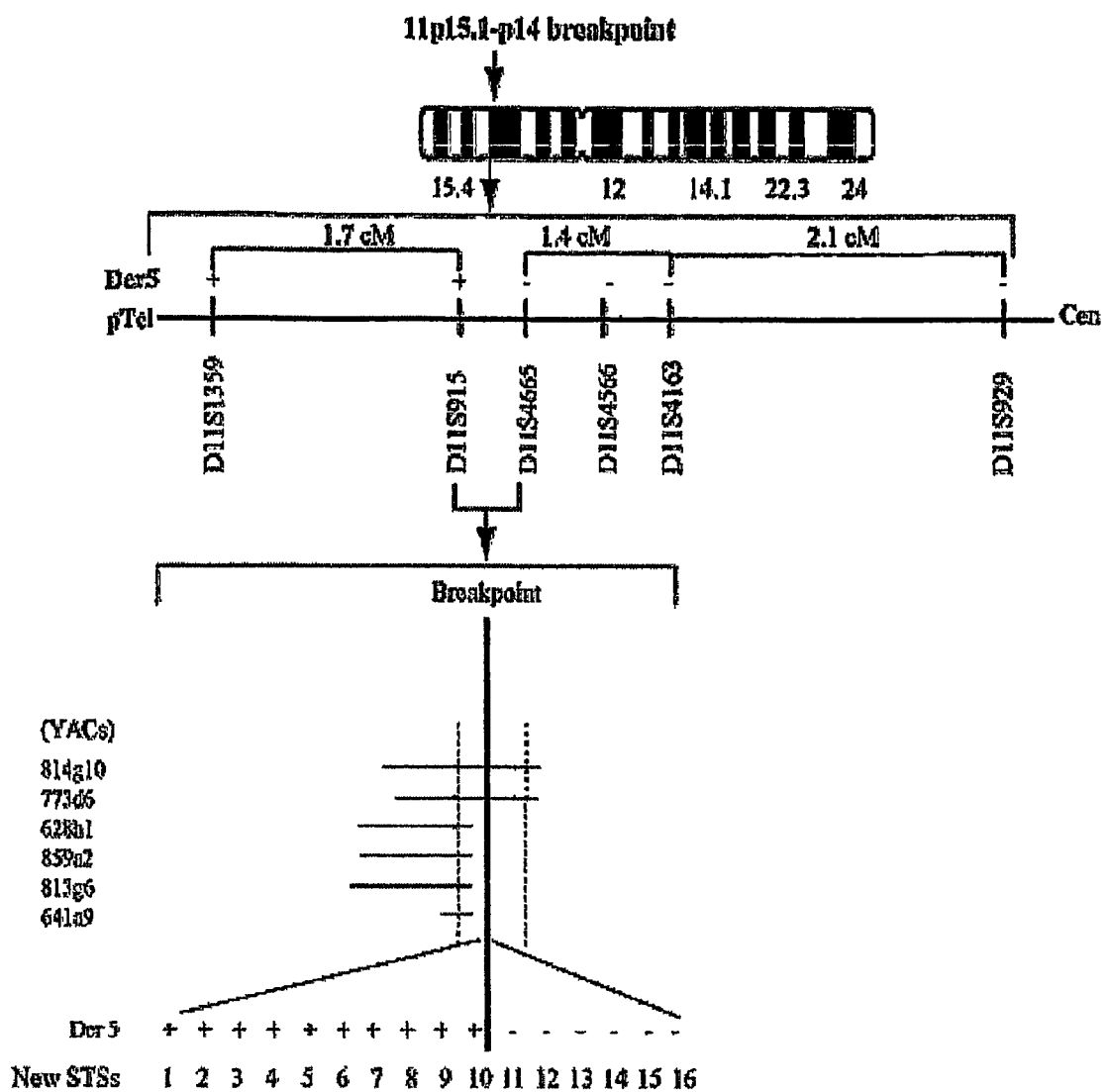
FIG. 1 shows the fine localization of the 11p15.1 breakpoint. This breakpoint (shown as a thick vertical line) was initially localized into a region flanked by markers D11S915 and D11S4665, which are on single yeast artificial chromosome (YAC) 814g10 or 773d6 (size 820 kb). Further STS analysis with the derivative chromosome 5 (der 5) hybrid defined the chromosome 11p15.1 breakpoint between STSs 10 and 11, a small region about 1 kb. The (+) and (−) symbols indicate results of STS amplification from the somatic cell hybrids der 5 (presence or absence, respectively).

The present invention advantageously provides a new angiogenic factor, VG5Q. As discussed below, this angiogenic factor has structural features, such as a forkhead-associated domain, a G-patch domain, and sequence characteristics that differentiate it from other angiogenic factors. It also has identifying functional characteristics. This protein potently induces angiogenesis that is highly specific for endothelial cells. The VG5Q protein, nucleic acids, and antibodies provide new and powerful tools for regulating angiogenesis. Angiogenesis plays an essential role in pathologic conditions such as tumor growth and metastasis and various ischemic and inflammatory diseases. Angiogenic factors are critical to the initiation and promotion of angiogenesis and to the maintenance of the vascular network. Modulating angiogenesis is thus a therapeutic goal of foremost importance in the clinical management of a large number of diseases. A variety of therapies targeting the regulation of previously identified angiogenic factors are currently in clinical trials and are already yielding encouraging results. This invention concerns a new target for the control of angiogenesis endothelial cells.

Accordingly, the present invention provides a novel potent regulator of angiogenesis and endothelial cell apoptotic factor, VG5Q. The gene coding for VG5Q was identified in course of a search for the susceptibility gene for Klippel-Trenaunay Syndrome (KTS). KTS is a congenital vascular disease characterized by a combination of capillary malformations (usually port-wine stains), soft tissue or bony hypertrophy (or both); and varicose veins or venous malformations, often with persistent embryologic veins. The disease affects many parts of the body, and is associated with a significant morbidity with a profound impact on a patients life (e.g. pain, disability, disfigurement, and social stress). KTS is commonly sporadic and its etiology is unknown.

Because of the vascular involvement in KTS, it seemed possible that a genetic defect in an angiogenic factor might be responsible for the clinical manifestations of the disease. A positional cloning approach was employed to investigate the pathogenic mechanism of KTS and to identify its susceptibility gene. A translocation of t(5;11)(q13.3; p15.1) has previously been found to be associated with KTS, raising the possibility that the translocation event could alter the function of a key gene involved in vascular morphogenesis and angiogenesis, resulting in the clinical manifestations of KTS. PCR analysis with somatic cell hybrids containing only the derivative chromosome 5 or the derivative chromosome 11 defined the precise locations of the two translocation breakpoints, thus allowing for the identification of the genes close to the breakpoints. A high-resolution physical map was constructed for the 5q13.3 region using bacterial artificial chromosomes (BACs) whose ends were sequenced for sequence tagged site (STS) development and analysis of the breakpoint sequences. The precise definition of both translocation breakpoints allowed the identification of genes close to the breakpoints. A single gene was discovered to be present near the KTS translocation breakpoint.

Isolation and characterization of the novel gene: The full length cDNA of the newly identified gene was cloned by RACE and RT-PCR and was found to be a novel gene. The protein encoded by this gene, named VG5Q, has 714 amino acids and an estimated molecular weight of 87 dDa. An RPS-BLAST search of the Conserved Domain Database at NCBI indicated that the VG5Q protein contains a forkhead-associated (FHA) domain and a G-patch domain. The FHA domain has been shown to be involved in phospho-dependent protein-protein interactions and G patch domains have been implicated as RNA-interacting modules. 3'-end cloning by 3'-RACE revealed that the KTS translocation breakpoint is located in the promoter region of VG5Q.

Functional association of the novel gene with KTS: To test whether VG5Q is a KTS gene, it was determined whether the t(5;11) translocation affects the expression of VG5Q. The VG5Q promoter/regulatory region was fused to the luciferase gene. A luciferase reporter gene was also constructed for the translocation junction fragment from derivative chromosome 11, which precedes the VG5Q coding region in the KTS patient with translocation t(5;11). Surprisingly, the VG5Q promoter with the translocation junction fragment increased the expression of the reporter gene by 3 fold in human umbilical vein endothelial cells (HUVEC) and by 2.7 fold in human embryonic kidney cells HEK-293 as compared to the wild-type VG5Q promoter construct. It was therefore concluded that the t(5;11) KTS translocation is a functional genetic defect that leads to overexpression of VG5Q.

Endothelial expression of VG5Q_: Northern blot analysis revealed a single 4.5 kb transcript in human microvascular endothelial cells. VG5Q was ubiquitously expressed in all tissues examined, presumably due to the presence of blood vessels embedded in these tissues. Western blot analysis with a polyclonal antibody against a synthetic polypeptide immunogen based on a unique VG5Q sequence recognized a predicted 87 kDa protein present in extracts of human endothelial cells. Using immunostaining with the anti-VG5Q antibody, it was found that VG5Q was expressed in blood vessels embedded in various tissues, but not in nonvascularized areas. It was therefore concluded that VG5Q encodes a novel vascular protein.

Subcellular localization of VG5Q: The VG5Q protein undergoes a dramatic change of localization during endothelial tube development. Determination of the subcellular localization of VG5Q protein in HMVEC cells revealed VG5Q protein expression in both the cytoplasm and nucleus and the strongest expression signal was observed in the cytoplasm. A dramatic change of the distribution pattern of VG5Q protein was observed during the process of tube formation in an in vitro model of angiogenesis where HMVEC and HUVEC were plated onto matrigel. When cells were cultured on matrigel for one hour, VG5Q protein began to redistribute by moving towards the cell periphery and was also detected outside the cell. At 4 hours, endothelial tubes were formed, and VG5Q protein was present inside tubes as well as outside of the tubes. In newly formed tubes, VG5Q protein was localized between cells and appeared to bridge the cells together. After the tubes were formed (24 hours), VG5Q protein within the nucleus completely disappeared. Immunostaining in various tissues also revealed that VG5Q protein is not present in the nucleus in mature blood vessels.

VG5Q is secreted during angiogenesis: VG5Q secretion during angiogenesis was confirmed by competitive ELISA assay. These results indicate that angiogenesis accompanies dynamic redistribution and secretion of VG5Q protein.

The E133K mutation in VG5Q increases angiogenesis: Because VG5Q mutations can cause vascular malformations associated with KTS, and VG5Q protein undergoes dynamic redistribution and secretion during angiogenesis, it was determined whether VG5Q directly functions as an angiogenic factor in vivo. The chick chorioallantoic membrane (CAM) assays revealed that the purified, wild type VG5Q protein is a potent angiogenic factor. VG5Q appeared to be as potent as VEGF in promoting angiogenesis. Surprisingly, the E133K mutation in VG5Q that is found in some KTS sufferers and which results in substitution of a negatively charged glutamine residue for a positively charged lysine residue, produced a significantly more potent angiogenic factor than the wild type protein. These results demonstrate that mutation E133K of VG5Q is a functional mutation that acts by a gain-of-function mechanism to increase angiogenesis. These data confirmed that similar to VEGF, VG5Q is a potent angiogenic factor.

Silencing of VG5Q expression inhibits endothelial tube formation: The physiological effect of reducing VG5Q expression at both mRNA and protein levels in endothelial cells was examined by RNA interference technology (siRNA) directed against VG5Q. Down-regulation of VG5Q significantly reduced endothelial cell proliferation. Microscopic examination revealed a marked increase in the number of floating cells, suggesting apoptosis of endothelial cells following transfection with siRNA.

Suppression of VG5Q causes endothelial apoptosis: flow cytometric analysis revealed that downregulation of VG5Q caused massive apoptosis of endothelial cells compared to control endothelial cells. Similar results were obtained with an anti-sense oligonucleotide against VG5Q. These results show that suppression of VG5Q expression induces apoptosis of endothelial cells. Additional experiments were performed to determine whether siRNA against VG5Q could lead to apoptosis in other cells including vascular smooth muscle cells (VSM), human embryonic kidney cells (HEK-293), and fibroblasts. Surprisingly, siRNA against VG5Q did not induce apoptosis in VSM, HEK-293, or fibroblasts, although siRNA appeared to be effective in suppressing expression of VG5Q in these cells.

VG5Q Suppression Inhibits Endothelial Cell Tube Formation: Endothelial tube formation was dramatically reduced when VG5Q expression was inhibited in endothelial cells. The mechanism for inhibition of tube formation following suppression of VG5Q expression is not clear. It is evident, however, that reduced VG5Q expression leads to endothelial cell apoptosis, which in turn results in disruption of tube formation. Interestingly, changes in intracellular localization of VG5Q during tube formation were observed in an in vitro model of angiogenesis. This supports a role for VG5Q as a signal molecule mediating endothelial cell-cell interactions during the formation of blood vessels.

Physiological Function of VG5Q is Similar to VEGF: On the basis of these results, the physiological function of VG5Q is highly likely to be comparable to that of the vascular endothelial growth factor, VEGF, which is a potent endothelial cell mitogen and a key regulator of angiogenesis. First, both proteins inhibit endothelial cell apoptosis, although the apoptotic signal-transduction pathways involved may differ. It was shown that hyperoxia-induced downregulation of VEGF led to selective apoptosis of endothelial cells in the neonatal retina and targeted deletion of the VEGF gene resulted in massive endothelial apoptosis (Alon, T. et al. Nat. Med. 1995, 1: 1024-8102; Carmeliet, P. et al., Nature 1996, 380, 435-39; Ferrara, N. et al. Nature 1996, 380:439-442). Recent studies demonstrated that VEGF induces expression of anti-apoptotic proteins such as Bcl-2, AL, survivin and XIAP (Gerber, H. P., et al., *J. Biol. Chem.* 1998, 273: 13313-13316; Nor, J. E. et al., Am. J. Pathol. 1999, 154, 375-384; Tran, J. et al. Biochem. Biophys. Res. Commun. 1999, 264: 781-788). Thus, the present invention demonstrates that down-regulation of VG5Q expression induces massive apoptosis in vascular endothelial cells. The present invention also demonstrates that down-regulation of VG5Q expression activates an apoptotic pathway, resulting in cell death of endothelial cells.

Both VEGF and VG5Q are potent factors that promote angiogenesis. As demonstrated by the present invention, purified VG5Q promotes angiogenesis in chick embryos as potently as VEGF. Down-regulation of VEGF can lead to regression of retinal capillaries in a model of hyperoxia-induced retinopathy of neonatal rats (Alon, T. et al. Nat. Med. 1995, 1: 1024-8102). Remarkably, as demonstrated by the present invention, down-regulation of VG5Q results in disappearance of endothelial tube formation in a model of angiogenesis. Expression analysis using a reporter gene with the VG5Q promoter fused to the luciferase gene suggests that VEGF does not regulate expression of VG5Q. Therefore, VG5Q and VEGF likely use different signaling pathways to mediate endothelial cell apoptosis or angiogenesis.

VG5Q interacts with TWEAK, a proangiogenic protein: A yeast two-hybrid screen was used to identify VG5Q-interacting proteins. One of the proteins identified by this screen was TWEAK (cytokine TNF-like weak inducer of apoptosis) (Tian X L, et al., Nature. 2004, 427:640-645). In vitro GST-pull down and in vivo co-immunoprecipitation and co-immunostaining confirmed the direct interaction between VG5Q and TWEAK. VG5Q and TWEAK may act synergistically to promote angiogenesis. This result thus connects VG5Q to another well-studied protein, TWEAK, involved in the angiogenic signaling pathway. TWEAK contains a signal peptide, and a smaller, biologically active form of TWEAK has been shown to be efficiently secreted from cells (Chicheportiche Y, et al., J Biol. Chem. 1997, 272:32401-32410). One receptor for TWEAK, Fn14 (fibroblast growth factor-inducible 14), has been identified (Wiley S R, et al., Immunity. 2001, 15:837-846; Wiley S R and Winkles J A, Cytokine Growth Factor Rev. 2003, 14:241-249). TWEAK acts like a ligand and binds to the Fn14 receptor with physiological affinity as a homotrimer and promotes angiogenesis in vivo (Wiley S R and Winkles J A., Cytokine Growth Factor Rev. 2003, 14:241-249) as potently as VEGF and FGF-2. TWEAK has been shown to promote cell proliferation and migration of HUVEC (Lynch C N, et al., J Biol. Chem. 1999, 274:8455-8459), and potentiates FGF-2 and VEGF activity in EC proliferation, which may be due to induction of Fn14 mRNA expression by FGF-2 and VEGF (Donohue P J, et al., Arterioscler Thromb Vasc Biol. 2003, 23:594-600) TWEAK treatment has been shown to promote NF-κB activation (Saitoh T, et al., J Biol. Chem. 2003, 278:36005-36012), ERK1/2, and JNK1/2 phosphorylation (Donohue P J, et al., Arterioscler Thromb Vasc Biol. 2003, 23:594-600). Under some experimental conditions, TWEAK also induces apoptosis on a select group of human tumor cell lines and on monocytes (Nakayama M, et al., J. Immunol. 2002, 168:734-743; Nakayama M, et al., J. Immunol. 2003; 170:341-348).

In summary, VG5Q is a novel protein encoded by a novel gene that is required for survival of endothelial cells as well as capillary tube formation. Suppression of VG5Q expression leads to endothelial cell apoptosis by activating an apoptotic pathway. The invention includes the important physiological function of VG5Q, and establish VG5Q as a critical regulatory factor for controlling an apoptotic signal-transduction pathway. The present invention has important clinical implications for developing new approaches for treating conditions such as cancer that depend on angiogenesis. Agents that can suppress the expression of VG5Q promote apoptosis of endothelial cells and inhibition of angiogenesis. Conversely, the discovery of VG5Q provides a new pro-angiogenic factor capable of inducing angiogenesis where required, such as for the treatment of heart diseases, such as myocardial ischemia, peripheral vascular disease, and in wound healing.

DEFINITIONS

This section sets forth definitions that are well understood in the art. The term "angiogenesis" refers to the process of the growth of new blood vessels. "Angiogenesis-stimulating growth factors" cause new blood vessels to grow and are "proangiogenic", whereas "angiogenesis inhibitors" stop blood vessels from forming and are "anti-angiogenic". The inhibition and/or suppression of angiogenesis is desired for the treatment of diseases which are characterized by excessive angiogenesis. Excessive angiogenesis occurs in diseases such as cancer, diabetic blindness, age-related macular degeneration, rheumatoid arthritis, and psoriasis, and more than 70 other conditions. Likewise, inducing and/or enhancing angiogenesis is desired for the treatment of diseases, which are characterized by insufficient angiogenesis. Insufficient angiogenesis occurs in diseases such as coronary artery disease, peripheral arterial disease, stroke, diabetes, and wound healing, such as healing of broken bones, burns, diabetic ulcers, or traumatic or surgical wounds, and organ transplantation. Such compounds may also be used to treat peripheral vascular disease, cerebral vascular disease, hypoxic tissue damage, or coronary vascular disease as well as to treat patients who have or have had transient ischemic attacks, vascular graft surgery, balloon angioplasty, frostbite, gangrene, or poor circulation. A variety of well-known bioassays may be employed to determine whether a peptide fragment or analog of a VG5Q protein is angiogenic. These assays include assays of the motility of cultured endothelial cells, mouse corneal assays, and immunohistological assays of the vascularization of implanted tumors in animals following the administration of a peptide of interest. Additional assays include chicken chorioallantroic membrane (CAM) assays and bovine capillary endothelial cell proliferation assays which are also well-known to one of ordinary skill in the art (e.g., described by O'Reilly et al. Cell 1994, 79:315-328).

"VG5Q protein" refers to protein that has pro-angiogenic activity, a forkhead-associated domain, a G-patch domain, characteristic subcellular localization in an in vitro Matrigel model of angiogenesis: towards the cell periphery in early stages of tubulogenesis, between cells in newly formed endothelial tubes, and no nuclear staining after 24 hours, expressed in endothelial cells, secretion during angiogenesis, and interacts with TWEAK. In a specific embodiment, the protein is a human protein having an amino acid sequence of SEQ ID NO: 2 of variants thereof, e.g., allelic variants, including the E133K gain of function variant. In another embodiment, the protein is a murine protein having an amino acid sequence of SEQ ID NO: 4 or variants thereof, e.g., allelic variants. VG5Q proteins of the invention can share at least 90% sequence identity, 95% sequence identity, and preferably greater than 99% sequence identity, with SEQ ID NO: 2 or SEQ ID NO: 4. Suppression of VG5Q protein leads to the inhibition of endothelial tube formation and endothelial apoptosis. The gene coding for VG5Q was identified in course of a search for the susceptibility gene for Klippel-Trenaunay Syndrome (KTS).

"VG5Q gene" refers to the nucleic acids that encode the VG5Q protein. In a specific embodiment, the gene is a human gene having a nucleic acid sequence of SEQ ID NO: 1 and variants thereof, e.g., allelic variants, including the E133K gain of function variant. In another embodiment, the protein is a murine gene having a nucleic acid sequence of SEQ ID NO: 3 or variants thereof, e.g., allelic variants. VG5Q genes of the invention can share at least 90% sequence identity, 95% sequence identity and preferably greater than 99% sequence identity, with SEQ ID NO: 1 or SEQ ID NO: 3.

"Klippel-Trenaunay Syndrome" or "KTS" is defined herein as a congenital vascular disease characterized by a combination of capillary malformations (usually port-wine stains), soft tissue or bony hypertrophy (or both); and varicose veins or venous malformations, often with persistent embryologic veins. The disease affects many parts of the body, and is associated with a significant morbidity with a profound impact on a patient's life (e.g. pain, disability, disfigurement, and social stress). KTS is commonly sporadic and its etiology is unknown.

"Gain-of-function" mutation is a functional mutation in VG5Q that causes increased angiogenesis. A "gain-of-function" mutation can be assayed by the Chick Chorioallantoic Membrane Assay for angiogenic potency. For example, the VG5Q E133K mutation found in KTS increases angiogenesis is a "gain-of function" mutation The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant. "Inhibiting", "suppressing", "silencing", and "blocking" are all defined herein as methods for the inhibition and/or suppression of VG5Q angiogenesis. These methods include "RNA interference" (RNAi) with anti-VG5Q siRNA duplexes of typically 21 to 25-bases, and administration of "anti-sense" VG5Q oligonucleotides, short nucleotide sequence formulated to be complementary to a portion or to the entire coding sequence of the VG5Q mRNA. An "antisense" nucleic acid molecule or oligonucleotide is a single stranded nucleic acid molecule, which may be DNA, RNA, a DNA-RNA chimera, or a derivative thereof, which, upon hybridizing under physiological conditions with complementary bases in an RNA or DNA molecule of interest, inhibits the expression of the corresponding gene by inhibiting, e.g., mRNA transcription, mRNA splicing, mRNA transport, or mRNA translation or by decreasing mRNA stability. As presently used, "antisense" broadly includes RNA-RNA interactions, RNA-DNA interactions, and RNase-H mediated arrest. Antisense nucleic acid molecules can be encoded by a recombinant gene for expression in a cell (see, e.g., U.S. Pat. Nos. 5,814,500 and 5,811,234), or alternatively they can be prepared synthetically (see, e.g., U.S. Pat. No. 5,780,607). According to the present invention, the involvement of VG5Q in regulation of angiogenesis may be identified, modulated and studied using antisense nucleic acids derived on the basis of VG5Q-encoding nucleic acid molecules of the invention.

The term "ribozyme" is used to refer to a catalytic RNA molecule capable of cleaving RNA substrates. Ribozyme specificity is dependent on complementary RNA-RNA interactions (for a review, see Cech and Bass, Annu. Rev. Biochem. 1986; 55: 599-629). Two types of ribozymes, hammerhead and hairpin, have been described. Each has a structurally distinct catalytic center. The present invention contemplates the use of ribozymes designed on the basis of the VG5Q-encoding nucleic acid molecules of the invention to induce catalytic cleavage of the corresponding mRNA, and in this way inhibit expression of the VG5Q gene. Ribozyme technology is described further in Intracellular Ribozyme Applications Principals and Protocols, Rossi and Couture ed., Horizon Scientific Press, 1999.

The term "RNA interference" or "RNAi" refers to the ability of double stranded RNA (dsRNA) to suppress the expression of a specific gene of interest in a homology-dependent manner. It is currently believed that RNA interference acts post-transcriptionally by targeting mRNA molecules for degradation. RNA interference commonly involves the use of dsRNAs that are greater than 500 bp; however, it can also be mediated through small interfering RNAs (siRNAs) or small hairpin RNAs (shRNAs), which can be 10 or more nucleotides in length and are typically greater than 18 nucleotides in length. For reviews, see Bosner and Labouesse, Nature Cell Biol. 2000, 2: E31-E36 and Sharp and Zamore, Science 2000, 287: 2431-2433. The present invention exemplifies the use of dsRNAs designed on the basis of VG5Q-encoding nucleic acid molecules of the invention in RNA interference methods to specifically inhibit VG5Q gene expression (Tuschl, T, US Published application 20030108923) RNA sequence-specific mediators of RNA interference "Peptide fragment" refers to a fragment of a VG5Q protein having sufficient length to be angiogenic and/or immunogenic and peptide analogs include those variants of VG5Q protein or peptide fragments of VG5Q having substitutions, insertions, or deletions of one or more amino acid residues or having modifications on the side groups of amino acid residues and which maintain the function of the complete VG5Q protein.

The "nucleic acid delivery vehicles" comprise a nucleic acid sequence coding for VG5Q in a "nucleic acid carrier". The "nucleic acid carrier" may be a vector, a lipid, a gene gun, or any suitable carrier known in the art.

The term "about" or "approximately" means within an acceptable error range for the particular value as determined by one of ordinary skill in the art, which will depend in part on how the value is measured or determined, i.e., the limitations of the measurement system, or the degree of precision required for a particular purpose, such as a pharmaceutical formulation. For example, "about" can mean within 1 or more than 1 standard deviations per the practice in the art. Alternatively, "about" can mean a range of up to 20%, preferably up to 10%, more preferably up to 5%, and more preferably still up to 1% of a given value.

Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "nucleic acid hybridization" refers to anti-parallel hydrogen bonding between two single-stranded nucleic acids. Nucleic acid molecules are "hybridizable" to each other when at least one strand of one nucleic acid molecule can form hydrogen bonds with the complementary bases of another nucleic acid molecule under defined stringency conditions. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7. Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary. Hybridization conditions of higher stringency may be used to allow hybridization of only sequences having at least 80% sequence identity, at least 90% sequence identity, at least 95% sequence identity, or at least 99% sequence identity. (see Molecular Biology of the Cell, Alberts et al., 3rd ed., New York and London: Garland Publ., 1994, Ch. 7, Southern, J. Mol. Biol. 1975; 98: 503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3).

Nucleic acid molecules that "hybridize" to any of the VG5Q-encoding nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular VG5Q-encoding nucleic acid.

The term "homologous" as used in the art commonly refers to the relationship between nucleic acid molecules or proteins that possess a "common evolutionary origin," (Reeck et al., Cell 1987; 50: 667). Such nucleic acid molecules or proteins have sequence similarity, which provides the structural basis for the homology, whether in terms of substantial percent similarity or the presence of specific residues or motifs at conserved positions.

The terms "percent (%) sequence similarity", "percent (%) sequence identity", and the like, generally refer to the degree of identity or correspondence between different nucleotide sequences of nucleic acid molecules or amino acid (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc. The determination of percent identity between two sequences can be accomplished using a mathematical algorithm. A non-limiting example of a mathematical algorithm utilized for the comparison of two sequences is the algorithm of Karlin and Altschul, PNAS USA 1990, 87:2264, modified as in Karlin and Altschul, PNAS USA 1993, 90:5873-5877. Such an algorithm is incorporated into the NBLAST and XBLAST programs of Altschul et al., J. Mol. Biol. 1990; 215: 403. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb.

In addition to the cDNA sequences encoding human VG5Q protein (as shown in SEQ ID NO: 2), the present invention further provides polynucleotide molecules comprising nucleotide sequences having certain percentage sequence identities to any of the aforementioned sequences. Such sequences preferably hybridize under conditions of moderate or high stringency as described above, and may include species orthologs. As used herein, the term "orthologs" refers to genes in different species that apparently evolved from a common ancestral gene and retain the same function. Sequence comparison algorithms that can be used to identify orthologs include without limitation include the BLAST, FASTA, DNA Strider, and the GCG pileup program. Orthologs often have high sequence similarity. The present invention encompasses all orthologs of VG5Q. In addition to rat (Genbank XP_226709.2), mouse (AY_500995) and human (AY_500994 and AY_500996) orthologs, particularly useful VG5Q orthologs of the present invention are monkey and porcine orthologs. Structural features of these VG5Q orthologs are a forkhead domain and a G-patch domain. A functional feature is angiogenic activity.

A "recombinant DNA molecule" refers to a DNA molecule that has undergone a molecular biological manipulation, which may or not be actual recombination.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluorouracil. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981, 290:304 310), the promoter contained in the 3' long terminal repeat of Rous sarcoma virus (Yamamoto et al., Cell 1980, 22:787 797), the herpes thymidine kinase promoter (Wagner et al., Proc. Natl. Acad. Sci. USA 1981, 78:1441 1445), the regulatory sequences of the metallothionein gene (Brinster et al., Nature 1982, 296:39-42); prokaryotic expression vectors such as the beta lactamase promoter (Villa Komaroff et al., Proc. Natl. Acad. Sci. USA 1978, 75:3727 3731), or the tac promoter (DeBoer et al., Proc. Natl. Acad. Sci. USA 1983, 80:21 25); see also "Useful proteins from recombinant bacteria" in Scientific American 1980, 242:74 94; promoter elements from yeast or other fungi such as the Gal 4 promoter, the ADC (alcohol dehydrogenase) promoter, PGK (phospho glycerol kinase) promoter, alkaline phosphatase promoter; and transcriptional control regions that exhibit hematopoietic tissue specificity, in particular: beta globin gene control region which is active in myeloid cells (Mogram et al., Nature 1985, 315:338 340; Kollias et al., Cell 1986, 46:89 94), hematopoietic stem cell differentiation factor promoters, erythropoietin receptor promoter (Maouche et al., Blood 1991, 15:2557), etc.

The term "gene", also called a means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described infra.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. In a specific embodiment, the protein of interest is expressed in COS-1 or C2C12 cells. Other suitable cells include CHO cells, HeLa cells, 293T (human kidney cells), mouse primary myoblasts, and NIH 3T3 cells.

As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). A material shall be deemed isolated if it is present in a cell extract or if it is present in a heterologous cell or cell extract. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The phrase "therapeutically effective amount" is used herein to mean an amount sufficient to achieve a desired therapeutic result, e.g., reduce by at least about 15 percent, preferably by at least 50 percent, more preferably by at least 90 percent, and most preferably eliminate or prevent, a clinically significant deficit in the activity, function and response of the host. Alternatively, a therapeutically effective amount is sufficient to cause an improvement in a clinically significant condition in the host.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

In accordance with the present invention there may be employed conventional molecular biology, microbiology, cell culture, protein expression and purification, antibody, and recombinant DNA techniques well known to those of ordinary skill in the art. Such techniques are explained fully in the literature. See, e.g., Sambrook, Fritsch and Maniatis, Molecular Cloning: A Laboratory Manual, Second Edition (Cold Spring Harbor Laboratory Press, New York: 1989); DNA Cloning: A Practical Approach, Volumes I and II (Glover ed.: 1985); Oligonucleotide Synthesis (Gait ed.: 1984); Nucleic Acid Hybridization (Hames & Higgins eds.: 1985); Transcription And Translation (Hames & Higgins, eds.: 1984); Animal Cell Culture (Freshney, ed.: 1986); Immobilized Cells And Enzymes (IRL Press: 1986); Perbal, A Practical Guide To Molecular Cloning (1984); Ausubel et al., eds. Current Protocols in Molecular Biology, (John Wiley & Sons, Inc.: 1994); and Harlow and Lane. Antibodies: A Laboratory Manual (Cold Spring Harbor Laboratory Press: 1988).

Use of VG5Q for Preventing Angiogenesis

Based on the foregoing results, the present invention provides methods and compositions for the treatment of angiogenesis-mediated diseases. The inhibition and/or suppression of angiogenesis is desired for the treatment of diseases, which are characterized by excessive angiogenesis. Excessive angiogenesis occurs in diseases such as cancer, diabetic blindness, age-related macular degeneration, rheumatoid arthritis, and psoriasis, and more than 70 other conditions. Accordingly, the present invention encompasses methods and therapeutic compositions for the inhibition and/or suppression of angiogenesis by inhibiting, suppressing, silencing or blocking VG5Q.

RNA interference (RNAi): In one embodiment of the present invention, the expression of VG5Q is suppressed by RNA interference (RNAi). The therapeutic efficacy of such short double stranded RNA molecules in inhibiting target mRNA expression has already been demonstrated. For example, RNAi involving the silencing of the Fas gene has been shown in vivo to halt hepatitis (Song et al., Nature Med. 2003, 9(3): 347-351).

For in vivo administration into mammalian cells short anti-VG5Q siRNA duplexes of typically 21 to 25-base pairs can be used. The VG5Q siRNA molecules can be chemically or enzymatically synthesized as 21 to 25-nucleotide siRNA duplexes which can be administered in naked form or in liposome-encapsulated form. Alternatively, the VG5Q siRNA can be expressed from DNA template vectors, including viral vectors. Endogenous vector-mediated delivery is possible by inserting DNA templates for siRNAs into RNA polymerase III (pol III) transcription units, which are based on the sequences of the natural transcription units of the small nuclear RNA U6 or the human RNase P RNA H1.

Two approaches are available for expressing siRNAs: the sense and antisense strands constituting the siRNA duplex can be transcribed from individual promoters, or the siRNAs are expressed as fold-back stem-loop structures that give rise to siRNAs after intracellular processing by the enzyme Dicer. In the first instance, target regions may be selected such that the synthetic siRNA duplex sequences may contain uridine residues in the 2-nt overhangs. Uridine residues in the 2-nt 3'-overhang can be replaced by 2'-deoxythymidine without loss of activity, which may enhance nuclease resistance of siRNA duplexes when applied to mammalian cells. For plasmid-based expression of short hairpin loops which give rise to siRNAs in vivo, the polymerase III promoter of H1 RNA (human RNase P RNA) can be chosen to drive the transcription of a short RNA hairpin which is processed to siRNA. The transcription is terminated by the encounter of a polythymidine tract (T5) after the incorporation of two to three uridine residues encoded by the T5 element. One example of a suitable DNA expression vector for siRNA is the pSUPER, available from OligoEngine, which includes the polymerase-III H1-RNA gene promoter, although there are other suitable vectors known to those of skill in the art, including, in non-limiting examples, those disclosed by Paddison et al., Cancer cell 2002, 2:17-23, and Genes Dev. 2002, 16: 948-958, Brummelkamp et al., Cancer Cell 2002, 2:243-247, and Coburn et al., J. Antimicrob. Chemother., 2003, 51, 753-756.

anti-sense VG5Q oligonucleotides: According to another preferred embodiment of the present invention, VG5Q expression is inhibited through therapeutic compositions comprising anti-sense VG5Q oligonucleotides. Nucleic acids complementary to all or part of the VG5Q cDNA sequence may be used to inhibit VG5Q expression. Anti-sense treatment may be carried out by administering to a mammal, such as a human, DNA containing a promoter, e.g., an endothelial cell-specific promoter including the VG5Q promoter provided herein by the present invention, operably linked to a DNA sequence (an anti-sense template), which is transcribed into an anti-sense RNA. Alternatively, anti-sense oligonucleotides may be introduced directly into vascular cells. The anti-sense oligonucleotide may be a short nucleotide sequence formulated to be complementary to a portion or to the entire coding sequence of the VG5Q mRNA.

Oligonucleotides complementary to various portions of VG5Q can readily be tested in vitro for their ability to decrease production of the respective VG5Q gene product.

Sequences which decrease production of VG5Q in in vitro cell-based or cell-free assays can then be tested in vivo in animals to determine whether blood vessel formation is decreased. Standard methods of administering anti-sense therapy have been described. See, e.g., Melani et al., 1991, Cancer Res. 51:2897-2901. Following transcription of a DNA sequence into an anti-sense RNA, the anti-sense RNA binds to its target nucleic acid molecule, such that as an mRNA molecule, thereby inhibiting the expression of the target nucleic acid molecule. For example, an anti-sense sequence complementary to a portion or all of VG5Q mRNA can be used to inhibit expression of VG5Q, thereby decreasing the level of transcription of VG5Q, which in turn leads to a decrease in new blood vessel formation. Both the anti-VG5Q siRNAs and the antisense oligonucleotides provided by the present invention can be further optimized through chemical modifications known to those of skill in the art, such as those disclosed in Kurreck, Eur. J. Biochem. 270, 1628-1644 (2003).

anti-VG5Q antibodies: In a further preferred embodiment the present invention provides monoclonal and polyclonal anti-VG5Q antibodies. Because VG5Q is secreted extracellularly during angiogenesis and likely functions as a signal molecule mediating endothelial cell-cell interactions during the formation of blood vessels, anti-VG5Q antibodies can be used to inhibit the angiogenic effect of VG5Q by blocking its cell-cell signaling function in a manner analogous to the antibody-mediated inhibition of VEGF which has been shown to inhibit the growth of solid tumors in in vivo animal experiments (Kim, K. J. et al., Nature 1993, 362: 841-844; S. Kondo et al., BBRC 1993, 194(3): 1234-1241).

Methods of producing antibodies are well known in the art and may employ hybridoma technology, as well as recombinant technologies to produce variants with optimized properties. Such variants may comprise single chain recombinant antibodies, humanized chimeric antibodies, immunologically active fragments of antibodies, or immunoadhesins as examples of constructs that can be made by a person of skill in the art using routine techniques. Optimization of VG5Q antibodies and antibody variants may further be performed to enhance their pharmacokinetic properties or improve their pharmacodynamic performance, including increasing their affinity and/or half-life or reducing unwanted toxic side effects. For example, excision of stretches of high positive charges may be performed to minimize nonspecific adhesion to negatively charged proteoglycans in the extracellular matrix at the site of administration of the antibodies and their variants. Many other optimization techniques are well known in the art and require no more than routine procedures.

Antibodies to the expressed and isolated VG5Q proteins can be produced by several well known techniques. Antibodies are prepared using standard immunization protocols in rabbits, goats, sheep, mice or other suitable animal and recovering the antisera. In addition, antibody-secreting cells from the immunized animals can be immortalized using fusion techniques to produce hybridomas which can be screened for antibodies immunoreactive with VG5Q (see e.g. "Antibodies: A Laboratory Manual," E. Harlow and D. Lane, Cold Spring Harbor Laboratory, Cold Spring Harbor, N.Y.). For example, the polyclonal antibodies of the present invention can be raised in a mammal by one or more injections of an immunizing agent which may further comprise an adjuvant. Typically, the immunizing agent and/or adjuvant will be injected in the mammal by subcutaneous or intraperitoneal injections. The immunizing agent may include the VG5Q polypeptide, or an immunogenic VG5Q peptide. The immunizing agent can also be conjugated to a protein known to be immunogenic in the mammal being immunized. Examples of such immunogenic proteins include but are not limited to keyhole limpet hemocyanin, serum albumin, bovine thyroglobulin, and soybean trypsin inhibitor. Exemplary adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal anti-VG5Q antibodies: Monoclonal anti-VG5Q antibodies may be prepared using hybridoma methods, such as those described by Kohler and Milstein, Nature, 256:495 (1975). The well-known hybridoma method entails immunizing a mouse, hamster, or other appropriate host animal, with an immunizing agent to elicit lymphocytes that produce or are capable of producing antibodies that will specifically bind to the immunizing agent. As for the production of polyclonal anti-VG5Q antibodies, the immunizing agent may be the VG5Q polypeptide or an immunogenic VG5Q peptide. The isolated lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). The hybridoma cells are cultured in a suitable culture medium that contains one or more substances designed to inhibit the growth or survival of the unfused, immortalized cells, for example, hypoxanthine, aminopterin, and thymidine ("HAT medium").

The culture medium in which the hybridoma cells are cultured can then be assayed for the presence of monoclonal antibodies directed against VG5Q. The binding specificity and affinity of monoclonal antibodies produced by the hybridoma cells can then be determined by immunoprecipitation or by in vitro binding assays, such as radioimmunoassay (RIA) or enzyme-linked immunoabsorbent assay (ELISA), all of which are techniques that are well known in the art. Alternatively, the monoclonal antibodies of the present invention may be produced by recombinant DNA methods that are well known in the art. The DNA encoding the monoclonal antibodies of the invention is isolated from the hybridomas and sequenced using, for example, oligonucleotide probes that are specific for genes encoding the heavy and light chains of the antibodies. Once isolated, the DNA may be placed into expression vectors, which are then transfected into suitable host cells for the recombinant production of the antibodies. Suitable host cells for the purposes of the present invention include both eukaryotic and prokaryotic cells. For example, E. coli bacterial cells are suitable prokaryotic host cells, while animal, such as COS, human, such as HeLa, or yeast cells are examples of suitable eukaryotic host cells.

Humanized and human antibodies: The anti-VG5Q antibodies of the present invention comprise humanized antibodies or human antibodies. Humanized forms of non-human antibodies can be chimeric immunoglobulins, immunoglobulin chains, or fragments thereof (such as Fv, Fab, Fab', F(ab')$_2$, or other antigen-binding subsequences of antibodies) which contain minimal sequence derived from non-human immunoglobulin. The humanized antibody optimally comprises at least a portion of an immunoglobulin constant region (Fc) derived from a human immunoglobulin (Jones et al., Nature 1986, 321:522-525; Riechmann et al., Nature 1988, 332:323-329; Presta, Curr. Op. Struct. Biol. 1992, 2:593-596). Methods for humanizing non-human antibodies are well known in the art. Humanization can be essentially performed following the method of Winter and co-workers (Jones et al., Nature 1986, 321:522-525; Riechmann et al., Nature 1988, 332:323-327; Verhoeyen et al., Science 1988, 239:1534-1536), by substituting rodent CDRs or CDR sequences for the corresponding sequences of a human antibody. In practice, the majority of humanized antibodies are human antibodies in which some CDR residues are substituted by residues from analogous sites in rodent antibodies.

Human antibodies can also be produced using various techniques known in the art, including phage display libraries (Hoogenboom and Winter, J. Mol. Biol. 1991, 227:381; Marks et al., J. Mol. Biol. 1991, 222:581). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 1991, 147(1):86-95).

Human monoclonal antibodies and human sequence antibodies directed against human VG5Q can be generated using transgenic mice carrying a human immune system rather than the mouse system. These transgenic mice, also referred to herein as "HuMAb-Mouse™", contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. Nature 1994, 368(6474): 856-859 and U.S. Pat. No. 5,770,429). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N., *Handbook of Experimental Pharmacology* 1994, 113:49-101; Lonberg, N. and Huszar, D., *Intern. Rev. Immunol.* 1995, 13: 65-93, and Harding, F. and Lonberg, N., *Ann. N.Y. Acad. Sci.* 1995, 764:536-546). The preparation of transgenic mice is described in Taylor, L. et al., *Nucleic Acids Research* 1992, 20:6287-6295; Chen, J. et al. *International Immunology* 1993, 5: 647-656; Tuaillon et al., *Proc. Natl. Acad. Sci. USA* 1993, 90:3720-3724; Choi et al., 1993 *Nature Genetics* 4:117-123; Chen, J. et al. (1993) *EMBO J.* 12: 821-830; Tuaillon et al. (1994) *J Immmunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol. Vol.* 13: 65-93; Harding, F. and Lonberg, N. (1995) *Ann. N.Y. Acad. Sci.* 764:536-546; Fishwild, D. et al. (1996) *Nature Biotechnology* 14: 845-851. See further, U.S. Pat. Nos. 5,625,126 and 5,770,429, both to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992. Alternatively, the CMD and HCo12 transgenes, described in Examples 1 and 2, below, can be used to generate human anti-CTLA-4 antibodies.

Downregulating VG5Q expression by promoter modulation: In another preferred embodiment, the present invention provides methods for and agents capable of downregulating VG5Q expression via modulation of its promoter (SEQ ID NO: 8). The VG5Q promoter is regulatable as evidenced by its upregulation through translocation to another chromosomal location. Thus, for instance, triple helix forming oligodeoxynucleotides (TFOs) can be designed to bind to the VG5Q promoter region in order to prevent transcription factor access to the promoter region thus preventing transcription of the VG5Q gene. The design of TFOs is well known in the art (Durland et al., Biochemistry 1991, 30(38):9246-55; Reither et al., BMC Biochem. 2002 Sep. 12 E-pub ahead of print). Alternatively, the VG5Q regulatory region can be linked to a reporter gene, such as luciferase, and transfected or cotransfected into cell lines for the identification of drugs, such as small molecules, or proteins that upregulate or downregulate the activity of the VG5Q promoter.

Disruption of VG5Q binding to receptor/ligand: The present invention further provides binding partners, such as ligands or receptors for VG5Q. One of skill in the art will know how to identify and isolate such binding partners. Accordingly, the present invention encompasses compositions comprising such VG5Q receptors/ligands. Assays to identify proteins involved in important interactions with other proteins are well known in the art and may comprise the two-hybrid system (Fields & Song, Nature 1989, 340:245-246); Chien et al., PNAS USA 1991, 88, 9578-9582). A method of evaluating a compound for the ability to interact with, e.g., bind, VG5Q is provided. The method includes contacting the compound with the VG5Q polypeptide and evaluating ability of the compound to interact with, e.g., to bind or form a complex with the VG5Q polypeptide. This method can be performed in vitro, e.g., in a cell free system, or in vivo, e.g., in a two-hybrid interaction trap assay. This method can be used to identify naturally occurring molecules that interact with VG5Q polypeptide, such as receptors or ligands for VG5Q, or it can be used to find natural or synthetic inhibitors of VG5Q.

Because the present invention has made available, for the first time, the VG5Q gene and cDNA, identification of binding or interaction partners is straightforward. Briefly, the VG5Q gene or cDNA is cloned into a specific plasmid in such a way that it is expressed fused to the DNA-binding domain of a yeast transcriptional activator such as GAL4 which has two separable and functionally essential domains, one for DNA-binding and the other for transcriptional activation. Genes or cDNAs encoding putative binding partners of VG5Q are cloned in such a way that each putative partner is expressed fused to the transcriptional activation domain of the same DNA-binding protein. Introduction of both types of fusion into the same yeast cell results in generation of functional DNA-binding protein only if the fusion partners of the two domains of this protein interact with one another closely enough to bring together its two separately-expressed domains. Clones which produce such functional DNA-binding protein can be readily selected by plating them on a medium which requires the yeast to produce an enzyme that is under the control of the DNA-binding protein. The gene or cDNA for the partner which binds to the previously identified component can then be recovered from yeast clones which grow on the selective medium. Other methods include but are not limited to using VG5Q as an affinity ligand to identify other proteins which bind to it; labeling VG5Q with a detectable label and using it as a probe to identify interaction partners on blots of electrophoresis gels; labeling VG5Q and using it to probe libraries of genes and/or cDNAs; labeling VG5Q and using it to probe cDNA expression libraries to find clones synthesizing proteins which can bind to VG5Q; performing UV-crosslinking studies to identify cellular components which can bind to VG5Q; using VG5Q in gel retardation assays which would detect its ability to bind to DNA sequences; performing footprinting analyses to identify the regions within a nucleic acid to which VG5Q binds; and so on.

VG5Q for Promotion of Angiogenesis

Conversely, inducing and/or enhancing angiogenesis is desired for the treatment of diseases, which are characterized by insufficient angiogenesis. Insufficient angiogenesis occurs in diseases such as coronary artery disease, peripheral arterial disease, stroke, diabetes and delayed wound healing. In these conditions, inadequate blood vessels grow and circulation is not properly restored, leading to the risk of tissue death. Insufficient angiogenesis occurs when the tissue cannot produce adequate amounts of angiogenic growth factors. Therapeutic angiogenesis, aimed at stimulating new blood vessel growth with growth factors, is being developed to treat these conditions. Thus, the present invention provides methods and compositions for induced and/or enhanced angiogenesis by increasing the levels of VG5Q proteins, including both wild type and mutant VG5Q proteins, by administering various therapeutic compositions comprising the VG5Q protein or through transfecting the cells in the mammal to express the VG5Q protein via gene therapy methods, which are well-known in the art. In addition, compositions that enhance cellular production of VG5Q may be used in methods to promote new blood vessel formation.

Delivery of Recombinant VG5Q protein and active fragments: A method of increasing the levels of VG5Q proteins or polypeptides in a cell is intracellular expression of recombinant VG5Q or active fragments thereof. DNA encoding VG5Q is administered alone or as part of an expression vector. The DNA is introduced into its target cells, e.g., endothelial cells at an anatomical site in need of angiogenesis and directs the production of VG5Q proteins to enhance production of new blood vessels Delivery of Proangiogenic Receptor/ligand of VG5Q: Binding partners of VG5Q are identified as described above. To enhance angiogenesis, one of ordinary skill in the art could use methods for intracellular expression of proangiogenic binding partners of VG5Q, including TWEAK as described supra. A higher local concentration of VG5Q binding partners may have a proangiogenic effect, either alone or delivered in combination with VG5Q.

Methods for Intracellular Expression of Sense or Antisense VG5Q DNA

The in vivo transfer of nucleic acids into eukaryotic cells may be accomplished in a variety of delivery systems known in the art, including vectors, liposomes, receptor-mediated delivery systems, non-viral nucleic acid-based vectors, erythrocyte ghosts, or microspheres. Alternatively, naked DNA may be administered using a biolistic delivery device. Expression vectors for use in a therapeutic composition include any appropriate gene therapy vectors, such as nonviral (e.g., plasmid vectors), retroviral, adenoviral, herpes simplex viral, adeno-associated viral, polio viruses and vaccinia vectors. Examples of retroviral vectors include, but are not limited to, Moloney murine leukemia virus (MoMuLV), Harvey murine sarcoma virus (HaMuSV), murine mammary tumor virus (MuMTV), and Rous Sarcoma Virus (RSV)-derived recombinant vectors. Gene therapy vectors can be made tissue specific by, for example, linking the VG5Q encoding nucleotide sequence to a tissue-specific promoter. Multiple teachings of gene therapy are available to those skilled in the art, e.g., W. F. Anderson. "Prospects for Human Gene Therapy" Science 226: 401-409 (1984); S. H. Hughes. "Introduction" Current Communications in Molecular Biology 71:1-12 (1988); N. Muzyczka and S. McLaughlin. "Use of Adeno-associated Virus as a Mammalian Transduction Vector" Communications in Molecular Biology 70: 39-44 (1988); T. Friedman. "Progress Toward Human Gene Therapy" Science 244: 1275-1281 (1989) and W. F. Anderson, "Human Gene Therapy" Science 256: 608-613 (1992).

The nucleic acid molecule can be delivered "naked" by direct injection into the blood stream or to the desired tissue or organ of a subject. Alternatively, the nucleic acid molecule can be combined with a lipid compound which facilitates the uptake of the molecule by cells. The lipid compounds include liposome, lipofectins, cytofectins, lipid-based positive ions, and then introduced into the body fluids, the blood stream, or a selected tissue site. Liposome-mediated gene therapy is well known in the art and is described by, e.g., Lesoon-Wood et al., Human Gene Ther. 6: 395, 1995; Tsan et al., Am. J. Physiol 268: 11052, 1995; Vieweg et al., Cancer Res. 5585: 2366, 1995; Trivedi et al., J. Neurochem. 64: 2230, 1995; Hickman et al., Human Gene Ther. 5:1477, 1994; Westbrook et al. Human Mol. Genet. 3: 2005, 1994; Schmid et al., Z. Gastroenterol 32: 665, 1994; Hofland et al., Biochem. Biophys. Res. Commun. 207: 492, 1995; Plautz et al., Ann. N.Y. Acad. Sci. 7168: 144, 1994. Other DNA carriers which can facilitate the uptake of a desired vector by the target cells include nuclear protein, or ligands for certain cell receptors, which can be combined with a vector in engineered vesicles for delivery.

Pharmaceutical Compositions

The determination of an appropriate treatment regimen (i.e., dosage, frequency of administration, systemic vs. local, etc.) is within the skill of the art. For administration, the antibodies will be formulated in a unit dosage injectable form (solution, suspension, emulsion, etc.) in association with a pharmaceutically acceptable carrier. Such vehicles are usually nontoxic and non-therapeutic. Examples of such vehicles are water, saline, Ringer's solution, dextrose solution, and Hank's solution. Non-aqueous vehicles such as fixed oils and ethyl oleate may also be used. A preferred vehicle is 5% (w/w) human albumin in saline. The vehicle may contain minor amounts of additives, such as substances that enhance isotonicity and chemical stability, e.g., buffers and preservatives.

The therapeutic compositions described herein, as well as their biological equivalents or pharmaceutically acceptable salts, can be administered independently or in combination by any suitable route, including oral, subcutaneous and parenteral administration. Examples of parenteral administration include intravenous, intraarterial, intramuscular, intraperitoneal, and the like. The routes of administration described herein are merely exemplary and in no way limiting.

The dose of the therapeutic compositions administered to an animal, particularly in a human, in accordance with embodiments of the invention, should be sufficient to effect to desired response in the animal over a reasonable time frame. It is known that the dosage of therapeutic compositions depends upon a variety of factors, including the strength of the particular therapeutic composition employed, the age, species, condition or disease state, and the body weight of the animal.

Moreover, dose and dosage regimen, will depend mainly on the type of biological damage to the host, the type of subject, the history of the subject, and the type of therapeutic composition being administered. The size of the dose will be determined by the route, timing and frequency of administration as well as the existence, nature and extent of any adverse side effects that might accompany the administration of a particular therapeutic composition and the desired physiological effect. It is also known that various conditions or disease states, in particular, chronic conditions or disease states, may require prolonged treatment involving multiple administrations.

Therefore, the amount of the therapeutic composition must be effective to achieve an enhanced therapeutic index. It is noted that humans are generally treated longer than mice and rats with a length proportional to the length of the disease process and drug effectiveness. If multiple doses are employed, as preferred, the frequency of administration will depend, for example, on the type of host and the type of angiogenesis-mediated disease or disorder. One skilled in the can ascertain upon routine experimentation the appropriate route and frequency of administration in a given subject which are most effective in any particular case. Suitable doses and dosage regimens can be determined by conventionally known range-finding techniques. Generally, treatment is initiated with smaller dosages, which are less than the optimal dose of the compound. Thereafter, the dosage is increased by small increments until the optimal effect under the circumstances is obtained.

The therapeutic compositions for use in embodiments of the invention generally include carriers. These carriers may be any of those conventionally used and are limited only by the route of administration and chemical and physical considerations, such as solubility and reactivity with the therapeutic agent. In addition, the therapeutic composition may be formulated as polymeric compositions, inclusion complexes, such as cyclodextrin inclusion complexes, liposomes, microspheres, microcapsules, and the like, without limitation. The therapeutic composition can be formulated as a pharmaceutically acceptable acid addition salt such as, but not limited to, those derived from mineral acids such as, but not limited to, hydrochloric, hydrobromic, phosphoric, metaphosphoric, nitric and sulfuric acids, and the like, and organic acids, such as, but not limited to, tartaric, acetic, citric, malic, lactic, fumaric, benzoic, glycolic, gluconic, succinic, and arylsulfonic, such as p-toluenesulfonic, and the like.

The pharmaceutically acceptable excipients described herein, for example, vehicles, adjuvants, carriers or diluents, are well known and readily available. It is preferred that the pharmaceutically acceptable carrier be one which is chemically inert with respect to the therapeutic composition and one that has no detrimental side effects or toxicity under the conditions of use.

The choice of excipient will be determined, in part, by the particular therapeutic composition, as well as by the particular method used to administer the composition. Accordingly, there is a wide variety of suitable formulations of the pharmaceutical composition used in the embodiments of the invention. For example, the non-limiting formulations can be injectable formulations such as, but not limited to, those for intravenous, subcutaneous, intramuscular, intraperitoneal injection, and the like, topical ointment formulations for application to the skin, including patches, corneal shields and ophthalmic ointments, and oral formulations such as, but not limited to, liquid solutions, including suspensions and emulsions, capsules, sachets, tablets, lozenges, and the like. Non-limiting formulations suitable for parenteral administration include aqueous and non-aqueous isotonic sterile injection solutions, including non-active ingredients such as antioxidants, buffers, bacteriostats, solubilizers, thickening agents, stabilizers, preservatives, surfactants, and the like. The solutions can include oils, fatty acids, including detergents and the like, as well as other well known and common ingredients in such compositions, without limitation.

Diagnostics

The present invention further encompasses methods and compositions for the diagnosis of angiogenesis-mediated diseases. Thus, in a preferred embodiment, the present invention for the first time enables genetic testing for VG5Q mediated diseases, including but not limited to Klippel-Trenaunay syndrome, based on the herein disclosed genomic structure of VG5Q. PCR primers can be designed for the amplification of any or all exons of VG5Q for genetic testing. A probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3. Preferably, an oligonucleotide is less than about 200, 150, 120, or 100 nucleotides in length.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO: 2. The reverse primer can anneal to the ultimate codon, e.g., the codon immediately before the stop codon, e.g., the codon encoding amino acid residue 714 of SEQ ID NO:2. PCR using the primers provided by the present invention can be utilized to amplify any region of VG5Q DNA in vitro to identify deletions, point mutations, or translocations involving VG5Q DNA. Other genetic testing procedures may readily be performed by a person of skill based on the instant disclosure.

In another preferred embodiment the present invention provides VG5Q probes. Probes are nucleic acids corresponding to a gene or sequence of interest, that can be labelled either radioactively or with some other detectable molecule, such as biotin, digoxygenin or fluorescein. As stretches of DNA or RNA with complementary sequences will hybridize, a probe will label viral plaques, bacterial colonies or bands on a gel that contain the gene of interest, VG5Q. The VG5Q probes of the invention are at least 10, 12, 15, 18, 20 and less than 200, more preferably less than 100, or less than 50, nucleotides in length. Their sequences should be identical, or differ by 1, or 2, or less than 5 or 10 nucleotides, from a VG5Q sequence disclosed herein.

The antibodies previously described and provided by the present invention that are immunoreactive with VG5Q, or peptide fragments thereof, are also useful in diagnostic methods and kits to detect or quantify VG5Q proteins present in a given sample. Results from these tests can be used to diagnose or predict the occurrence or recurrence of angiogenesis-mediated diseases or disorders. Anti-VG5Q may also be used to purify VG5Q proteins from crude extracts and the like.

Anti-VG5Q antibodies may be used to quantify VG5Q using immunoassays known in the art including, but not limited to, radioimmunoassay (RIA), enzyme-linked immunosorbent assay (ELISA), Western blotting, immunofluorescence, immunoelectron microscopy. Accordingly, the antibodies specific for VG5Q may also be used in diagnostic kits to detect the presence and quantity of VG5Q which is diagnostic or prognostic for the occurrence or recurrence of cancer or other diseases mediated by angiogenesis.

Animal Models

The invention also provides an animal model for KTS. VG5Q mutation E133K is associated with vascular disease KTS. Mutation E133K causes increased angiogenesis and acts by a gain-of-function mechanism, mice that express wild type VG5Q or mutant E133K VG5Q may recapitulate the vascular phenotype seen in humans. These mice may be express VG5Q or mutant E133K VG5Q constitutively or in a temporal or tissue-specific conditional manner. Further, the knockout mouse with a targeted disruption of VG5Q gene is useful for examination of the physiological role of VG5Q. Knock-in mouse lines may be created to determine the effect of other identified VG5Q mutations. Cells and tissues from these mouse models are used to study various angiogenic therapies and angiogenic mechanisms.

EXAMPLES

The following examples are provided to better illustrate the claimed invention and are not to be interpreted as limiting the scope of the invention. To the extent that specific materials are mentioned, it is merely for purposes of illustration and is not intended to limit the invention. Unless otherwise specified, general cloning procedures, such as those set forth in Sambrook et al., Molecular Cloning, Cold Spring Harbor Laboratory (2001), Ausubel et al. (eds.) Current Protocols in Molecular Biology, John Wiley & Sons (2000) are used. One skilled in the art may develop equivalent means or reactants without the exercise of inventive capacity and without departing from the scope of the invention.

It will be understood that many variations can be made in the procedures herein described while still remaining within the bounds of the present invention. Likewise, it is understood that, due to the degeneracy of the genetic code, nucleic acid sequences with codons equivalent to those disclosed with encode functionally equivalent or identical proteins as dis-

Example 1

Identification of the KTS Susceptibility Gene—VG5Q

A positional cloning approach was employed to investigate the pathogenic mechanism of KTS and to identify its susceptibility gene. A translocation of t(5;11)(q13.3; p15.1) has previously been found to be associated with KTS. Whelan, A. J., et al. Klippel-Trenaunay-Weber Syndrome Associated With a 5:11 Balanced Translocation. *Am. J. Med. Genet.* 59:492-494 (1995). PCR analysis with somatic cell hybrids containing only the derivative chromosome 5 (hybrid H7) or the derivative chromosome 11 (hybrid H34) defined the precise locations of the two translocation breakpoints, thus allowing for the identification of the genes close to the breakpoints. Genomic sequences generated from BACs (FIG. 2a) were used for BLAST analysis to identify ESTs (expressed sequence tags) in the NCBI databases. At the 5q13.3 breakpoint region, five overlapping ESTs (HSU84971, AI939311, AA311507, AI925946, and AI037948) were identified that showed identity to genomic DNA sequences. Isolation and characterization of the novel gene: The full length novel VG5Q cDNA (4,049 bp) was cloned by RACE and RT-PCR. The longest open reading frame spans 2,145 bp and encodes a novel protein with 714 amino acids with a forkhead-associated (HA) domain and a G-patch domain (amino acids 435 to 508, and 619 to 663, respectively, FIG. 2 c) The FHA domain may be involved in phospho-dependent protein-protein interactions and G patch domains have been implicated as RNA-interacting modules. The 3'-end of VG5Q was cloned by 3'-RACE and identification of cDNA clones. The KTS translocation breakpoint is located in the promoter region of VG5Q. The intron-exon boundaries of the human VG5Q gene were mapped and are described in Table 1:

Construction of somatic cell hybrids. Somatic cell hybrids were derived from the blood sample of the t(5;11)(q13.3; p15.1) translocation patient, as described in Jackson, C. L. Construction of somatic hybrids. *Current Protocol in Human Genetics* (ed. Dracopoli, N.C.) p. 3.2.1-3.3.29 (John Wiley & Sons, Inc., New York, 1996).

Long PCR and sequencing. Long PCR was carried out using the rTth DNA polymerase, XL (PE Applied Biosystems, Foster City, Calif.) according to the manufacturer's instructions. Sequencing of plasmids and PCR products was performed by BigDye™ Terminator Cycle Sequencing using an ABI 3100 Genetic Analyzer (Applied Biosystems, Foster City, Calif.).

Typing of polymorphic markers and STSs (Sequence Tagged Sites). Polymorphic markers and STSs on chromosome 5q13.3 and 11p15.1 were identified by searching available databases from the Genethon, the Cooperative Human Linkage Center (CHLC), GDB, the MIT Genome Center, the Stanford Genome Center, and NCBI GeneMap98. Amplification of markers and STSs were carried out using standard PCR protocols. PCR products were analyzed by electrophoresing through 6% polyacrylamide gels or 2% agarose gels.

Isolation of YACs, PACs and BACs. YACs were identified by searching the databases from the Whitehead Institute/MIT Genome Center, the NCBI, and the Genethon with STSs and other markers mapped near the translocation breakpoints. The YAC clones were purchased from Research Genetics (Huntsville, Ala.). The PAC, and BAC clones were isolated from human PAC/BAC libraries (Genome Systems, St. Louis, Mo.). PCR primers from STSs, ESTs and other markers at the translocation breakpoints were used to isolate PAC and BAC clones from the libraries by a PCR-based screening assay of pooled libraries according to the manufacturer's instructions. The end sequences of each PAC or BAC were directly determined by direct cycle sequencing (Wang Q. & Keating. M. T.

TABLE 1

Genomic Structure of hVG5q: intron-exon boundaries in human VG5Q gene

| Acceptor sites Intron/Exon | Exon (bp) | Donor sites Exon/Intron |
|---|---|---|
|  | 1 (511) | AGCTCCGCACGCAG/gtgcgcggtcctcc |
| cttgttttctctcag/GTGGAAGAACTCA | 2 (103) | TTGGTCAATCTCAG/gtatttagctcata |
| attttttttgctacag/ATTATTTTTATCA | 3 (203) | CCTCAAATTCACAG/gtaataaaatgcta |
| ctatatcttttatag/GAGCCAGCATCTG | 4 (165) | TCTATTATGATTCT/gtaagtatctcaga |
| tcttgactttcaaag/GAAAATCAACTCT | 5 (189) | CAAATGAGGAAAAG/gtaatgtctttaca |
| cccaccttctccag/GATTTGAACTCAG | 6 (331) | TAGTGAGGATGAAG/gtgagtaaataatc |
| ttctttccttggcag/ATGAAGACAAAAT | 7 (112) | GCTACAATTGGAAG/gtaaaatggttaat |
| tacttaactctgcag/AGAAAAGGATATG | 8 (52) | TTGGTGTCAGTAAG/gtaagctctttgat |
| atttcactttctaag/TTTCATGCAGAAA | 9 (102) | AACAGATTCTTCAG/gtgagtgtatatgt |
| atgtttccctctag/CCGAAAACTAAAT | 10 (166) | AGATGAATCTTTTG/gtatgtgaaacaga |
| cttttttttcttcag/TTGGTCCAACACT | 11 (83) | AATATGGTTTACAG/gtgaggatgttgaa |
| tttgtgtttattaag/AATACAGAATACG | 12 (128) | GCATCTGTTCATTC/gtaagttttgaatt |
| taatattccttaaag/TGAAATTACTGAT | 13 (100) | GAATGAAAACGCCG/gtaagacttggatt |
| aactttggtaacag/ATCCAGCTTCAGC | 14 (1804) |  |

Biotechniques 1994, 17:282, 284). STSs were generated based on these insert end sequences and used to identify adjacent and overlapping PAC/BAC clones (chromosome walking). The same process was repeated until the genomic region of interest was completely covered by PACs/BACs.

Identification and cloning of genes. Genes at the translocation breakpoint regions were identified by database searches for sequences homologous to cloned genes or ESTs. Genomic DNA sequences generated from PACs, BACs, or subcloned plasmids at the two translocation breakpoint regions were submitted to the BLAST server at NCBI for BLAST analysis of the GeneBank and EST database. Homology to a known gene or EST indicates the presence of a candidate gene. VG5Q was identified by homology to genomic DNA sequences derived from BAC 18o21 at the 5q13.3 translocation breakpoint to ESTs in the GenBank database. The full length of cDNA of VG5Q was cloned by the 3'-Race with the Marathon-Ready cDNA kit (Clontech, Palo Alto, Calif.), and RT-PCR.

Example 2

Expression of VG5Q in Endothelial Cells

Figures 5A, 5B, 5C, 5D, 5E:
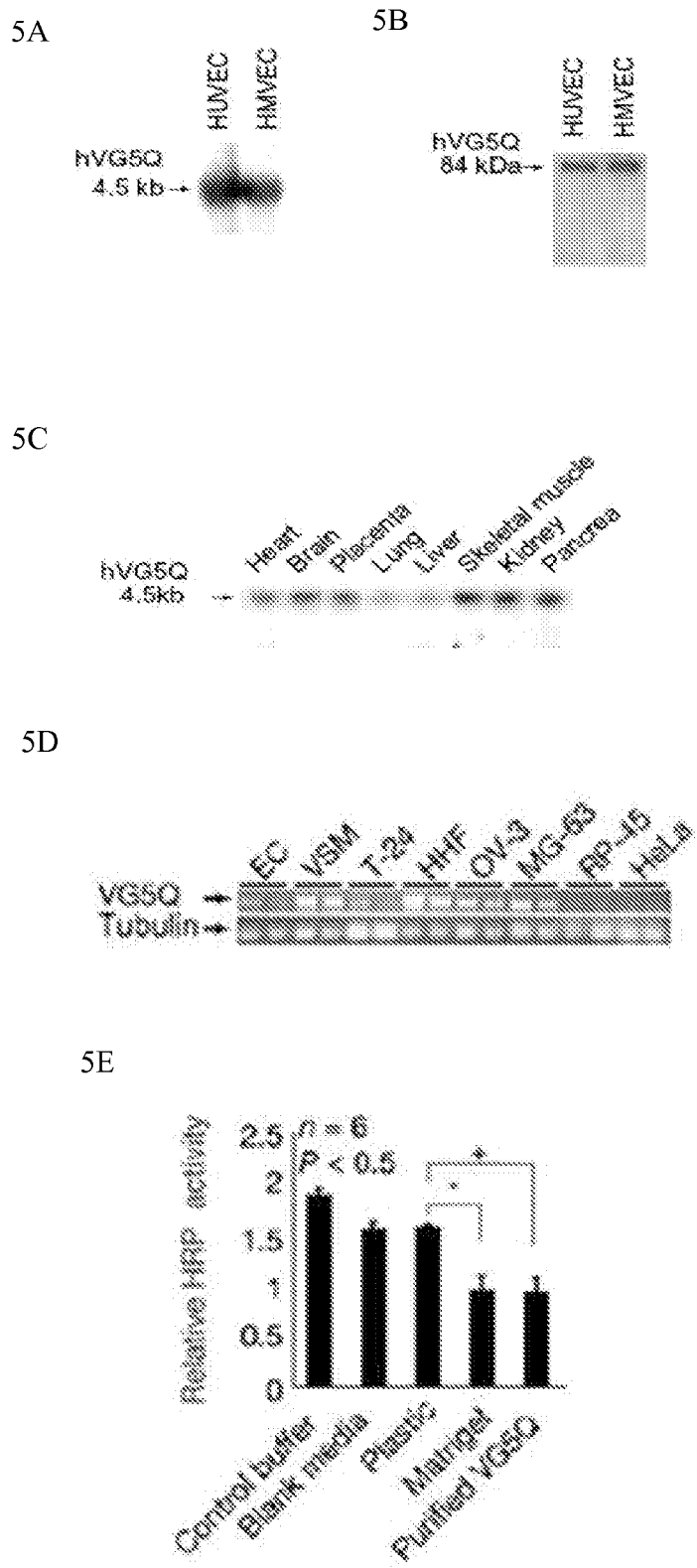
FIG. 5(a) depicts the Northern blot analysis of VG5Q expression in human endothelial cells.
FIG. 5(b) depicts the Western blot analysis of VG5Q expression in human endothelial cells.
FIG. 5(c) depicts the tissue expression pattern of VG5Q. Northern blot analysis reveled a 4.5-kb VG5Q mRNA in human tissues including the heart, brain, placenta, lung, liver, skeletal muscle, kidney and pancreas.

Endothelial expression of VG5Q: Northern blot analysis revealed a single 4.5 kb transcript in human microvascular endothelial cells (HMVEC, FIG. 5a). VG5Q was ubiquitously expressed in all tissues examined (FIG. 5c), presumably due to the presence of blood vessels embedded in these tissues. Western blot analysis with a polyclonal antibody against a synthetic polypeptide immunogen based on a unique VG5Q sequence recognized a predicted 87 kDa protein present in extracts of human endothelial cells (FIG. 5b). RT-PCR analysis revealed expression of VG5Q mRNA in different cell lines (FIG. 5d).

Using immunostaining with the anti-VG5Q antibody, it was found that VG5Q was expressed in blood vessels embedded in mouse heart, tail, and kidney tissues, but not in non-vascularized areas. The endothelial cell layer was clearly distinguishable from the smooth muscle cell in the sections, and VG5Q signal co-localized with CD31 signal (endothelial cell-specific) but not with α-actin (smooth muscle cell-specific). It was therefore concluded that VG5Q encodes a novel vascular protein.

Northern blot analysis. Total RNA was isolated from cultured cells, including human primary cultured microvascular endothelial cells, and 20 μg was used for Northern blot analysis. RNA was fractionated through 1% agarose (2M formaldehyde) in 1×MOPS buffer, and transferred to Nylon membranes. A multiple tissue Northern filter (Human MTN blot, 7760-1) was purchased from Clontech (Palo Alto, Calif.). The filters were probed using radioactively labeled ($\alpha$-$P^{32}$-dCTP) full length VG5Q cDNA.

Western blot analysis. A polyclonal antibody against human VG5Q was developed using a synthetic peptide immunogen, LAQLRRKVEKLERELRSC, depicted in SEQ ID NO:7 as the immunogen by QCB, Inc. (Hoplinton, Mass.). The immunogen sequence corresponds to a unique portion of the N-terminus of VG5Q. The immunogen sequence did not match any other sequences in the databases, suggesting the specificity of the VG5Q antibody. Other polyclonal antibodies have been developed against synthetic peptide immunogens, specifically human 'N'-CEYEDEKTLKNP-KYKDRAGKR-'C' (SEQ ID NO: 49), mouse 'N'-CHSGNVKKKARTDTSHKS-'C' (SEQ ID NO: 50), and mouse 'N'-CLIQNKSKKHWDKARE-'C' (SEQ ID NO: 51). Unless otherwise indicated, the antibody used in experiments was the polyclonal antibody against SEQ ID NO: 7. Rabbits were immunized with the immunogen and sera from immunized rabbits were tested for antibody against the peptide by ELISA. The antibody was purified using standard protocols. Western blot analysis was performed with the VG5Q antiserum as the primary antibody. Secondary antibodies, horseradish peroxidase-conjugated donkey anti-rabbit IgG (NA 934, Amersham Pharmacia Biotech, Inc., Piscataway, N.J.), were used to visualize the protein signals.

Example 3

KTS is Associated with a Mutation in VG5Q

Figures 4A, 4B:
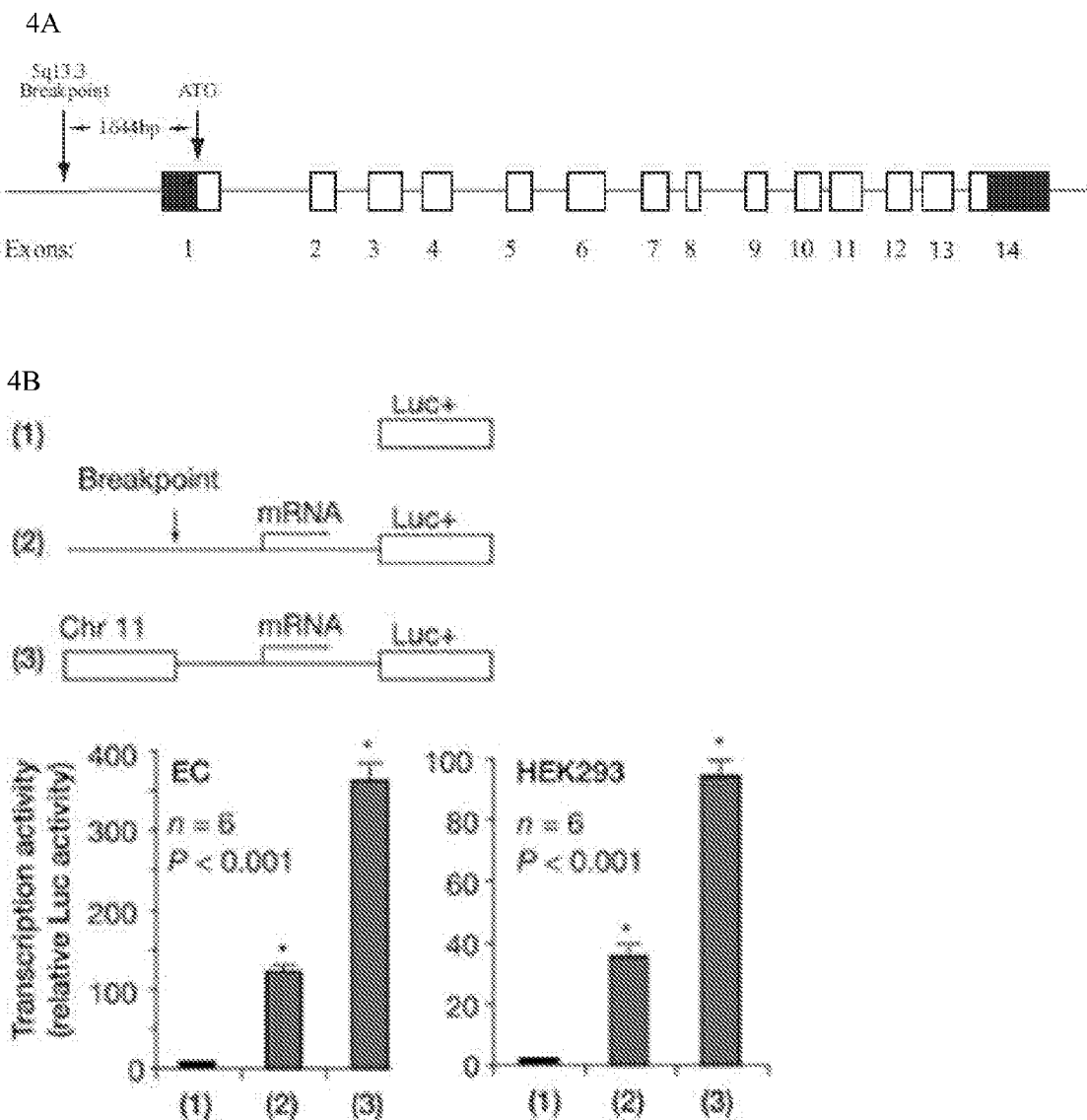
FIG. 4(a) depicts the genomic organization of the human VG5Q gene. VG5Q consists of 14 exons. The chromosome 5q13.3 breakpoint is located in the promoter region of VG5Q, 1641 base pairs upstream from translational start codon ATG or 1343 base pairs from the start of the cDNA sequence.
FIG. 4(b) depicts the t(5;11)(q13.3;q15.1) translocation associated with KTS affecting the expression of VG5Q. Luciferase reporter genes were created to determine the effect of translocation t(5;11) on expression of VG5Q. Construct i the pGL3-Basic vector with the lucerifase gene (luc+); Construct ii, wild-type VG5Q promoter fused to the luceriase gene (luc+) in pGL3-Basic with the 5q13.3 breakpoint indicated; Construct iii, the junction fragment derived from derivative chromosome 11 fused to luc+. The luciferase activity of the vector was set to 1 arbitrarily. Results represent mean of triplicate cultures +/− standard deviation. Values are average of three independent experiments. EC, human umbilical vein endothelial cells; HEK293, HEK293 cells.
Figures 4C, 4D, 4E:
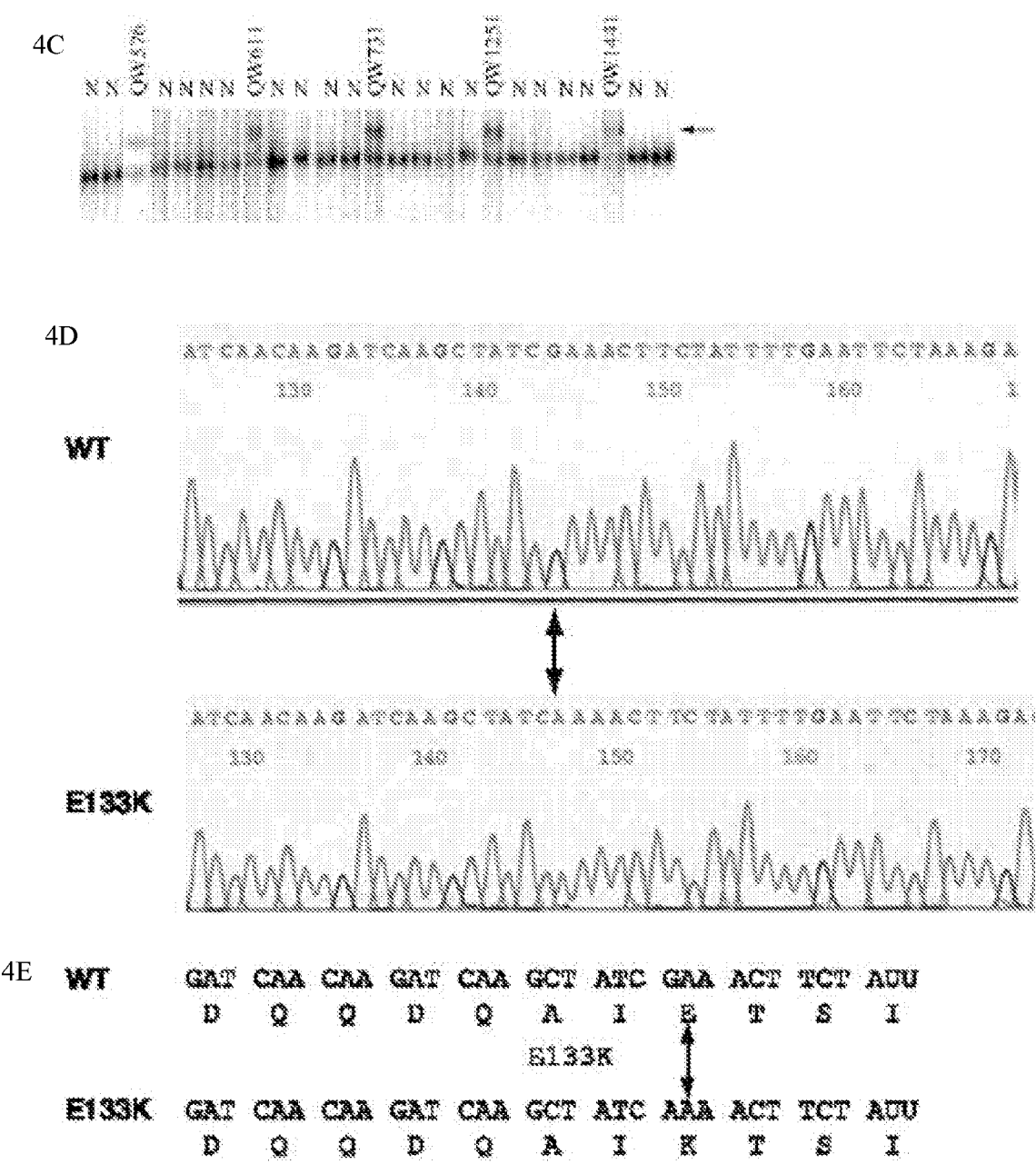
FIG. 4(c) shows the results of single strand conformation polymorphism (SSCP) analysis. The aberrant SSCP conformer is indicated by an arrow. N, normal; QW576, QW611, QW731, QW1251, and QW1441, five independent patients affected with vascular disease KTS. The primers for SSCP are 5'-TGT TTA AAT GCC AGT GTT TTG TAG-3' (forward) (SEQ ID NO: 41) and 5'-GAC AGG TTC TTG GGC ATC AAC-3' (SEQ ID NO: 42 (reverse)).
FIG. 4(d) represents the sequence analysis of the normal (WT) and aberrant (E133K) SSCP conformers revealing a G to A substitution at codon 133 of VG5Q.
FIG. 4(e) represents the G to A mutation at codon 133 causes a non-conservative substitution of a negatively charged glutamic acid residue by a positively charged lysine residue (E133K). Mutation E133K was not identified in 200 normal controls.

Because VG5Q is the only gene located near the two breakpoints of translocation t(5;11) associated with KTS it was considered a candidate gene for the disease. To test whether VG5Q is a KTS gene, it was determined whether the t(5;11) translocation affects the expression of VG5Q. The 5q13.3 translocation breakpoint is located in the promoter/regulatory region of VG5Q and is only 1343 bp upstream from the beginning of VG5Q cDNA (FIG. 4 a). The VG5Q promoter/regulatory region was fused to the luciferase gene (FIG. 4 b, construct ii). A luciferase reporter gene was also constructed for the translocation junction fragment from derivative chromosome 11, which precedes the VG5Q coding region in the KTS patient with translocation t(5;11), as shown in FIG. 4 b; construct iii. VG5Q promoter with the translocation junction fragment (construct iii) increased its expression by 3 fold in human umbilical vein endothelial cells (HUVEC) and by 2.7 fold in human embryonic kidney cells HEK-293 as compared with the wild-type VG5Q construct (FIG. 4 b). It was therefore concluded that the t(5;11) KTS translocation is a functional genetic defect that leads to overexpression of VG5Q.

Population genetics-based association of VG5Q with KTS: To confirm that VG5Q causes susceptibility to KTS, a mutational analysis for VG5Q with 130 KTS patients. VG5Q consists of 14 exons that span approximately 40 kb (FIG. 4 a), and all exons and exon-intron boundaries of VG5Q (see Table 1, supra) were screened for KTS-associated mutation using single strand conformation polymorphism (SSCP) and sequence analysis. PCR primers used to define VG5Q mutations are found in Table 2. A single non-conservative VG5Q mutation, E133K, was identified in five KTS patients, and this mutation results in substitution of a negatively charged glutamine residue for a positively charged lysine residue (FIG. 4 d, e). Mutation E133K was not detected in 200 normal subjects. A statistically significant association was established between E133K of VG5Q and KTS (P=0.009).

TABLE 2

PCR Primers Used to Define VG5Q Mutations

| Exon | Forward Primer (5' to 3') | Reverse Primer (5' to 3') |
|---|---|---|
| 1 | GAACGCAGCCCCTCCGCGGCGACGA (SEQ ID NO: 13) | CTGGATGGGGCGCGGGGCTGAGGAG (SEQ ID NO: 14) |

TABLE 2-continued

PCR Primers Used to Define VG5Q Mutations

| Exon | Forward Primer (5' to 3') | Reverse Primer (5' to 3') |
|---|---|---|
| 2 | GATTTCTTTTTCCTAAAGCCTTGTTT (SEQ ID NO: 15) | GTGTTAGCATATCCTCACTATAAGC (SEQ ID NO: 16) |
| 3 | CACTTCATTTTTTGCTACAGATTAT (SEQ ID NO: 17) | CATTTTATTACCTGTGAATTTGAGGC (SEQ ID NO: 18) |
| 4 | GCTTTTGTCTTATTTGGCATGA (SEQ ID NO: 19) | TGACAGAGGGAGACTGTCTCAA (SEQ ID NO: 20) |
| 5 | TTTATTTTTTCTTGACTTTCAAAGGA (SEQ ID NO: 21) | TTGTAAAGACATTACCTTTTCC (SEQ ID NO: 22) |
| 6 | TTACCAGACTGGGCTATTTACTT (SEQ ID NO: 23) | TAAGAGTATTCTCCCCTGTTCCCT (SEQ ID NO: 24) |
| 7 | AAGCCTTTCTGAAATAACTGAAA (SEQ ID NO: 25) | CCTCCTAGTTATCCCTATGAAGTTC (SEQ ID NO: 26) |
| 8 | AATATAAAAAATTACATCTAGGGGAC (SEQ ID NO: 27) | TTAAAGACACTTTACTTAACTCTGCA (SEQ ID NO: 28) |
| 9 | AACACATATACACTCACCTGAAGAA (SEQ ID NO: 29) | GCTTGATTTCACTTTCTAAGTTTCATG (SEQ ID NO: 30) |
| 10 | TGTAAAATGTTTCCCCTCTAGCC (SEQ ID NO: 31) | CCACATTTAATCTGTTTCACATACC (SEQ ID NO: 32) |
| 11 | ATACAGCTTAACAAATGAAACAATA (SEQ ID NO: 33) | GAAAGGACATCATCACAACCCAATA (SEQ ID NO: 34) |
| 12 | AAGGATGTTTCGAGCCACTGTA (SEQ ID NO: 35) | GTTTATAGAGGCCACATTGAATCAT (SEQ ID NO: 36) |
| 13 | CACGGTAAATGTCTGCTCTAGGAATAA (SEQ ID NO: 37) | GTTAGGTAATGCCAAGCGGTTTTCT (SEQ ID NO: 38) |
| 14 | ATAGTTCCCCTGTGCTGCTGATTCTT (SEQ ID NO: 39) | CTCTAAAATAAGTCCTCTGCTCAAC (SEQ ID NO: 40) |

Isolation of genomic DNA and mutation analysis. Genomic DNA was prepared from whole blood with the DNA Isolation Kit for Mammalian Blood (Roche Diagnostic Co., Indianapolis, Ind.). SSCP analysis was carried out as described previously. (Chen, Q. et al. Nature 1988, 392: 293-6; Wang, Q. et al., Hum. Mol. Genet. 1995, 4: 1603-7; Wang Q., et al., Cell 1995, 80: 805-11; Wang, Q. et al., Nat. Genet. 1996 12:17-23). Normal and abnormal SSCP bands were isolated from gels, rehydrated, re-amplified with original PCR primers, and sequenced directly with an ABI 3100 Genetic Analyzer and BigDye™ terminator cycle sequencing.

Transcriptional assay. The promoter region of VG5Q was fused to the luciferase gene in pGL3-Basic vector (Promega, Madison, Wis.), resulting in a reporter gene VG5Qp-luc+. A similar reporter gene VG5Qp-luc+(der 11) was constructed for the translocation junction fragment from derivative chromosome 11. Transfections were performed with 2 μl Lipofectamine 2000 (Invitrogen; Carlsbad, Calif.) and 2 μg of DNA for a reporter gene when cells grew to 80-90% confluence. The reporter gene was co-transfected with 50 ng of internal control plasmid pSV-β-galactosidase (Promega, Madison, Wis.). Cells were harvested and lysed 24 hours after transfection. Luciferase assay was performed using the Luciferase assay system (Promega, Madison, Wis.) according to the manufacturer's instructions. β-galactosidase activity expressed from pSV-β-galactosidase was used to normalize transfection efficiency. The results shown are the mean±standard deviation from at least three independent experiments and each experiment was performed in triplicate.

Example 4

Effect of VG5Q Mutation on Vascular Development

Figure 6:
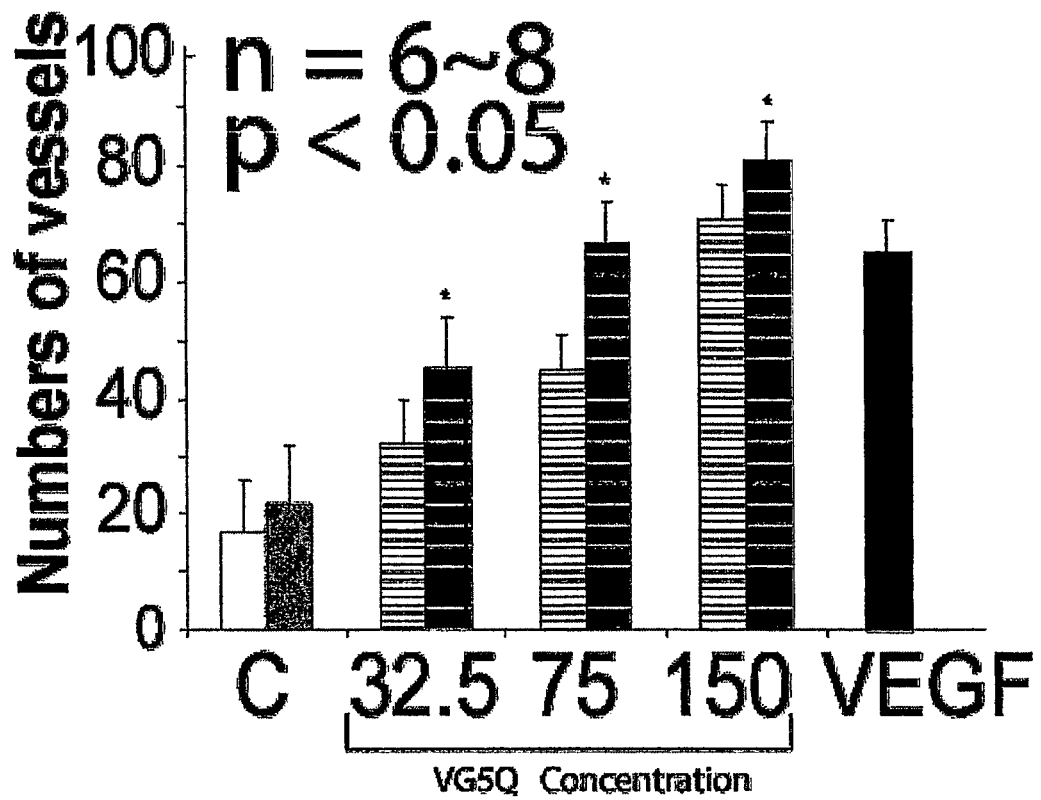
FIG. 6 shows the chicken chorioallantroic membrane (CAM) assay depicting angiogenesis mediated by wild type and mutant E133K VG5Q protein. The number of vessels is depicted on the Y axis, the angiogenic mediator is depicted on the X axis. "c" is the negative control set, wherein the white bar is buffer, and the grey bar is BSA. "VEGF" is the positive control. "32.5", "75", and "150" refer to concentrations in ng/μl of wild-type VG5Q protein (white striped bars) or VG5Q E133K mutant protein (black striped bars). "n=6-8" refers to the numbers of CAM assays performed per set.

The E133K mutation in VG5Q increases angiogenesis: Because VG5Q mutations cause vascular malformations associated with KTS, and VG5Q protein undergoes dynamic redistribution and secretion during angiogenesis, it was determined whether VG5Q can directly function as an angiogenic factor. With the chick chorioallantoic membrane (CAM) assay, it was found that the purified, wild type VG5Q protein promoted strong angiogenesis as shown by the newly formed, radiated vessels on the CAM. Similar results were observed around the discs which were spotted with VEGF (100 ng/μl) as a positive control. VG5Q appeared to be as potent as VEGF in promoting angiogenesis. Marked differences in angiogenesis were observed between wild type and mutant VG5Q with the E133K substitution. Mutant VG5Q protein produced a significantly more potent angiogenic factor than the wild type protein (wild type vs. mutant: at a concentration of 37.5 ng/μl; 75 ng/μl, and 150 ng/μl). These results are summarized in graphic form a FIG. 6. These results demonstrate that mutation E133K of VG5Q is a functional mutation that acts by a gain-of-function mechanism (increased angiogenesis). The gain-of-function nature of VG5Q mutation E133K is consistent with the earlier finding that the KTS translocation increases expression of VG5Q. These data also indicate that similar to VEGF, VG5Q is a potent angiogenic factor.

The full-length wild type VG5Q cDNA was cloned into a bacterial expression vector pET-28b (Novagen), resulting in expression construct pET-28VG5Q-wt for 6His-tagged VG5Q. The VG5Q mutation was introduced into pET-28VG5Q-wt using PCR-based site-directed mutagenesis, resulting in pET-28VG5Q-mt. The expression constructs were transformed into *E. coli*, BL21(DE3) Star, and 6His-VG5Q protein was purified using a Ni-NTA agarose column according to the manufacturer's instructions (QIAGEN). The eluted protein was dialyzed, and quality of purification was examined by SDS-PAGE and Western blot analysis. Chorioallantoic membrane (CAM) assay. Fertilized chicken eggs were purchased from the University Farm, Case Western Reserve University. The eggs were incubated for 4 days at 37° C. and then opened, and the embryos were incubated in Petri dishes (100 mm diameter) at 37° C. with 100% humidity. After 4 days, round glass cellulose fibers (3 mm diameter) soaked with either VEGF (100 ng/μl), or with different concentrations of purified wild type or mutant VG5Q (37.5 ng/μl, 75 ng/jμl and 150 ng/μl). The control discs were soaked with the buffer that was used for dialysis and dissolving of VG5Q protein (50 mM Tris-HCl, 150 mM NaCl and 2 mM $MgCl_2$, pH 7.4). The newly formed vessels were examined and visualized with a photomicroscope (Leica MZFLIII) and Spot Advanced software (Diagnostic Instruments, Inc.).

Example 5

Subcellular localization and secretion of VG5Q: The VG5Q protein undergoes a dramatic change of localization during endothelial tube development: Immunostaining was also used to investigate the subcellular localization of VG5Q protein in HMVEC. VG5Q protein expression was detected in both the cytoplasm and nucleus and the strongest expression signal was observed in the cytoplasm: No signal was detected in the control when normal rabbit serum was substituted for the anti-VG5Q. When immunostained endothelial cells were visualized using a confocal microscopy, VG5Q protein was again localized mainly in the cytoplasm and a weak signal was also observed in the nucleus.

A dramatic change of the distribution pattern of VG5Q protein was observed during the process of tube formation in an in vitro model of angiogenesis where HMVEC and HUVEC were plated onto matrigel. When cells were cultured on matrigel for one hour, VG5Q protein began to redistribute toward moving towards the cell periphery and was also detected outside the cell. The dynamic re-distribution of VG5Q at this stage resembles the secretion pattern of other released proteins (Pfeffer, S. Cell 2003, 112: 507-17; Wang, H., et al., Biochem Biophys Res Commun 2002, 299: 703-9 (2002)). At 4 hours, endothelial tubes were formed, and VG5Q protein was present inside tubes as well as outside of the tubes. In newly formed tubes, VG5Q protein was localized between cells and appeared to bridge the cells together. After the tubes were formed (24 hours), VG5Q protein within the nucleus completely disappeared. Immunostaining in mouse heart, tail, and hindlimb tissue also revealed that VG5Q protein is not present in the nucleus in mature blood vessels.

VG5Q is secreted during angiogenesis: To confirm that VG5Q is secreted during angiogenesis, a competitive ELISA assay was carried out. As shown in FIG. 5(*e*) the media from matrigel cultures (angiogenesis) contain secreted VG5Q, which leads to significantly reduced absorbance in the competitive ELISA assay compared to the media from non-angiogenesis cultures (p=0.009). These results indicate that angiogenesis accompanies dynamic re-distribution and secretion of VG5Q protein. The molecular mechanisms for trafficking of VG5Q remain to be established, but VG5Q may be secreted via a non-classical secretory pathway like the angiogenic factor FGF-2 and other proteins such as galectin-3, nuclear protein HMGB1, and thioredoxin that lack signal sequences (Rubartelli, A, et al, J Biol Chem 1992, 267:24161-4); Rubartelli, A et al., Embo J 1990, 9: 1503-10); Mignatti, P et al., J Cell Physiol 1992, 151: 81-93); Zhu, W. Q. & Ochieng, J., Cancer Res 2001, 61: 1869-73).

Immunofluorescent studies were performed with a polyclonal anti-VG5Q antibody. Endothelial cells were plated at a density of 200,000 cells/$cm^2$ on Lab-Tek II chamber slides (Nalge Nunc International, Naperville, Ill.) coated with or without matrigel. Following 1, 4 and 24 hours of plating, the cells were washed with PBS and fixed with 4% paraformaldehyde. Intracellular localization of VG5Q protein was detected by immunostaining with anti-VG5Q as the primary antibody followed by anti-rabbit IgG conjugated to Texas Red (Red). The nucleus was stained with DAPI (blue). To determine the specificity, a control group of culture were incubated with normal rabbit serum instead of VG5Q primary antibody. Tissue immunostaining was carried out with 6 μm cryo-sections from mouse heart, tail and kidney.

For competitive ELISA analysis HUVEC were plated on Lab-Tek II chamber slides coated with or without matrigel (in vitro angiogenesis) for 4 hours. The media were collected, incubated for 30 min with an optimum concentration (200 ng/ml) of anti-VG5Q antibody (determined experimentally with antigen), and transferred to wells coated with peptide immunogen (1 μg/ml, 6 replicates). The bound antibody was detected by the secondary HRP-conjugated donkey anti-rabbit IgG, chromogenic reaction, and absorbance reading of the wells. The negative controls include media only and PBS buffer, and the positive control is the purified VG5Q protein.

Example 6

Statistical Analysis

Figure 7:
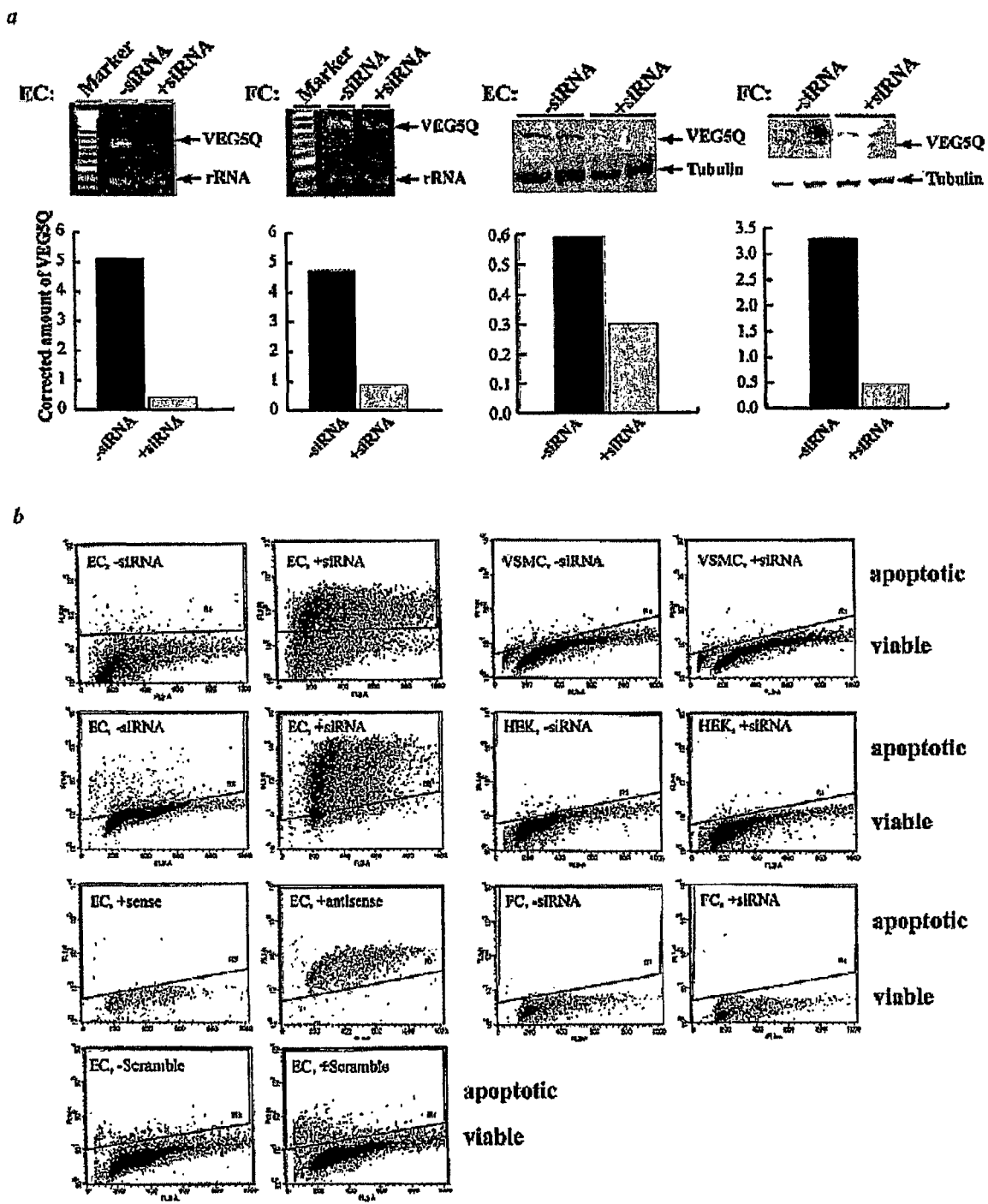
FIG. 7 shows that suppression of VG5Q expression causes endothelial cell apoptosis.

Because KTS is a sporadic disease, the population-based association study is the only feasible genetic analysis to determine whether a candidate gene is the KTS susceptibility gene. Thus, an association study was performed with 130 KTS cases and 200 comparable controls (Table 3). Explicit attempts were made to ascertain casea and controls from the same racial population (Caucasians) to control racial confounding. Mutational analysis of VG5Q revealed a SNP P698T in the C-terminus (exon 14) that is present in both KTS patients (28.9%) and normal controls (24.4%). Genotypic heterozygosity and allelic frequency for SNP P698T between cases and controls were compared using Fisher's exact test. The two-tailed Fischer's exact test was used to evaluate the association between genetic variants (mutation or SNP) and KTS. The statistical P value corresponds to the chance that random sampling would result in an association as strong as (or stronger than) observed in the experiment under the hypothesis that no association between KTS status and the genetic variant exists. ANOVA, together with Scheffe's Multiple-comparison test, was used to evaluate the differences among the groups in ELISA analysis. No significant difference was observed for either heterozygosity (two tailed P=1.00) or allelic frequency (two tailed P=0.32), suggesting that the selected cases and controls are comparable. Mutation E133K was identified in five of the 130 KTS patients, but not in 200 controls. A statistically significant association was established between E133K of VG5Q and KTS (P=0.009) body for DNA breaks (apoptotic cells, y-axis) are depicted in FIG. 7(b). Positively stained apoptotic cells with the fluores-

TABLE 3

Tests for matching of cases with controls with population-specific SNPs*

| | Allele Frequency | | | | | | |
|---|---|---|---|---|---|---|---|
| | Reference Population[a] | | Study Population | | | | |
| SNP | Caucasians | African Americans | Case | Control | Δ[b] | LLR[c] | P[d] |
| AT3 ss4387045 | 0.28 | 0.86 | 0.13 | 0.15 | 0.02 | 0.00181 | 0.55 |
| APOA1 ss4387046 | 0.93 | 0.42 | 0.94 | 0.93 | 0.01 | 0.00023 | 0.83 |
| CKM ss4387019 | 0.31 | 0.16 | 0.47 | 0.45 | 0.02 | 0.00093 | 0.64 |
| LPL ss4387026 | 0.49 | 0.97 | 0.50 | 0.48 | 0.02 | 0.00042 | 0.77 |
| MD154 ss4387044 | 0.36 | 0.81 | 0.42 | 0.42 | 0 | 0 | 1.00 |
| VG5Q P698T[e] | N/A | N/A | 0.29 | 0.24 | 0.05 | 0.00446 | 0.32 |
| APOA1 Msp I (GDB55603) | N/A | N/A | 0.50 | 0.46 | 0.04 | 0.00265 | 0.43 |

*Genotyping of population-specific markers and statistical analysis were used to infer population structure of KTS cases and controls. Ancestry informative markers, SNPs AT3, APOAI, CKM, LPL, and MD154, were used[15,29]. Two other SNPs, VG5Q/P698T and APOAI/Msp I (GDB55603), were also used in the analysis.
[a]The allelic frequencies for reference populations are from recent studies for ancestry informative markers[15,29];
[b]Δ: Allelic difference between cases and controls;
[c]LLR: Average Log-Likelihood Ratio[15,29];
[d]P for H$_0$: Δ = 0: p value for the null hypothesis Δ = 0 is obtained by a Chi-squared test.
The cases matches controls in this study design (P > 0.05). Chi-squared tests did not detect deviation from Hardy-Weinberg equilibrium (P > 0.05) except for the apoA1 SNP in the control population. Three homozygotes were detected for the rare allele, which exceeds the expected number of 0.98 for the control population, and could be attributed to the small sample size and rare allele frequency (0.07). Exclusion of these three controls did not affect the results.
The non-synonymous SNP P698T was identified in the C-terminus (exon 14) of VG5Q, and is present in 28.9% of KTS cases and 24.4% of normal controls. Genotypic heterozygosity and allelic frequency for SNP P698T between cases and controls were compared and no significant difference was observed for either heterozygosity (two tailed P = 1.00) or allelic frequency (two tailed P = 0.32). We determined whether VG5Q SNP P698T may have the second-hit effect by genotyping the five KTS patients with mutation E133K. As one patient is homozygous for P allele, two patients are homozygous for T allele, and two patients are heterozygous, SNP P698T may not have the second-hit effect.

Example 7

Silencing of VG5Q Suppresses Endothelial Tube Formation and Causes Apoptosis of Endothelial Cells siRNA is double-stranded RNA that can destroy specific RNA in a sequence-specific fashion. It has been used as a powerful RNA-targeted gene-silencing tool to study the function of various genes. FIG. 7(a) illustrates the reduction of VG5Q expression at both mRNA and protein levels 48 hours after transfection of human microvascular endothelial cells (HMVEC) with siRNA directed against VG5Q. Down-regulation of VG5Q affected endothelial cell proliferation, which is the first step in the process of angiogenesis. The basal level of radio-labeled thymidine uptake (an indicator of cell proliferation) into endothelial cells was reduced more than 40% after 48 hours of siRNA transfection (control 11462+/−289, siRNA 6566+/−303 cpm/dish). This indicated a possible decrease in the number of adherent cells following transfection with siRNA. Microscopic examination revealed a marked increase in the number of floating cells after 48 hours of transfection, suggesting possible apoptosis of endothelial cells following transfection with siRNA.

To examine whether suppression of VG5Q leads to apoptosis in detail, flow cytometric analysis was performed with two different types of endothelial cells, HMVEC and human umbilical vascular endothelial cells (HUVEC). The results of flow cytometric analysis for propidium iodide labeled total cellular DNA (x-axis) and fluorescein labeled anti-BrdU antibody for DNA breaks (apoptotic cells, y-axis) are depicted in FIG. 7(b). Positively stained apoptotic cells with the fluorescein-BrdU antibody are in the upper box, and negatively stained viable cells are in the lower box. Treatment with two different siRNA for VG5Q (siRNA1 or siRNA2) all caused massive apoptosis endothelial cells compared to endothelial cells transfected with control scrambler duplex.

Effect of VG5Q Suppression on Endothelial Cell Tube Formation: The effect of VG5Q suppression on endothelial cell tube formation was then determined. HMVEC were cultured in growth media on plastic Petri dish with or without siRNA for 48 hours. Adherent cells were collected and plated on matrigel at a density of 200,000-cells/cm$^2$ in growth media.

A comparison of FIGS. 8(a)-(c) shows that endothelial tube formation was dramatically reduced following the exposure to siRNA1 (FIG. 8b) and siRNA2 (FIG. 8c) compared with the control group (FIG. 8a). Similar findings were observed with an anti-sense oligonucleotide specific to VG5Q. As FIG. 8(c) shows, endothelial tube formation was not affected when cells were exposed for 48 hours to control scrambler duplex siRNA. Experiments demonstrate that treatment of endothelial cells with siRNA1 (SEQ ID NO: 5) leads to decreased VG5Q RNA (FIG. 8d) and protein (FIG. 8e) expression. This suggests that the observed effect was specific to the suppression of VG5Q. The mechanism for inhibition of tube formation following suppression of VG5Q expression is not known. It is highly likely that reduced VG5Q expression leads to endothelial cell apoptosis, which in turn results in disruption of tube formation. Interestingly, changes in intracellular localization of VG5Q during tube formation were observed in the in vitro model of angiogenesis. This supports a hypothesis that VG5Q may function as a signal molecule mediating endothelial cell-cell interactions during the formation of blood vessels.

Similar experiments were performed to determine whether siRNA against VG5Q could lead to apoptosis in other cells including vascular smooth muscle cells (VSM), human embryonic kidney cells (HEK-293), and fibroblasts (Table 4). Surprisingly, siRNA against VG5Q did not induce apoptosis in vascular smooth muscle cells (VSMC), fibroblasts, HEK-293, bladder cancer cells (T-24), ovarian cancer cells (OV-3), human glioblastoma (U-87), kidney cancer cells (RP-45), or immature human osteoblastic cells (MG-63), although siRNA appeared to be effective in suppressing expression of VG5Q (FIGS. 8d and 8e).

TABLE 4

Apoptosis by VG5Q down-regulation and TRAIL

Apoptosis by siRNAs against VG5Q

| | % of apoptotic cells | | |
|---|---|---|---|
| Cell Type | Scramble control | siRNA-1 | siRNA-2 |
| Endothelial cells | 2.16 | 62.73 | 86.13 |
| Vascular smooth muscle cells | 1.34 | 2.66 | 1.98 |
| Fibroblasts | 0.42 | 0.83 | 0.14 |
| HEK-293 | 1.15 | 0.55 | 1.36 |
| T-24 | 1.09 | 1.92 | 1.50 |
| OV-3 | 1.74 | 3.25 | 3.17 |
| U-87 | 1.74 | 1.50 | 2.35 |
| RP-45 | 1.17 | 0.96 | 1.34 |
| MG-63 | 1.36 | 4.63 | 5.12 |

Apoptosis by antisense oligonucleotide against VG5Q

| | % of apoptotic cells | |
|---|---|---|
| Cell Type | Control sense oligonucleotide | Anti-sense oligonucleotide |
| Endothelial cells | 1.49 | 96.15 |

Cell culture: Human microvascular endothelial cells (HMVEC) and human umbilical vascular endothelial cells (HUVEC) were cultured in the basal media supplemented with hFGF, VEGF, EGF, IGF-1, hydrocortisone, ascorbic acid, gentamycin and 10% fetal bovine serum. The media was replaced every 48 hours. The cells were sub-cultured before reaching confluence to retain their undifferentiated stage. Cells between the stages of passage 6-10 were used for the experiments. Vascular smooth muscle cells and fibroblasts were grown in Dulbecco's minimum essential medium (DMEM) supplemented with 10% fetal bovine serum (Invitrogen, Carlsbad, Calif.).

siRNA was selected 75 bases downstream from the start codon. The selected sequences were blasted against the NCBI database to ensure that the sequences are unique to VG5Q. The sequences for the two selected siRNA are: 5'-AAU UGU CAU UAG AUC ACC CGU-3' (SEQ ID NO: 5, siRNA1) and 5'-AAG AAC AAA AAA AAC UGG GAC-3' (SEQ ID NO: 6, siRNA2). The siRNA was synthesized by Dharmacon Research Inc. (Boulder, Colo.). SiRNA (1.6 nmole) was introduced into HMVEC, HUVEC, VSM, HEK-293 cells and fibroblasts by transfection with Oligofectamine™ (Invitrogen, Carlsbad, Calif.). The endothelial cells were grown to 50%-60% confluency, washed with serum free basal media, and transfected with siRNA and Oligofectamine™. The cells exposed to Oligofectamine™ alone were used as controls. After 48 hours of transfection, the adherent and floating cells were collected and washed once with PBS, and fixed in 1% paraformaldehyde for 15 minutes. The cells were then spun down, washed with PBS, re-suspended in 70% ethanol, and stored at −20° C. overnight. The cells were then examined for apoptosis. Apoptosis was analyzed using a flow cytometry that detects DNA breaks labeled by fluorescein anti-BrdU antibody and total cellular DNA labeled by propidium iodide (APO-BRDU™ Kit; Pharmingen, San Diego, Calif.). Experiments were conducted a similar fashion with scramble duplex with the following sequence 5'-GCGCGCUUUGUAGGA-UUCG-3' (SEQ ID NO: 47) to determine the specificity of siRNA. To determine the effect of siRNA and scramble duplex treatment on endothelial tube formation, HMVEC were transfected as described earlier. Forty-eight hours after transfection, the adherent cells were collected by trypsinization. The cells were plated at a density of 0.2 million cells/cm² on Lab-Tek II chamber slides (Nalge Nunc International, Naperville, Ill.) coated with matrigel. Tube formation by endothelial cells was examined 24 hours later.

Example 8

VG5Q Anti-Sense and Sense Oligonucleotides

To confirm that suppression of VG5Q expression in results in endothelial cell apoptosis, similar analysis was performed with an anti-sense oligonucleotide against VG5Q. Endothelial cell apoptosis was induced by the anti-sense oligonucleotide. These results confirm that suppression of VG5Q expression induces apoptosis of endothelial cells.

Anti-sense and sense phosphorothioate oligonucleotides targeted to the coding sequence of human VG5Q were designed based on the RNA secondary structure predicted using the program from Dr. M Zuker (Rensselaer Polytechnic Institute, New York). The VG5Q anti-sense oligonucleotide was synthesized as an 18 mer targeted at 5'-ATC ACA AAA ATA GTC CCC-3' (SEQ ID NO: 48) of VG5Q Sigma Genosys (Woodlands, Tex.). Logarithmically growing endothelial cells were transfected by directly adding 5 nmoles of phosphorothioate oligonucleotides into the culture medium. Effect of anti-sense or sense oligonucleotides on endothelial cell apoptosis and tube formation was examined as described for siRNA (Table 4).

Example 9

Suppression of VG5Q and genes associated with apoptosis. To examine the signaling pathway by which silencing of VG5Q expression leads to apoptosis of endothelial cells, GEArray Q series Human Apoptosis Gene Array was probed with total RNA from endothelial cells following 24 hours of exposure to scramble duplex or siRNA1 and siRNA2 against VG5Q. Similar results were obtained for siRNA1 and siRNA2.

cDNA expression array: The array contains 96 cDNA fragments from genes associated with human apoptosis that are printed on a 3.8×4.8 cm nylon membrane (Superarray Inc Bethesda, Md.). HUVEC were grown to 50%-60% confluency, washed with serum free basal media, and transfected with siRNA and Oligofectamine™. The cells exposed to scramble duplex were used as control. After 24 hours of transfection, cells were lysed with 1 ml TRIZOL reagent (Invitrogen, Carlsbad Calif.). RNA was extracted by standard procedures. Total RNA (3 μg) was used as the template for $^{32}$P-labelled cDNA probe synthesis with primer mix provided by the company. Hybridization and washings were performed according to the manufacturer's instruction. A phosphoimager was used to record the image of the array. The image was digitized and gene expression was analyzed after normalizing to one of the house keeping genes on the blot.

Quantitative RT-PCR. For quantitative RT-PCR, random primers and 2 μg of total RNA were used in reverse transcription (RT) using the Reverse Transcription System (Promega). The RT products were mixed with 150 μl with water, and 3 μl (equivalent to 40 ng total RNA) was used for PCR. The PCR cycles are optimized to achieve logarithmic amplification.

Example 10

Identification of a Cell Surface Receptor for VG5Q

Figure 8:
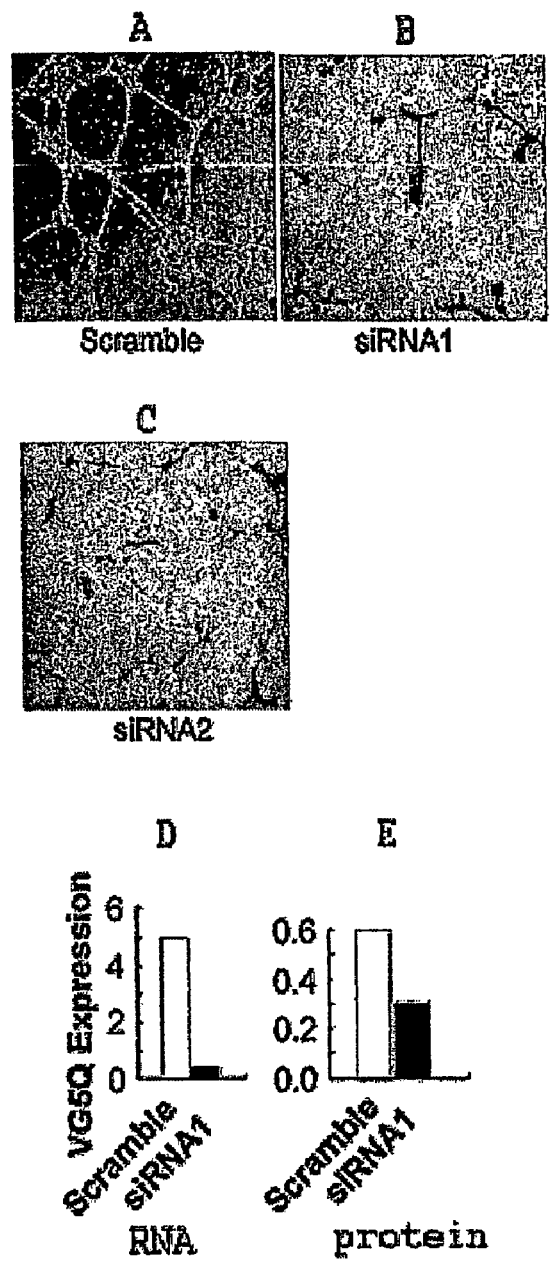
FIG. 8 depicts the effect of siRNA against VG5Q on endothelial tube formation resulting from VG5Q expression.
Figure 9:
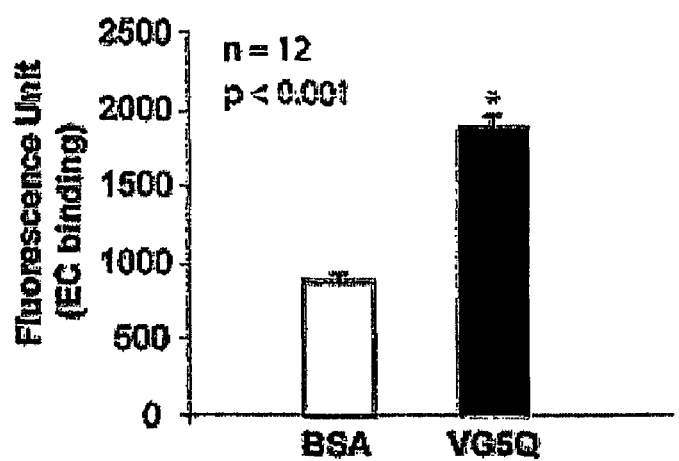
FIG. 9 shows the adhesion of endothelial cells to a plate coated with VG5Q protein via a receptor on the surface of endothelial cells. A multiwell plate was coated with a solution of VG5Q or BSA, unbound protein was removed, and endothelial cells were added to the wells, and incubated. The unbound cells were removed and the wells were read in CytoFluor II Fluorescence Reader to measure fluorescence of adhering cells (vertical axis). Results represent mean readings in 12 replicate wells +/− S.D with the background fluorescence subtracted out. The figure is representative of two independent experiments.

To determine whether there is a cell surface receptor for VG5Q on endothelial cell surface, a cell adhesion assay was carried out. A particular type of cell adhesiveness involves the binding of a receptor to a specific ligand. For example, integrin receptors on a plasma membrane can bind to fibronectin, laminin, or collagen to mediate cell adhesion. Thus, if there is a plasma membrane-anchored receptor for VG5Q, cell adhesion to VG5Q should be detected. The fluorogenic dye calcein acetoxymethyl ester- or calcein AM-based cell adhesion assay was used to detect cell-substratum (VG5Q) adhesion. When nonfluorescent calcein AM is loaded into cells, it is cleaved by endogenous esterases to produce the highly fluorescent and well-retained dye calcein which provides a bright fluorescent, cytoplasmic cell marker. Microplate wells were pre-coated with purified VG5Q, and fluorescently labeled endothelial cells were added into the wells. After incubation, nonadhering cells were removed by washing, and fluorescence of adhering cells was then measured. Higher calcein fluorescence indicates a greater number of adhering cells. As shown in FIG. 8, compared to control BSA, a significantly higher calcein fluorescence was detected for VG5Q. These results indicate that endothelial cells bind or adhere to VG5Q protein, suggesting that there is a plasma membrane receptor for VG5Q on endothelial cell surface. To elucidate the molecular mechanism by which VG5Q promotes angiogenesis, protein factors that associate with VG5Q were isolated using the yeast two-hybrid system with VG5Q as the 'bait'. Sequence analysis showed that one isolated cDNA encoded the carboxy-terminal domain of TWEAK (amino acid residues 136-249), a member of the tumour-necrosis factor (TNF) superfamily that induces angiogenesis in vivo (Wiley, S. R. et al., Cytokine Growth Factor Rev. 2003, 14:241) The direct physical interaction between VG5Q and TWEAK was demonstrated using glutathione S-transferase (GST) pull-down assays with GST-TWEAK protein and in-vitro-translated $^{35}$S-labelled VG5Q (FIG. 10 *a*). In co-immunoprecipitation assays, the anti-VG5Q antibody specifically precipitated a protein recognized by an anti-TWEAK antibody, validating the interaction between VG5Q and TWEAK in vivo (FIG. 10 *b*). Co-immunostaining showed co-localization of the two proteins around the nuclei in HUVECs cultured on plastic dishes. In HUVECs initiating endothelial tube formation on matrigel, VG5Q and TWEAK moved to the cell surface. Together, these results suggest that VG5Q may promote angiogenesis by interacting with TWEAK. TWEAK binds to its receptor, fibroblast-growth-factor-inducible 14 (Fn14), as a homotrimer, and it promotes angiogenesis in vivo (Wiley, S. R. et al., Cytokine Growth Factor Rev., 2003; 14, 241) as potently as VEGF and FGF-2, two well-known angiogenic factors (Yancopoulos, G. D. et al., Nature 2000, 407 :242; Mignatti, P. et al., J Cell Physiol. 1992, 151: 81).

TWEAK treatment has been shown to promote cell proliferation and migration of HUVECs (Lynch, C. N. et al., J. Biol. Chem. 1999, 274:8455.

VG5Q also induces proliferation of HUVECs (thymidine uptake: 680+/−29 for wild-type VG5Q compared with 524+/−14 for control (no VG5Q); P=0.007, n=8). The proliferation of HUVECs was also observed for mutant VG5Q with mutation E133K (thymidine uptake: 711+/−37 compared with control (524+/−14); P=0.001, n=8), but was not significantly different from wild-type VG5Q (P. 0.05, n=8). As angiogenesis is a complex process involving endothelial cell protease secretion, proliferation, migration, adhesion and survival, a major effect of mutation E133K may be more prominent in processes other than proliferation.

Binding Assay: a Falcon 96 well multiwell plate was coated with 2 ug/ml solution of VG5Q or BSA in coating buffer (50 mM NaHCO3, 150 mM NaCl, pH 8.0) and incubated at 4° C. overnight. Next morning unbound protein was removed, and wells were washed with phosphate buffered saline. The wells were than incubated with PBS containing 1% BSA for one hour at room temperature. The wells were washed once with PBS and ready for cell adhesion assay. Endothelial cells were isolated from culture plates with tissue dissociation buffer (EDTA only, no trypsin), and washed with Hanks balanced salt solution (HBSS). The cells were suspended in 1 ml of HBSS, and 40 ug of Calcein AM in 400 ul of HBSS was added. The cells were incubated at 37° C. for 30 minutes. At the end of incubation the cells were diluted to a concentration of 2 million cells/ml in HBSS containing 0.2% BSA. These cells were added to the wells, and incubated for 1 hour. The unbound cells were removed with aspiration. Wells were washed with PBS, and read in CytoFluor II Fluorescence Reader to measure fluorescence of adhering cells (vertical axis). Results represent mean readings in 12 replicate wells +/−S.D. FIG. 8 is representative of two independent experiments.

A receptor for VG5Q was identified and cloned by a yeast two hybrid technology: VEG5Q was fused to the GAL4 DNA-binding domain in the pAS2-CYH2 vector as the bait. The bait was transformed into the yeast strain PJ69-2A (MATa, trp1-901, leu2-3,112, ura3-52, his3-200, gal4Δ, gal80Δ, LYS2::GAL1UAS-GAL1TATA-HIS3, GAL2UAS-GAL2TATA-ADE2), and mated with one of three commercially available libraries, the human brain, heart, and kidney pretransformed MATCHMAKER cDNA libraries (Clontech). These pretransformed cDNA libraries are high-complexity cDNA libraries that have been cloned into a GAL4 activation domain vector (pACT2) and introduced into yeast strain Y187 (MATα, ade2-101, trp1-901, leu2-3,112, ura3-52, his3-200, gal4A, gal80A, met, URA3::GAL1UAS-GAL1TATA-lacZ). PJ69-2A is an advanced yeast mating strain that contains two nutritional markers ADE2 and HIS3 under the control of different promoters. Due to the double screening markers, fewer false positives are generated. Positive clones were recovered and sequenced.

Other methods to identify VG5Q receptors: Similarly, the VG5Q receptor is isolated by expression cloning: Expression cloning is a technique that can be used to identify and clone genes that encode proteins (e.g receptor for VG5Q) that interact with a protein of interest (e.g. VG5Q). VG5Q is used as a probe to screen a lambda bateriophage-derived cDNA expression library (e.g. an expression library constructed using lambda gt11). This procedure leads to the direct isolation of genes encoding the interacting protein. Alternatively, the VG5Q receptor is isolated by phage display: VG5Q is pre-coated in a well, and phage prep (tens of billions of peptides and proteins) from a Phage Display cDNA library is applied to the well, and incubated on the well surface. This allows phage whose displayed peptide or domain can bind VG5Q to bind the immobilized VG5Q. Unbound phage are washed away. Bound phage are eluted and propagated by infecting fresh E. coli host cells. Phage DNA is isolated and the insert (VG5Q receptor) is sequenced.

Another method to isolate the VG5Q receptor is by a proteomics approach: cell extract (total protein) is fractionated through SDS-Polyacrylamide gels (PAGE), transferred to Nylon membranes, and probed with 125I-labeled VG5Q protein. The membranes are probed with VG5Q protein, and the binding is detected with an antibody to VG5Q. Protein bands on the gel that can bind to VG5Q protein are excised from the gels and their identity is determined by Mass Spectrometry. The sequence information is then used to search the protein and gene sequence databases and identify the protein. Alternatively, cell extract (total protein) can be precleared with Ni-NTA magnetic agarose beads, and incubated with purified His-tagged VG5Q. The mixture is then incubated with Ni-NTA beads, washed five times with lysis buffer, and eluted with elution buffer (8M urea, 0.1M NaH2PO4, 0.01 M Tris-HCl, pH4.5). The elutant is mixed with the SDS protein loading buffer, and separated by SDS-PAGE. The gel is stained with coomassie-blue, and the band of interest is excised from the gel, and analyzed using Mass-Spectrometry. Coprecipitation represents another route to isolate the receptor: cells are lysed and a whole-cell extract is prepared under nondenaturing conditions. The cell extract is incubated with VG5Q and an antibody against VG5Q. The mixture is incubated with protein A-Sepharose which binds antibody. Sepharose beads are collected by centrifugation, and unbound proteins are removed by washing. The VG5Q receptor is dissociated from protein A-Sepharose, and separated by SDS-PAGE. The gel is stained with coomassie-blue, and the band of interest is excised from the gel, and analyzed using Mass-Spectrometry. Affinity chromatography is also used to isolate the VG5Q receptor: VG5Q or antibodies against VG5Q are used to prepare chromatographic columns. Cell extract can be run through the column, and VG5Q-VG5Q receptor complex will be retained in the column and later dissociated from the column. The dissociated proteins are separated through SDS-PAGE, stained, and sequenced using Mass-Spectrometry.

Example 11

In vivo studies using antibodies against VG5Q: In vivo studies are designed to determine if an anti-VG5Q monoclonal antibody of the present invention blocks the growth of VG5Q-expressing endothelial and/or associated tumor cells. In these experiments, a human cancer cell line is known to efficiently induce tumor angiogenesis in a mouse model. This cell line is then injected into athymic nude mice while the animals receive intraperitoneal injections of predetermined amounts of either anti-VG5Q antibody or control antibodies. The mice receive subsequent antibody treatments, for example, on days 3, 5, 7, 9, 11, 13, 15, 17, and 19. Tumor size is measured daily with a caliper and tumor volume calculated by the formula of Baselga (J. Natl. Cancer Inst. 1993, 85: 1327-1333). Measurements are taken at least three times per week and tumor volume calculated as described above. A comparison between the group receiving anti-VG5Q antibody and the control group of reduction in tumor growth reveals whether VG5Q antibody-treated mice show an overall delay in tumor progression. Statistical analysis of the data is performed to assess differences in tumor size between the two groups. Data is subjected to a standard analysis of covariance where tumor size was regressed on time with treatment as a covariate. The results show whether a monoclonal antibody to VG5Q inhibits tumor invasion by abrogating angiogenesis.

Example 12

In vivo angiogenesis assays. The effect of VG5Q on angiogenesis in vivo is assayed using other well-established assays: the mouse corneal micropocket assay, the sponge/matrigel plug assay, and the hind limb ischemic model. As VG5Q interacts with another angiogenic factor TWEAK, and both can promote EC proliferation and angiogenesis, it is likely that these two proteins may act synergistically. VG5Q may also act synergistically with other angiogenic factors such as VEGF-A and FGF-2. A side-by-side comparison is made between VG5Q alone and in combination with TWEAK, VEGF-A, and FGF-2 to study whether these factors act synergistically to promote angiogenesis. As the establishment of stable and functional blood vessels is a complex process that requires the actions from several angiogenic factors, it is important to investigate the impact of combinations of these factors on blood vessel growth and angiogenesis.

Mouse corneal micropocket assay. The mouse corneal assay is as follows. The mice are anaesthetized with intraperitoneal injection of Avertin (30-40 micrograms/gram body weight), or sodium pentobarbital (70 μg/gram body weight), or other appropriate agents. Avertin and sodium pentobarbital are the most commonly used anesthetizing agents for mice, and they are effective and widely used in the research community. The eye for surgery is topically anesthetized with 0.5% proparacaine, and the globes are proptosed with a jeweler's forceps. A corneal micropocket is created with a modified von Graefe cataract knife in the left eye of each male 5- to 6-wk-old C57BL6/J mouse. A micropellet (0.35×0.35 mm) of sucrose aluminum sulfate (Bukh Meditec, Copenhagen, Denmark) is coated with hydron polymer type NCC (IFN Sciences, New Brunswick, N.J.) containing varying amounts of purified VG5Q, TWEAK VEGF, FGF-2, or various combinations of these factors, and implanted into the pocket. The pellet is positioned 0.6-0.8 mm from the corneal limbus, and after implantation, erythromycin/ophthalmic ointment is applied to the left eye. The eye is examined by a slit-lamp biomicroscope on day 5 after pellet implantation, and vessel length and clock hours of circumferential neovascularization is measured.

Sponge/Matrigel Plug Assay. There are several variations for this assay, but they all are based on the same principle. In brief, purified VG5Q (TWEAK, VEGF, FGF-2 or their combinations) is introduced into cold liquid Matrigel (which is then injected subcutaneously in mice), or spotted on the sponge through matrigel or agarose (which is then implanted subcutaneously in mice). For implantation of sponges or matrigel plugs, mice are anaesthetized with intraperitoneal injection of Avertin (30-40 micrograms/gram body weight), or sodium pentobarbital (70 μg/gram body weight), or other appropriate agents. The flanks of the animals are shaved and disinfected with iodophor and isopropyl alcohol. A 2 cm incision is made in the flank and a subcutaneous pocket is made by blunt dissection. The sponges or matrigel plugs are then slid at least 2 cm into the pocket with the 180 um filter side facing the skin. The incision is closed by 4-6 (6 mm) stainless steel staples. Days later, the matrigel plugs or sponges are recovered, and angiogenesis is then assessed by examining for vascular density. One detailed protocol was described previously (Akhtar N, et al., Angiogenesis 2002, 5:75-80)

Mouse hind limb ischemic model. The potential of VG5Q to stimulate the growth of preexisting arterial collaterals and their second- and third-generation side branches ('collateral growth') is evaluated by treating mice with VG5Q after ligation of their femoral artery (the mouse ischemic limb model). This procedure creates ischemia in the left hind limb with the right leg serving as a control. The mice are anaesthetized with intraperitoneal injection of Avertin (30-40 micrograms/gram body weight), or sodium pentobarbital (70 µg/gram body weight), or other appropriate agents. The first surgery is carried out through a midline lapartomy. Under a dissecting microscope, all left side branches of aorta distal to the renal arteries and all left side branches of iliac artery will be ligated with 6-0 resorbable suture. These ligated vessels are spermatic, left lumbar, ileolumbar, inferior mesenteric, caudal arteries and all branches from the left iliac artery down to the inguinal ligament. After 5 days, the mice are anaesthetized with intraperitoneal injection of Avertin (30-40 micrograms/gram body weight), or sodium pentobarbital (70 µg/gram body weight), or other appropriate agents, and the femoral artery is ligated, by a left inguinal incision at a position close to the origin of the superficial epigastric artery, which is subsequently ligated. On the same day as the second operation, a micropellet (0.35×0.35 mm) of sucrose aluminum sulfate (Bukh Meditec, Copenhagen, Denmark) is coated with hydron polymer type NCC (IFN Sciences, New Brunswick, N.J.) containing varying amounts of purified VG5Q, TWEAK VEGF, FGF-2, or various combinations of these factors, and implanted into intramuscular pockets near the ligation site. Alternatively, soluble growth factors (VG5Q and FGF-2) in 400 ul PBS are injected into 3 sites close to the ligation site, and treatment continues for a total of 12 days. The mice are then examined for blood vessel formation and blood flow.

Angiogenesis by VG5Q delivered with the AAV Helper-Free System, a viral-based gene delivery system (Stratagene). All studies described above test whether VG5Q promotes angiogenesis when administered as the recombinant protein. The ability of VG5Q to promote angiogenesis when delivered as VG5Q-coding DNA as part of an expression vector is herein assessed. If successful, this method provides a novel gene therapy approach to stimulate vessel formation by delivering a vector containing DNA encoding VG5Q to targeted cells. As angiogenesis is a complex disease, different methods of angiogenesis have different sensitivity, and can provide complementary, confirmatory evidence. Multiple angiogenesis assays are commonly performed to unequivocally demonstrate that a protein factor has angiogenic activity. Both adenovirus-delivered VG5Q and recombinant VG5Q will be assayed.

(i) Preparation of Viral Stocks: VG5Q is cloned into ITR-containing vector (PAAV-MCS, Stratagene). The anti-sense cDNA of VG5Q is cloned into the same vector as a control. The pAAV-lacZ in the Stratagene kit is also used as a control. The recombinant expression plasmid is co-transfected into HEK-293 cells (ATCC Catalog #CRL-1573) with pHelper (carrying adenovirus-derived genes), and PAAV-RC (carrying AAV-2 replication and caspid genes) which together supply all of the transacting factor required for AAV replication and packaging in HEK293 cells. Three days following the transfection of HEK 293 cells, growth media is collected and the adherent cells is scraped and pooled with the growth medium. The cell suspension is subjected to four rounds of freeze/thaw by alternating the tubes between the dry ice-ethanol bath and 37° C. water bath and vortexing. The cellular debris is removed by centrifugation at 10,000 g for 10 minutes at room temperature and the supernatant (Primary virus stock) is stored at −80° C. The titer of the primary virus stock is measured.

(ii) The pAAV-VG5Q virus particles and pAAV-lacZ and pAAV-anti-VG5Q control viruses are spotted on micropellets of sucrose aluminum sulfate and used for mouse corneal pocket assays as described above. The virus particles are also mixed with matrigel or spotted on sterile gelfoam absorbable sponges for the sponge/matrigel plug angiogenesis assays as described above.

Example 12

In vivo tumor growth and metastasis assays: The growth and metastasis of tumors are dependent on angiogenesis that provides an adequate supply of oxygen-rich blood. siRNAs and anti-sense oligos against VG5Q disrupt vessel formation in an in vitro matrigel angiogenesis assay, and also cause apoptosis in endothelial cells only among four cell types examined (other cells are smooth muscle cells, fibroblast, and HEK293 cells). These results provide a rationale for VG5Q-mediated anti-tumor therapy.

The mice are anaesthetized with intraperitoneal injection of Avertin (30-40 micrograms/gram body weight), or sodium pentobarbital (70 µg/gram body weight), or other appropriate agents. Various tumor cells, e.g. A549 cells from rapidly growing solid tumors, Hep 3B liver cancer cells, U-87 human glioma cell-derived tumors, lung cancer cells H1299G1, H1299G3, G2G31-80, SKOV-2 ovarian cancer cells, T-80H cells, or others, are injected into the flanks of immunodeficient nude mice, and allow to grow to 50 to 70 µl. These tumors are injected with siRNAs and anti-sense oligos against VG5Q repeatedly. Alternatively, tumor cells are mixed with antiVG5Q agents before injection. The mice are kept in pathogen-free environment and examined every 2 days for 2-5 months. The size of the tumors is measured. The detailed protocol was described previously (Doronin et al., J Virology 2000, 74:6174-6155). Many tumor cells are tested because VG5Q-based anti-angiogenic therapy may have selectivity for specific tumors. As the dependence of tumor growth on angiogenesis differs among different tumors, testing many different tumors determines the effectiveness of VG5Q-based antiangiogenic therapy on each tumor.

Other anti-VG5Q agents that are used in this assay include antibodies against VG5Q, pAAV-antisense-VG5Q, chemical compounds against VG5Q, and retroviruses or pAAV constructs that express siRNAs targeting VG5Q.

Example 13

Identification of Functional Domain of VG5Q. Various deletions and mutations of VG5Q are created and assayed for EC and VSMC proliferation, migration, adhesion, and in vivo angiogenesis to identify specific domains in VG5Q that are responsible for these functions. These deletions/mutations are used to identify VG5Q domains that interact with other proteins, including TWEAK and other VG5Q-interacting proteins that are identified in this study. The specific methods include mutagenesis and functional assays. Identification of functional domains of VG5Q is also helpful in designing mutants with greater angiogenic potential or with dominant-negative type blocking effects.

Mutagenesis: The initial focus is on putative functional domains of VG5Q, including the FHA domain, the G-patch domain, the C-terminus after G-patch, and the N-terminus before the FHA domain. Each domain is deleted separately. These deletions have already been created by PCR amplification of the VG5Q portion before the domain and the portion after the domain, and ligation of two PCR fragments. These deletions are characterized as described in "Functional assays" section below. If the functional region turns out to be either the N-terminus or the C-terminus, further systematic deletion analysis is performed.

For the systematic deletion strategy, a series of N-terminal and C-terminal deletions is created. Each succeeding deletion truncates 10 more amino acids. When a functional region is defined by deletion analysis, it is further delineated by alanine-scanning mutagenesis. All mutations will be verified by DNA sequence analysis, and their expression will be examined by Western blot analysis before proceeding to functional analysis.

Functional assays: Each mutant VG5Q protein will be expressed using the mutant constructs transformed into E. coli. Each mutant His-VG5Q protein will be purified using a Ni-NTA agarose column. The eluted protein is dialyzed, and quality of purification is examined by 20' SDS-PAGE and Western blot analysis. Each mutant VG5Q protein is then used in EC and VSMC proliferation, migration and adhesion assays, and in vivo CAM and sponge/matrigel plugs angiogenesis assays.

In vitro GST-pull down and co-immunoprecipitation are used to determine whether each deletion still binds to TWEAK or VG5Q-interacting. Mutant expression constructs will be used for producing $^{35}$S-labeled VG5Q in rabbit reticulocyte lysates for GST-pull down with the GST-TWEAK fusion protein. Each mutant construct will be transfected into a stable HEK-293 cell line expressing TWEAK (available in the PI's laboratory), and co-immunoprecipitation is performed as described (Tian X L, et., Nature 2004, 427:640-645; Fan C, et al., J Med. Genet. 2003, 40:e29; Fan C, et al., J Biol. Chem. 2003, 278:8780-8785).

These studies define the functional domains and regions of VG5Q. When such domains are identified, bioinformatics tools are used to identify other proteins with homologous domains. These studies may define a class of proteins with potentially similar functions.

Example 14

To investigate the in vivo physiological effect of KTS-associated mutation E133K of VG5Q in transgenic mice overexpressing the mutation. VG5Q mutation E133K is associated with vascular disease KTS. Mutation E133K causes increased angiogenesis and acts by a gain-of-function mechanism, thus, mice that express wild type VG5Q or mutant E133K VG5Q and determine may recapitulate the vascular phenotype seen in humans. It is important to note that there is no animal model for KTS to date.

The native VG5Q promoter (VG5Qp) will be fused to wild type or mutant VG5Q cDNA, and used for generating the transgenic mouse lines. Transgenic founders will be screened using human specific VG5Q primers. Expression of the transgene in progeny will be compared in skeletal muscle, heart, and aorta using RT-PCR with human specific primers, and using Western blotting with a VG5Q specific antibody 23;56. Wild type and mutant VG5Q transgenics will be examined carefully for general pathologic abnormalities by complete autopsy. Detailed studies will then be focused on blood vessels during embryogenesis and in vessels embedded in various organs including the limbs, kidneys, brain, heart, and other organs.

Embryos will be studied at different development stages for abnormal vascular phenotype or other phenotypes. The vascular phenotype in the embryos is examined by focusing on (i) the primary capillary plexus that surrounds the developing forebrain, which normally develops into a highly branched and intricate vascular network by E10.5, (ii) the head region, which should display extensive vascular branching and remodeling into large and small vessels by E11.5, (iii) the developing eyes, (iv) the primitive gut and umbilical vasculature, (v) the intersomitic vessels, and finally (vi) the yolk sac vasculature.

The tissue immunostaining is performed for those organs that are affected by KTS, including limbs, kidney, and brain, and other organs such as heart, liver, lung, and intestine. In both whole-mount embryos and adult organ immunostaining experiments, the vascular abnormalities include appearance of vessels (sizes, number of branches, etc.), EC and VSMC, number of vessels, and complexity of vessels, and any overt defects such as thinning, hyperplasia, or inflammatory infiltrates in the vessels. Positive results support the genetic finding that the VG5Q E133K mutation causes vascular defects in KTS, and further confirms VG5Q as an important vascular gene. Endothelial cells (EC) and vascular smooth muscle cells (VSMC) are isolated from wild type and mutant VG5Q transgenics, and are used for a variety of studies. Further studies and phenotypic analysis are determined and designed based on the phenotype of the mutant animals.

Example 15

To examine the physiological roles of VG5Q by characterizing VG5Q knockout mice. The VG5Q knockout mice is the product of a strategy involving homologous recombination in mouse embryonic stem (ES) cells. This strategy has been widely used to generate animal models of human genetic disorders and to examine the roles of specific genes in development. A targeting vector that could produce a null mutant allele for VG5Q by homologous recombination has VG5Q exons 2-11 deleted and replaced with the neomycin-resistance (neo) gene. Southern blot analyses revealed that the successful targeting of the endogenous VG5Q was achieved. 7 of 259 embryonic stem (ES) cell clones were correctly targeted. The ES cells were derived from the 129 sv/Tac strain of mice. The targeted ES clones have been injected into blastocysts on Feb. 23, 2004. Male chimeras will be bred to C57BL/6 females. Chimeras will transmit the mutant allele to their offspring, generating F1 heterozygotes. Heterozygous mice will be bred further to each other to generate homozygous. Both heterozygous and homozygous mice will be characterized. PCR or Southern blot analyses using tail DNA will be used for genotyping to determine if a mouse is heterozygote or homozygote. RT-PCR, Northern blot, and Western blot analyses will be used to determine the expression level of VG5Q. The knockout mice will be phenotypically characterized as we have described for wild type and E133K VG5Q transgenic in the previous section.

If the mice lacking VG5Q may die during embryonic development the effects of haploinsufficiency of this protein on vascular growth and vascular development using heterozygous mice is studied. Moreover, embryos are studied at different developmental stages to determine when the deficiency becomes lethal. These embryos are studied for abnormal vascular phenotype or other phenotypes to elucidate the detailed physiological role of VG5Q in vascular development. This is the approach that was used for studying knockout mice for TIE217 and ANG118. If heterozygous mice also die, VG5Q+/− embryos are studied as described for VEGF+/−

Example 16

Expression of VG5Q in Human Glioma Tissues

Immunostaining of primary human glioma tissue demonstrated expression of VG5Q protein in blood vessels and tumor cells. This was confirmed by smooth muscle α-actin controls. Immunostaining was performed as per Example 1, supra, but with a different antibody against human VG5Q made with the CEYEDEKTLKNPKYKDRAGKR peptide (SEQ ID NO: 49). The antibody was made in rabbits and purified as described in Example 1, supra, and assayed by Western Blot and on heart sections prior to the glioma immunostaining experiment.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

---

What is claimed is:

1. An isolated nucleic acid comprising a nucleic acid sequence selected from the group consisting of:
   (a) a nucleic acid sequence that fully encodes a full length polypeptide with the amino acid sequence of SEQ ID NO: 2;
   (b) a nucleic acid comprising the full length sequence shown in SEQ ID NO: 1;
   (c) a nucleic acid sequence that fully encodes a full length polypeptide with the amino acid sequence of SEQ ID NO: 4
   (d) a nucleic acid comprising the full length sequence shown in SEQ ID NO: 3; and
   (e) the full complement of (a), (b), (c) or (d).

2. The nucleic acid of claim 1 which hybridizes under high stringency conditions to a nucleic acid having the sequence of SEQ ID NO: 1.

3. The nucleic acid of claim 1 which hybridizes under high stringency conditions to a nucleic acid having the sequence of SEQ ID NO: 3.

4. The nucleic acid of claim 1 wherein the sequence is 90% identical to SEQ ID NO: 1.

5. The nucleic acid of claim 1 wherein the sequence is 90% identical to SEQ ID NO: 3.

6. The nucleic acid according to claim 1, wherein the nucleic acid is DNA.

7. The nucleic acid according to claim 1, wherein the nucleic acid is RNA.

8. A vector comprising the nucleic acid described in claim 1.

9. An isolated host cell comprising the vector of claim 8.

10. A method of producing VG5Q protein, which method comprises culturing the host cell of claim 9 under conditions such that the VG5Q protein is expressed.

11. A method of producing cells expressing VG5Q protein, which method comprises introducing the vector of claim 8 into cells.

12. A nucleic acid delivery vehicle for inducing angiogenesis in a mammal, the nucleic acid delivery vehicle comprising a nucleic acid comprising the isolated nucleic acid of claim 1, and further comprising a nucleic acid delivery carrier.

13. The nucleic acid delivery vehicle according to claim 12, wherein the nucleic acid is DNA.

14. The nucleic acid delivery vehicle according to claim 13, which comprises the nucleotide sequence selected from the group consisting of SEQ ID NO: 1 and SEQ ID NO: 3.

15. The nucleic acid delivery vehicle according to claim 13, which codes for a polypeptide comprising the amino acids selected from the group consisting of SEQ ID NO: 2 and SEQ ID: 4.

16. The nucleic acid delivery vehicle of claim 12, wherein the nucleic acid delivery carrier is a vector selected from the group consisting of a plasmid, a retrovirus, an adenovirus, and a virus.

17. The nucleic acid delivery vehicle of claim 12, wherein the nucleic acid delivery carrier is a lipid compound.

18. The nucleic acid delivery vehicle of claim 17, wherein the lipid compound is selected from the group consisting of liposomes, lipofectins, cytofectins, and lipid-based positive ions.

19. The nucleic acid delivery vehicle of claim 12, wherein the nucleic acid delivery carrier is a gene gun.

20. A method of enhancing and/or inducing the expression of VG5Q in a mammal comprising administering the nucleic acid delivery vehicle of claim 12 to target cells of the subject.

* * * * *